(12) United States Patent
Nezami

(10) Patent No.: US 12,213,958 B2
(45) Date of Patent: Feb. 4, 2025

(54) COMPOSITIONS, METHODS, SYSTEMS AND/OR KITS FOR PREVENTING AND/OR TREATING NEOPLASMS

(71) Applicant: Research Cancer Institute of America, Fresno, CA (US)

(72) Inventor: Mohammed Amin Nezami, Fresno, CA (US)

(73) Assignee: Research Cancer Institute of America, Newport Beach, CA (US)

( * ) Notice: Subject to any disclaimer, the term of this patent is extended or adjusted under 35 U.S.C. 154(b) by 1018 days.

(21) Appl. No.: 16/764,821

(22) PCT Filed: Nov. 15, 2018

(86) PCT No.: PCT/US2018/061390
§ 371 (c)(1),
(2) Date: May 15, 2020

(87) PCT Pub. No.: WO2019/099750
PCT Pub. Date: May 23, 2019

(65) Prior Publication Data
US 2021/0015787 A1 Jan. 21, 2021

Related U.S. Application Data

(60) Provisional application No. 62/588,188, filed on Nov. 17, 2017.

(51) Int. Cl.
| | | |
|---|---|---|
| *A61K 31/352* | (2006.01) | |
| *A61K 31/192* | (2006.01) | |
| *A61K 31/436* | (2006.01) | |
| *A61K 31/454* | (2006.01) | |
| *A61K 31/506* | (2006.01) | |
| *A61K 31/517* | (2006.01) | |
| *A61K 31/519* | (2006.01) | |
| *C07K 16/22* | (2006.01) | |
| *C07K 16/28* | (2006.01) | |
| *C07K 16/32* | (2006.01) | |
| *A61K 9/00* | (2006.01) | |
| *A61K 9/51* | (2006.01) | |
| *B82Y 5/00* | (2011.01) | |

(52) U.S. Cl.
CPC .......... *A61K 31/352* (2013.01); *A61K 31/192* (2013.01); *A61K 31/436* (2013.01); *A61K 31/454* (2013.01); *A61K 31/506* (2013.01); *A61K 31/517* (2013.01); *A61K 31/519* (2013.01); *C07K 16/22* (2013.01); *C07K 16/2887* (2013.01); *C07K 16/32* (2013.01); *A61K 9/0019* (2013.01); *A61K 9/0053* (2013.01); *A61K 9/5153* (2013.01); *B82Y 5/00* (2013.01)

(58) Field of Classification Search
CPC .. A61K 31/352; A61K 31/192; A61K 31/436; A61K 31/454; A61K 31/506; A61K 31/517; A61K 31/519; C07K 16/22; C07K 16/32
USPC ........................................................ 514/456
See application file for complete search history.

(56) References Cited

U.S. PATENT DOCUMENTS

| | | | |
|---|---|---|---|
| 4,569,836 A | 2/1986 | Gordon | |
| 6,299,925 B1 | 10/2001 | Xiong et al. | |
| 6,376,525 B1 | 4/2002 | Kong | |
| 8,933,078 B2 * | 1/2015 | Nezami | A61K 31/353 514/19.5 |
| 9,364,500 B2 | 6/2016 | Nezami | |
| 9,439,899 B2 | 9/2016 | Proia | |
| 10,016,392 B2 | 6/2018 | Nezami | |
| 2003/0103954 A1 | 6/2003 | Rosenbloom | |
| 2003/0105031 A1 | 6/2003 | Rosenbloom | |
| 2004/0258674 A1 | 12/2004 | Jalili | |
| 2006/0035981 A1 | 2/2006 | Mazzio et al. | |
| 2006/0057230 A1 | 3/2006 | Chow | |
| 2007/0112053 A1 | 5/2007 | Pickett et al. | |
| 2007/0190022 A1 | 8/2007 | Bacopoulos et al. | |
| 2007/0190114 A1 | 8/2007 | Smart | |
| 2008/0305096 A1 | 12/2008 | Verdegem et al. | |
| 2010/0239596 A1 | 9/2010 | Lee et al. | |

(Continued)

FOREIGN PATENT DOCUMENTS

| | | |
|---|---|---|
| CN | 1537161 | 10/2004 |
| CN | 1965715 | 5/2007 |

(Continued)

OTHER PUBLICATIONS

Dinarvand et al International Journal of Nanomedicine, 2011, 6, 877-895) (Year: 2011).*
Bennouna et al Future Oncol., 2016, 12(3), 355-372 (Year: 2016).*
Cruz-Correa, M., et al., Combination Treatment With Curcumin and Quercetin of Adenomas in Familial Adenomatous Polyposis, Clinical Gastgroenterology and Hepatology, vol. 4, No. 8, pp. 1035-1038, 2006.
Hashemzaei, M., et al., Anticancer and apoptosis-inducing effects of quercetin in vitro and in 1-2 vivo. Oncology Reports, vol. 38, No. 2, pp. 819-828, 2017.

(Continued)

*Primary Examiner* — Yevgeny Valenrod
(74) *Attorney, Agent, or Firm* — Knobbe, Martens, Olson & Bear, LLP

(57) ABSTRACT

Provided herein are compositions, methods, systems and/or kits for preventing and/or treating neoplasms using at least one modulator selected from quercetin, sodium phenyl butyrate and epigallocatechin-3-gallate in combination with one or more anti-cancer agents. The compositions, methods, systems and/or kits are used to prevent and/or treat neoplasms that are resistant to the one or more anti-cancer agents when administered alone. Also provided are nanoformulations based on nanoparticles with one or more anti-cancer agents and/or one or more modulators for preventing and/or treating neoplasms.

42 Claims, 49 Drawing Sheets

(56) References Cited

U.S. PATENT DOCUMENTS

| | | |
|---|---|---|
| 2010/0316733 A1 | 12/2010 | Locklear |
| 2010/0330087 A1 | 12/2010 | Newell et al. |
| 2011/0104100 A1 | 5/2011 | Riordan et al. |
| 2011/0118309 A1 | 5/2011 | Atadja |
| 2011/0224290 A1 | 9/2011 | Estrela Ariquel et al. |
| 2012/0121730 A1 | 5/2012 | Singh |
| 2012/0269861 A1 | 10/2012 | Sherman et al. |
| 2013/0011488 A1 | 1/2013 | Nezami |
| 2013/0014753 A1 | 1/2013 | Nezami |
| 2013/0129809 A1 | 5/2013 | Srivastava et al. |
| 2015/0366838 A1 | 12/2015 | Lines |
| 2017/0014376 A1 | 1/2017 | Nezami |
| 2017/0020842 A1 | 1/2017 | Elmann |
| 2017/0224654 A1 | 8/2017 | Armstrong et al. |
| 2017/0285027 A1 | 10/2017 | Fantl |
| 2018/0133278 A1 | 5/2018 | Atamaniuk et al. |
| 2019/0125791 A1 | 5/2019 | Wilmotte |
| 2019/0167634 A1 | 6/2019 | Nezami |
| 2020/0147030 A1 | 5/2020 | Nexami |
| 2020/0206183 A1 | 7/2020 | Nezami |
| 2021/0283149 A1 | 9/2021 | Nezami |
| 2021/0401799 A1 | 12/2021 | Nexami |
| 2022/0087946 A1 | 3/2022 | Nezami |
| 2023/0072294 A1 | 3/2023 | Nezami |

FOREIGN PATENT DOCUMENTS

| | | |
|---|---|---|
| EP | 1 847 274 | 10/2007 |
| JP | 05-070348 | 3/1993 |
| JP | 20060298781 | 11/2006 |
| WO | WO 97/47317 | 12/1997 |
| WO | WO 05/023179 | 3/2005 |
| WO | WO 05/083123 | 9/2005 |
| WO | WO 06/059237 | 6/2006 |
| WO | WO 07/121088 | 10/2007 |
| WO | WO 08/011363 | 1/2008 |
| WO | WO 08/082856 | 7/2008 |
| WO | WO 2009/019721 A2 | 2/2009 |
| WO | WO 09019721 | 2/2009 |
| WO | WO 11/112156 | 9/2011 |
| WO | WO 14/091078 | 6/2014 |
| WO | WO 14/111268 | 7/2014 |
| WO | WO 16/054237 | 4/2016 |
| WO | WO 18/170457 | 9/2018 |
| WO | WO 2018/170457 A1 | 9/2018 |

OTHER PUBLICATIONS

International Search Report and Written Opinion, mailed Jan. 28, 2019, in International Application No. PCT/US2018/061390.

Alexandrov et al., Aug. 2013, Signatures of mutational processes in human cancer, Nature, 500:415-420.

Ansel et al., 1999, Drug dosage and terminology, in Pharmaceutical Dosage Forms and Drug Delivery Systems, 7th Ed., Lippincott Williams & Wilkins, p. 48.

Arney, Oct. 24, 2014, Coming ever closer—first PARP inhibitor licensed in Europe, Cancer Research UK, https://news.cancerresearchuk.org/2014/10/24/coming-ever-closer-first-part-inhibitor-on-track-to-be-licensed-in-europe, 6 pp.

Azvolinsky, Mar. 16, 2012, MBCC: PARP inhibitors for breast cancer—which subpopulation to target?, https://www.cancernetwork.com/view/mbcc-parp-inhibitors-breast-cancerwhich-subpopulation-target, 3 pp.

Chen et al., 2011, Green tea epigallocatechin gallate enhances therapeutic efficacy of temozolomide in orthotopic mouse glioblastoma models, Cancer Letters, 302:100-108.

Ciesielski et al., 2020, Epigallocatechin-3-gallate (EGCG) alters histone acetylation and methylation and impacts chromatin architecture profile in human endothelial cells, Molecules, 25:2326.

Harris et al., Oct. 2016, Quercetin as an emerging anti-melanoma agent: a four-focus area therapeutic development strategy, Frontiers in Nutrition, 5(48), 14 pp.

Hu et al., 2016, Pharmacokinetics and antitumor efficacy of DSPE-PET2000 polymeric liposomes loaded with quercetin and tehmozolomide: analysis of their effectiveness in enhancing the chemosensitization of drug-resistant glioma cells, International Journal of Molecular Medicine, 37:690-702.

Lin et al., 2012, Inhibition of mitochondria- and endoplasmic reticulum stress-mediated autophagy augments temozolomide-induced apoptosis in glioma cells, PLOS One, 7(6):e38706.

Nagane, Jan. 2015, Dose-dense temozolomide: is it still promising? Neural. Med. Chir. 55(1):38-49.

Reagan-Shaw et al., Mar. 2007, Dose translation from animal to human studies revisited, The FASEB Journal, 22:659-661.

Schmutzler et al., 2000, Innovative strategies for the treatment of thyroid cancer, European Journal of Endocrinology, 143:15-24.

Sikora, Sep. 10, 2001, Cancer drug development in the post-genomic age, Current Science, 81(5):549-554.

Zips et al., 2005, New anticancer agents; in vitro and in vivo evaluation, In Vivo, 19:1-8.

Cheng et al., Aug. 31, 1989, The study of green extract's anti-tumor effect and mechanism of TPA, Zhonggu Kuangzhan Institute of Technology, 11(4):259-264.

Xu et al., Mar. 16, 2015, Enhancing the anti-colon cancer activity of quercetin by self-assembled micelles, International Journal of Nanomedicine, 10:2051-2063.

Xiao et al., Dec. 31, 1993, University Health Guide, Wubian Dayan Publishing House, 217.

Zhang , Nov. 15, 2009, Inhibition of glycolysis to the biologic characteristics of pancreatic cancer cell PANC-1 and it mechanism, Kyangyao Health Science and Technology Appraisal, p. 10.

Zheng et al., Feb. 28, 2010, Clinical Biochemical Tests, Zhongukuang Pharmaceutical Technology Press, pp. 88-90.

Zhou et al., Dec. 31, 1992, Cancer change, abnormal change and sudden change, Research on Cancer Suppressor, 4(2):35-40.

American Cancer Society, 2019, How chemotherapy drugs work, https://www.cancer.org/content/dam/CRC/PDF/Public/8418.00.pdf, 9 pp.

Patnaik et al., Jun. 2019, Drugs targeting epigenetic modifications and plausible therapeutic strategies against colorectal cancer, Frontiers in Pharmacology, 10(588), 15 pp.

Taylor, 2017, Synergism of quercetin and sodium butyrate for controlling growth of glioblastoma, Master's thesis, University of South Carolina, retrieved from https://scholarcommons.sc.edu.etd.4149, 102 pp.

Xintaropoulou et al., 2008, A comparative analysis of inhibitors of the glycolysis pathway in breast and ovarian cancer cell line models, Oncotarget, 6(27):25677-25695.

Akbas et al, "The effect of quercetin on topotecan cytotoxicity in MCF-7 and MDA-MB 231 human breast cancer cells." J Surg Res. May 1, 2005;125(1):49-55.

Alleva et al., 2005, α-Lipoic acid supplementation inhibits oxidative damage, accelerating chronic wound healing in patients undergoing hyperbaric oxygen therapy, Biochemical and Biophysical Research Communications, 333:404-410.

American Cancer Society, Quercetin, 4 pp., no date.

Amirkhosravi et al., "Pentoxifylline inhibits hypoxia-induced upregulation of tumor cell tissue factor and vascular endothelial growth factor." ThrombHaemost. Oct. 1998;80(4):598-602.

Arce et al., 2006, A proof-of-principle study of epigenetic therapy added to neoadjuvant doxorubiin cyclophosphamide for locally advanced breast cancer, PLoS ONE, 2006, 1(1):e98.

Armeanu et al., "Natural killer cell-mediated lysis of hepatoma cells via specific induction of NKG2D ligands by the histone deacetylase inhibitor sodium valproate" Can Res Jul. 15, 2005 vol. 65 No. 14 pp. 6321-6329.

Bai et al., Jan. 2010, Myricetin and quercetin are naturally-occuring co-substrates of cyclooxygenases in vivo, Prostaglandins Leukot Essent Fatty Acids, 82(1):1-11.

Baker et al., "A practical assay of lipoate in biologic fluids and liver in health and disease." Free Radic Biol Med. Sep. 1998; 25(4-5):473-479.

Befon et al., "Continuous Subcutaneous Octreotide in Gastrointestinal Cancer Patients: Pain Control and B-Endorphin Levels", Anticancer Research, 20:4039-4046 (2000) (abstract).

(56) References Cited

OTHER PUBLICATIONS

Bettuzzi et al., "Chemoprevention of human prostate cancer by oral administration of green tea catechins in volunteers with high-grade prostate intraepithelial neoplasia: a preliminary report from a one-year proof-of principle study," Cancer Res, Jan. 15, 2006, 66:1234-1240.
Bonnet et al., "A mitochondria-K+ channel axis is suppressed in cancer and its normalization promotes apoptosis and inhibits cancer growth." Cancer Cell. Jan. 2007;11(1):37-51.
Boyd, "Insulin and cancer." Integr Cancer Ther. Dec. 2003, 2(4):315-29.
Cai et al., "Restorative effect of quercetin on subcellular distribution of daunorubicin in multidrug resistant leukemia cell lines K562/ADM and HL-60/ADM." Department of Oncology, Shanghai No. 6 People's Hospital, Shanghai Jiaotong University, Shanghai 200233, P.R. China, Ai Zheng. Dec. 2004;23(12):1611-1615 (abstract).
Cairns et al., "Metabolic targeting of hypoxia and HIF1 in solid tumors can enhance cytotoxic chemotherapy." Proc Natl Acad Sci USA 104: 9445-9450.
Camacho et al., "Phase I dose escalation clinical trial of phenylbutyrate sodium administered twice daily to patients with advanced solid tumors." Invest New Drugs. Apr. 2007;25(2):131-8.
Cao et al., "Dichloroacetate (DCA) sensitizes both wild-type and over expressing Bcl-2 prostate cancer cells in vitro to radiation." Prostate 68: 1223-1231.
Carducci et al., "Phenylbutyrate induces apoptosis in human prostate cancer and is more potent than phenylacetate." Clin Cancer Res. Feb. 1996;2(2):379-87.
Castillo et al., "The effects of the bioflavonoid quercetin on squamous cell carcinoma of the head and neck origin." Am J Surg. 1989;158(4):351-5.
Chang et al., 2006, Reactive oxygen species production is involved in quercetin-induced apoptosis in human helatoma cells, Nutr Cancer, 55(2):201-209 (abstract).
Chen et al., "Quercetin and trichostatin A cooperatively kill human leukemia cells", Pharmazie 60:856-860 (2005).
Chen, L. et al., "Absorption, distribution, elimination of tea polyphenols in rats," Drug Metab Dispos, Sep. 1997, 25(9):1045-1050.
Choi et al., "Mechanism of alpha-lipoic acid-induced apoptosis of lung cancer cells." Ann N Y Acad Sci. Aug. 2009; 1171:149-55.
Cruz-Correa et al., Aug. 2006, Combination treatment with curcumin and quercetin of adenomas in familial adenomatous polyposis, Clinical Gasteroenterology and Hepatology, 4(8):1035-1038.
Daruwalla et al., "Hyperbaric Oxygen Therapy for Malignancy, A review" World Journal of Surgery, Nov. 2006.
Dashwood et al., "Dietary histone deacetylase inhibitors: From cells to mice to man" Semin Cancer Biol. Oct. 2007, 17(5):363-369.
Dell'Antone, "Inactivation of H+-vacuolar ATPase by the energy blocker 3-bromopyruvate, a new antitumour agent" Life Sci. Oct. 19, 2006;79(21):2049-55.
Dreher et al., "Role of oxygen free radicals in cancer development." Eur J Cancer. Jan. 1996;32A(1):30-38.
Du et al., "Dietary quercetin combining intratumoral doxorubicin injection synergistically induces rejection of established breast cancer in mice." Int Immunopharmacol. Jul. 2010;10(7):819-26.
Du et al., "Quercetin greatly improved therapeutic index of doxorubicin against 4T1 breast cancer by its opposing effects on HIF-1.alpha. in tumor and normal cells." Cancer Chemother Pharmacol. Jan. 2010;65(2):277-87.
Fang et al., "Dietary Polyphenols May Affect DNA Methylation", J. Nutr., Jan. 2007, vol. 137.
Farr, Charles, "The Therapeutic Use of Intravenous Hydrogen Peroxide", A Review, Experimental Evidence of Physiological Effect and Clinical Experience, Nov. 1986, 11 pp.
Ferry et al., "Phase I clinical trial of the flavonoid quercetin: pharmacokinetics and evidence for in vivo tyrosine kinase inhibition." Clin Cancer Res. Apr. 1996;2(4):659-68.
Ganapathy-Kanniappan et al., "3-Bromopyruvate induces endoplasmic reticulum stress, overcomes autophagy and causes apoptosis in human HCC cell lines." Anticancer Res. Mar. 2010;30(3):923-35.
Ganapathy-Kanniappan et al., "3-bromopyruvate: a new targeted antiglycolytic agent and a promise for cancer therapy." Curr Pharm Biotechnol. Aug. 2010;11(5):510-517.
Garcia-Roman et al., "VEGF secretion during hypoxia depends on free radicals-induced Fyn kinase activity in mast cells." BiochemBiophys Res Commun. Oct. 15, 2010;401(2):262-7.
Gilbert et al., "A phase I dose escalation and bioavailability study of oral sodium phenylbutyrate in patients with refractory solid tumor malignancies." Clinical Cancer Research Aug. 2001, 7:2292-2300.
Glaser KB, "HDAC inhibitors: Clinical update and mechanism-based potential", Biochem Pharmacol (2007).
Gore et al., Apr. 2002, Impact of prolonged infustions of the putative differentiating agent sodium phenylbutyrate on myelodysplastic syndromes and acute myeloid leukemia, Clinical Cancer Resarch, 8:963-970.
Gore, Steven D. et al., "Combined DNA Methyltransferase and Histone Deacetylase Inhibition in the Treatment of Myeloid Neoplasms," Cancer Res 2006; 66:6361-6369.
Gorospe et al., "Up-regulation and functional role of p21Waf1/Cip1 during growth arrest of human breast carcinoma MCF-7 cells by phenylacetate." Cell Growth Differ. Dec. 1996;7(12):1609-15.
Granowitz et al., "Hyperbaric Oxygen Inhibits benign and malignant human mammary epithelial cell proliferation" Anticancer Res. Nov.-Dec. 2005;25(6B):3833-42.
Grimberg et al., "Role of insulin-like growth factors and their binding proteins in growth control and carcinogenesis." J Cell Physiol. Apr. 2000;183(1):1-9.
Guevara-Aguirre et al., "Growth hormone receptor deficiency is associated with a major reduction in pro-aging signalling, cancer, and diabetes in humans." Sci Transl Med. Feb. 16, 2011;3(70):70ra13.
Han et al., "Effect of glycolytic inhibitors on proliferation and apoptosis of pancreatic cancer cell under hypoxic condition", Chinese Journal of General Surgery, Mar. 2009, 18(3):243-246.
Han, S. et al., "Differentiation of human neuroblatoma by phenylacetate is mediated by peroxisome proliferator-activated receptor gamma," Cancer Res., May 15, 2001, vol. 61:3998-4002.
Haroon et al., "Lung metastic load limitation with hyperbaric oxygen," Undersee Hyperb Med., Mar.-Apr. 2007, 34(2):83-90.
Hashemzae et al., Aug. 2017, Anticancer and apoptosis-inducing effects of quercetin in vitro and in vivo, Oncology Reports, 38(2):819-828.
Hastak, K. et al., "Role of p53 and NF-kappaB in epigallocatechin-3-gallate-induced apoptosis of LNCaP cells," Oncogene, Jul. 31, 2003, 22:4851-4859.
Hong, J. et al., "Stability, cellular update, biotransformation, and efflux of tea polyphenol (-)-epigallocatechin-3-gallate in HT-29 human colon adenocarcinoma cells," Cancer Res Dec. 15, 2002, 62:7251-7246.
Hsu et al., "Chemoresistance of lung cancer stemlike cells depends on activation of Hsp27." Cancer. Apr. 1, 2011;117(7):1516-28.
Iannitti et al., 2011, Clinical and experimental applications of sodium phenylbutyrate, Drugs, 11(3):227-249.
Ishikawa, A. et al., "Smoking, alcohol drinking, green tea consumption and the risk of esophageal cancer in Japanese men," J Epidemiol, Sep. 2006, 16(5):185-192.
Israel, M. et al., "The metabolic advantage of tumor cells," Mol Cancer, Jun. 7, 2011, 10:70.
Jia et al., "Histone hyperacetylation is involved in the quercetin-induced human leukemia cell death", Pharmazie, 2008, 63:379-383.
Jian, L. et al., "Protective effect of green tea against prostate cancer: a case-control study in southeast China," Int J Cancer, Jan. 1, 2004, 108:130-135.
Jung et al., "EGCG, a major component of green tea, inhibits tumour growth by inhibiting VEGF induction in human colon carcinoma cells," Br J Cancer, Mar. 23, 2001, vol. 84.
Jung et al., "Inhibition of tumour invasion and angiogenesis by epigallocatechin gallate (EGCG), a major component of green tea," Int J Exp Pathol, Dec. 2001, 82:309-316.
Kanadaswami et al., "The antitumor activities of flavonoids." In Vivo. Sep.-Oct. 2005;19(5):895-909.

(56) References Cited

OTHER PUBLICATIONS

Kaplan et al., "The Insulin-like Growth Factor Axis and Prostate Cancer: Lessons from the Transgenic Adenocarcinoma of Mouse Prostate (TRAMP) Model 1" Cancer Res May 5, 1999 59; 2203.

Kawada et al., "Insulin-like Growth Factor I Secreted from Prostate Stromal Cells Mediates Tumor-Stromal Cell Interactions of Prostate Cancer" Cancer Res Apr. 15, 2006 66:4419-4425.

Khan et al., "Cancer Chemoprevention Through Dietary Antioxidants: Progress and Promise", Antioxidants and Redox Signaling, vol. 10, No. 3, pp. 475-510, 2008.

Kim et al., "Inhibition of vascular endothelial growth factor induced angiogenesis suppresses tumour growth in vivo" Nature, Apr. 29, 1993, 362:841-844.

Ko et al., "Advanced cancers: eradication in all cases using 3-bromopyruvate therapy to deplete Atp." BiochemBiophys Res Commun. Nov. 5, 2004;324(1):269-275.

Ko et al., "Glucose catabolismin the rabbit VX2 tumor model for liver cancer: characterization and targeting hexokinase," Cancer Lett. Nov. 8, 2001;173(1):83-91.

Koshikawa et al., "Reactive oxygen species generating mitochondrial DNA mutation up regulates hypoxia inducible factor-1 alpha gene transcription via phosphatidylinositol 3-kinase-Akt/protein kinase C/ histone deacetylase pathway" J Biol Chem. Nov. 27, 2009, 284(48):33185-94.

Kurahashi, N. et al., "Green tea consumption and prostate cancer risk in Japanese men: a prospective study," Am J Epidemiol, Jan. 1, 2008, 167(1):71-77.

Kurmasheva et al., "The insulin-like growth factor-1 receptor-targeting antibody, CP-751,871, suppresses tumor-derived VEGF and synergizes with rapamycin in models of childhood sarcoma." Cancer Res. Oct. 1, 2009;69(19):7662-71.

Kurzrock et al., Mar. 72008, Targeted Cancer Therapy, Springer Science & Business Media, p. 362.

Lamson et al., "Antioxidants and Cancer III: Quercetin", Alternative Medicine Review, 5(3):196-208, 2000.

Lee et al., "Role of Bax in quercetin-induced apoptosis in human prostate cancer cells," Biochem Pharmacol. Jun. 15, 2008;75(12):2345-55.

Leroith et al., "The insulin-like growth factor system and cancer." Cancer Lett. Jun. 10, 2003;195(2): 127-37.

Levy, J et al., "Tyrosine protein kinase activity in the DMBA-induced rat mammary tumor: inhibition by quercetin," Biochem Biophys Res Commun., Sep. 28, 1984, 123(3):1227-1233.

Li et al., "Synergistic epigenetic reactivation of estrogen receptor-.alpha. (ER.alpha.) by combined green tea polyphenol and histone deacetylase inhibitor in ER.alpha.-negative breast cancer cells", Molecular Cancer, Biomed Central, Oct. 14, 2010, 9(1):274.

Lin et al., Oct. 1, 2009, A phase I dose-finding study of 5-azacytidine in combination with sodium phenylbutyrate in patients with refractory solid tumors, Clin Cancer Res, 15(19):6241-6249.

Liu et al., "Transcriptional upregulation of TGF-alpha by phenylacetate and phenylbutyrate is associated with differentiation of human melanoma cells." Cytokine. Jul. 1995;7(5):449-56.

Major et al., "The Role of Octreotide in the Management of Patients with Cancer", Ontario Cancer Center, Practice Guideline Report 12-7, Aug. 2004, 37 pp.

Maki, "Small is beautiful: insulin-like growth factors and their role in growth, development, and cancer." J Clin Oncol. Nov. 20, 2010;28(33):4985-95. Epub Oct. 25, 2010.

Martinet et al., "Interpreting clinical assays for histone deacetylase inhibitors." Cancer Manag Res. 2011; 3: 117-141.

Mathupala et al., "Hexokinase II: cancer's double-edged sword acting as both facilitator and gatekeeper of malignancy when bound to mitochondria." Oncogene. Aug. 7, 2006;25(34):4777-86.

Mehrabian, S., "The study of antioxidant and anticarcinogenic green tea and black tea," Pak J Biol Sci, Mar. 15, 2007, 10(6):989-991.

Meng, Studies on the differentiation of human hepatocarcinoma cell induced by historne deacetylase inhibitors and its mechanism, China Doctoral Dissertations Full-Test Database, p. E-072-39.

Michelakis, et al., "Dichloroacetate (DCA) as a potential metabolic-targeting therapy for cancer." Br J Cancer. Oct. 7, 2008;99(7):989-94.

Michelakis, et al., "Metabolic modulation of glioblastoma with dichloroacetate." Sci Transl Med. May 12, 2010;2(31):31ra34.

Millauer et al., "Glioblastoma growth inhibited in vivo by a dominant-negative Flk-1 mutant." Feb. 10, 1994, Nature, 367:576-579.

Mokrzycki "Anti-atherosclerotic efficacy of quercetin and sodium phenylbutyrate in rabbits", Ann Acad Med Stetin, 2000; 46:189-200 (abstract).

Molnar et al., "Antitumor activity of flavonoids on NK/Ly ascites tumor cells." Neoplasma. 1981;28(1):11-18.

Monneret et al., "Histone deacetylase inhibitors", European Journal of Medicinal Chemistry, Jan. 2005, 40(1):1-13.

Moussa et al., "Hyperbaric oxygen as an adjuvant to cisplatin containing regimen: a companion to a hard journey" Proc Am Soc Clin Oncol 21: 2002 (abstr 2806).

Mukhtar, H. et al., "Tea polyphenols: prevention of cancer and optimizing health," Am J Clin Nutr, Jun. 2000, vol. 71.

Mulholland et al., "Pre-clinical and clinical study of QC12, a water-soluble, pro-drug of quercetin," Annals Oncol Feb. 2001 vol. 12 No. 2 pp. 245-248.

Murray, Quercetin, in How to Prevent and Treat Cancer with Natural Medicine Penguin, Nov. 4, 2003, Health and Fitness, 5 pp.

Mydio et al., "Prostate Cancer: Science and Clinical Practice (Google eBook)", Academic Press, p. 523, Jul. 11, 2003.

Nagano, J. et al., "A prospective study of green tea consumption and cancer incidence, Hiroshima and Nagasaki (Japan),"-Cancer Causes Control, Aug. 2001, 12:501-508.

Nam, S. et al., "Ester bond-containing tea polyphenols potently inhibit proteasome activity in vitro and in vivo," J Biol Chern, Apr. 20, 2001, 276:13322-13330.

Navarro-Peran et al., "The antifolate activity of tea catechins," Cancer Res, Mar. 15, 2005, 65:2059-2064.

Niedzwiecki et al., Sep. 9, 2016, Anticancer efficacy of polyphenols and their combinations, Nutrients, 8(9):1-17.

Nihal et al., "Anti-melanoma effects of vorinostat in combination with polyphenolic antioxidant Epigallocatechin-3-Gallate (EGCG)", Pharmaceutical Research, 27(6):1103-1114, Jun. 2010.

Pedersen PL, "Transport ATPases into the year 2008: a brief overview related to types, structures, functions and roles in health and disease." J Bioenerg Biomembr. Dec. 2007;39(5-6):349-355.

Pedersen, PL, "The cancer cell's "power plants" as promising therapeutic targets: an overview." J Bioenerg Biomembr. Feb. 2007;39(1):1-12.

Pelicano et al., 2008, Glycolysis inhibition for anticancer treatment, Oncogene, 25:4633-4646.

Phuphanich et al., "Oral sodium phenylbutyrate in patients with recurrent malignant gliomas: a dose escalation and pharmacologic study." Neuro Oncol 2005; 7(2):177-182.

Pisters, KM et al., "Phase I trial of oral green tea extract in adult patients with solid tumors," J Clin Oncol, Mar. 15, 2001, 19(6):1830-1838.

Plate et al., "Vascular endothelial growth factor is a potent tumour angiogenesis factor in human gliomas in vivo." Oct. 29, 1992, Nature, 359:845-848.

Pollak et al., "Insulin, insulin-like growth factors, insulin resistance, and neoplasia[1-4]" Am J Clin Nutr. Sep. 2007;86(3):s820-2.

Pollak, "Insulin and insulin-like growth factor signalling in neoplasia." Nat Rev Cancer. Dec. 2008;8(12):915-928.

Pollak, Michael N. et al., "Insulin-like Growth Factors and Neoplasia," Nature Reviews: Cancer, Jul. 2004, 4:505-518.

Prophylaxis, dictionary definition, retrieved on Jun. 25, 2014 from: Vocabulary.com, 4 pp.

Prostate Cancer, Medline Plus, downloaded at http://www.nlm.nih.gov/medlineplus/print/ency/article/000380.htm, Nov. 9, 2009.

Qian et al., "Targeting tumor angiogenesis with histone deacetylase inhibitors: the hydroxamic acid derivative LBH589." Clin Cancer Res. Jan. 15, 2006;12(2):634-42.

Rokes et al., "Sorafenib Plus Valproic Acid for Infant Spinal Glioblastoma,"J Pediatr Hematol Concol, Aug. 2010, 32:511-514.

Roomi, MW. et al., "In vivo antitumor effect of ascorbic acid, lysine, proline and green tea extract on human prostate cancer PC-3

(56) References Cited

OTHER PUBLICATIONS xenografts in nude mice: evaluation of tumor growth and immunohistochemistry," In Vivo, Jan.-Feb. 2005, 19:179-184.
Sasabe et al., "Mechanism of HIF-1alpha-dependent suppression of hypoxia-induced apoptosis in squamous cell carcinoma cells." Cancer Sci. Jul. 2005;96(7):394-402.
Scatena et al., "Glycolytic enzyme inhibitors in cancer treatment", Expert Opinion on Investigational Drugs, Informa Healthcare, 17(10):1533-1545, Oct. 2008.
Schwartz et al., "A combination of alpha lipoic acid and calcium hydroxycitrate is efficient against mouse cancer models: preliminary results." Oncol Rep. May 2010;23(5):1407-16.
Selvendiran, "Oxygnation inhibits ovarian tumor growth by downregulating STAT3 and cyclin-D1 expression" Cancer biol Ther, Aug. 2010, 10(4):386-390.
Shabbeer et al., "Focus on Deacetylation for Therapeutic Benefit", IDRUGS, Current Drugs Ltd, Feb. 2005, 8(2):144-154.
Shanafelt, Tait D. et al., "Phase I Trial of Daily Oral Polyphenon E in Patients with Asymptomatic Rai Stage 0 to II Chronic Lymphocytic Leukemia," Journal of Clinical Oncology, Aug. 10, 2009, 27(23):3808-3814.
Shankar, S. et al., "EGCG inhibits growth, invasion, angiogenesis and metastasis of pancreatic cancer," Front Biosci, Jan. 1, 2008, 13:440-452.
Sharma et al., "Molecular pathways in the chemosensitization of cisplatin by quercetin in human head and neck," Cancer BiolTher (2005) 4(9): 949-55.
Shoskes et al., "Quercetin in Men with Category III Chronic Prostatitis: a Preliminary Prospective, Double-Blind, Placebo-Controlled Trial", Urology 54 (6), pp. 960-963, 1999.
Shweiki et al., "Vascular endothelial growth factor induced by hypoxia may mediate hypoxia-initiated angiogenesis." Oct. 29, 1992, Nature, 359:843-845.
Staedler et al., "Drug combinations with quercetin: doxorubicin plus quercetin in human breast cancer cells." Cancer Chemother Pharmacol. Nov. 2011;68(5):1161-1172.
Sun, CL. et al., "Green tea, black tea and breast cancer risk: a meta-analysis of epidemiological studies," Carcinogenesis, Jul. 2006, 27(7):1301-1309.
Sung et al., "Combination of cytotoxic-differentiation therapy with 5-fluorouracil and phenylbutyrate in patients with advanced colorectal cancer." Anticancer Res. Mar.-Apr. 2007;27(2):995-1001.
Suzuki, Y. et al., "Green tea and the risk of breast cancer: pooled analysis of two prospective studies in Japan," Br J Cancer, Apr. 5, 2004, 90:1361-1363.
Takenouchi et al., "Studies on the metabolism of thioctic acid in skin diseases 2. Loading test of thioctic acid in various skin diseases" The Journal of Vitaminology 8, 99-114 (1962).
Tang et al., "The dietary bioflavonoid quercetin synergizes with epigallocathechin gallate (EGCG) to inhibit prostate cancer stem cell characteristics, invasion, migration and epithelial-mesenchymal transition." J Mol Signal. Aug. 18, 2010;5:14.
Tosetti, F., "Angioprevention: angiogenesis is a common and key target for cancer chemopreventive agents," FASEB, J Jan. 2002, vol. 16, 14 pp.
Troy et al., Remington: The Science and Practice of Pharmacy, p. 838, 2006.
Vaupel, "The Role of Hypoxia-Induced Factors in Tumor Progression" Oncologist. 2004;9 Suppl 5:10-17.
Wada et al, "A study on the metabolism of lipoic acid and lipoamide" The Journal of Vitaminology 7, 237-242 (1960).
Wang et al., "Co-treatment with quercetin to enhance the chemopreventive effect of green tea in prostate cancer", FASEB J., Apr. 2010, Meeting Abstract Supplement. Abstract.
Wang et al., Mar. 27, 2012, Quercetin increased the antiproliferative activity of green tea polyphenol (-)-epigallocatechin gallata in prostate cancer cells, Nutrition and Cancer, 64(4):580-587.
Wang, Studies on the apoptosis of NB4 cells induced by hsitone deacetylase inhibitors in combination with ATRA and As203 and its mechanism, China Master's Dissertations Full-Test Database, p. 3072-35.
Wardell et al., "Glucose metabolism as a target of histone deacetylase inhibitors." Mol Endocrinol. Mar. 2009;23(3):388-401.
Wenzel et al., "Alpha-Lipoic acid induces apoptosis in human colon cancer cells by increasing mitochondrial respiration with a concomitant O2-*-generation" Apoptosis. Mar. 2005;10(2):359-368.
Wong et al., "Dichloroacetate induces apoptosis in endometrial cancer cells" Gynecol Oncol 109: 394-402.
Wu, AH. et al., "Green tea and risk of breast cancer in Asian Americans," Int J cancer, Sep. 10, 2003, 106:574-579.
Yang et al., "Cancer prevention by tea: animal studies, molecular mechanisms and human relevance," Nat Rev Cancer, Jun. 2009, 9:429-439.
Yang, CS., et al., "Inhibition of carcinogenesis by tea," Annu RevPharmacol Toxicol, 2002, 42:25-54.
Yang, Gong et al., "Prospective Cohort Study of Green Tea Consumption and Colorectal Cancer Risk in Women," Cancer Epidemiol Biomarkers Prev, Jun. 2007, 16:1219-1223.
Yoon, Joo-Heon et al., "Molecular Targets of Dietary Polyphenols with Anti-inflammatory Properties," Yonsei Med J., Oct. 31, 2005, 46(5):585-596.
Zhang et al., "Sodium 4-phenylbutyrate induces apoptosis of human lung carcinoma cells through activating JNK pathway." J Cell Biochem. Nov. 1, 2004;93(4):819-29.
Zhou et al., "Dietary polyphenol quercetin targets pancreatic cancer stem cells." Int J Oncol. Sep. 2010;37(3):551-561.
Baldwin et a l., Oct. 1, 2016, Nanoformulation of the PARP inhibitor olaparib enables radiosensitization of a radiation-resistant prostate cancer mode, International J. of Radiation Oncology, Biology, Physics, Poster viewing abstract, 96(2S-Supplement 2016):E595.

* cited by examiner

| Alteration | % cDNA | cDNA Amplification |
|---|---|---|
| CDK6 | AMP | +++ |
| MET | AMP | ++ |
| MYC | AMP | ++ |
| PIK3CA | AMP | + |
| KRAS | AMP | + |
| FGFR2 | AMP | + |
| CDK4 | AMP | + |
| CCND2 | AMP | + |

FIG. 31

| Alteration | | | % cDNA or Amplification |
|---|---|---|---|
| Relevant for Therapy Selection | | | |
| APC | | E1309fs | 38.3 |
| | | R232* | 27.8 |
| KRAS | | G12V | 33.6 |
| PIK3CA | | N1044K | 13.9 |
| EGFR | | AMP | ++ |
| BRAF | | AMP | + |

FIG. 43

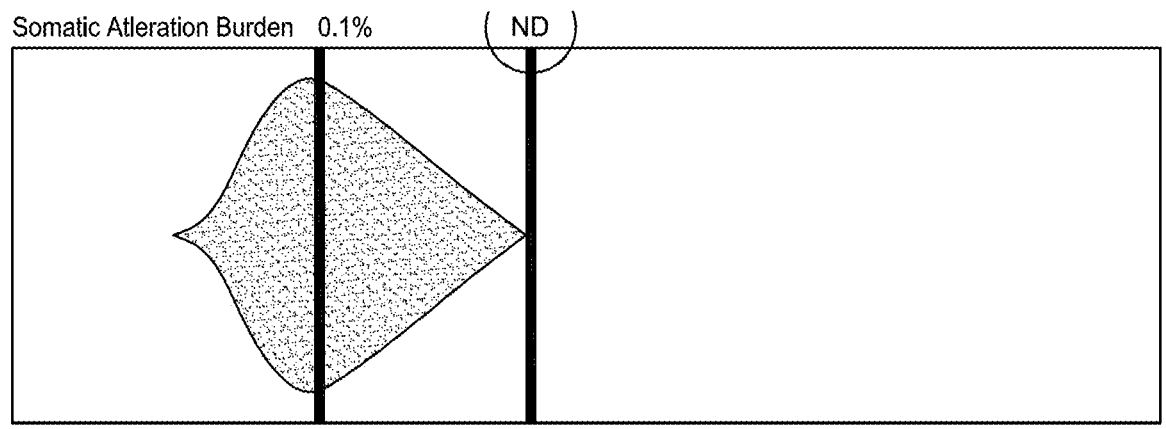
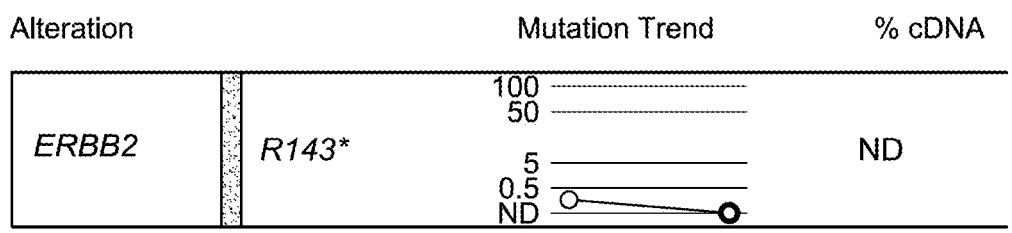
FIG. 46

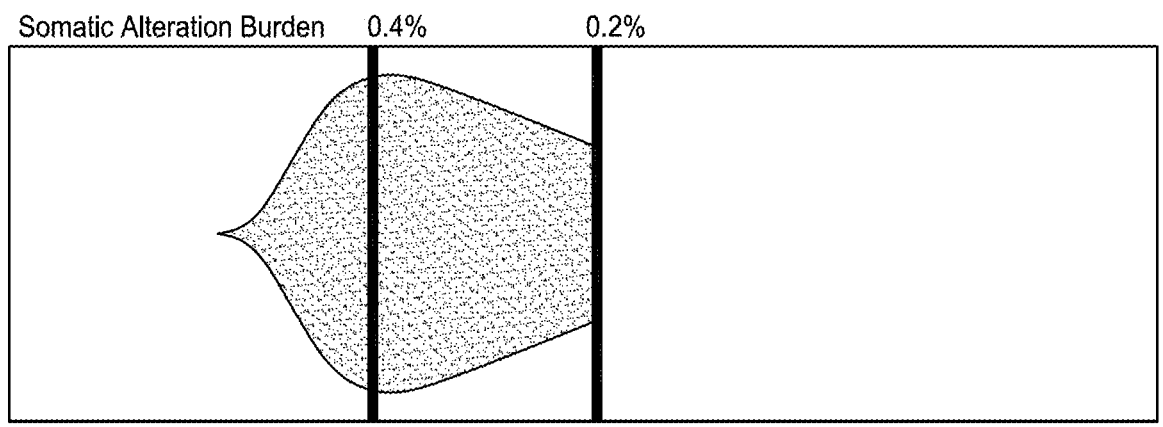
FIG. 47

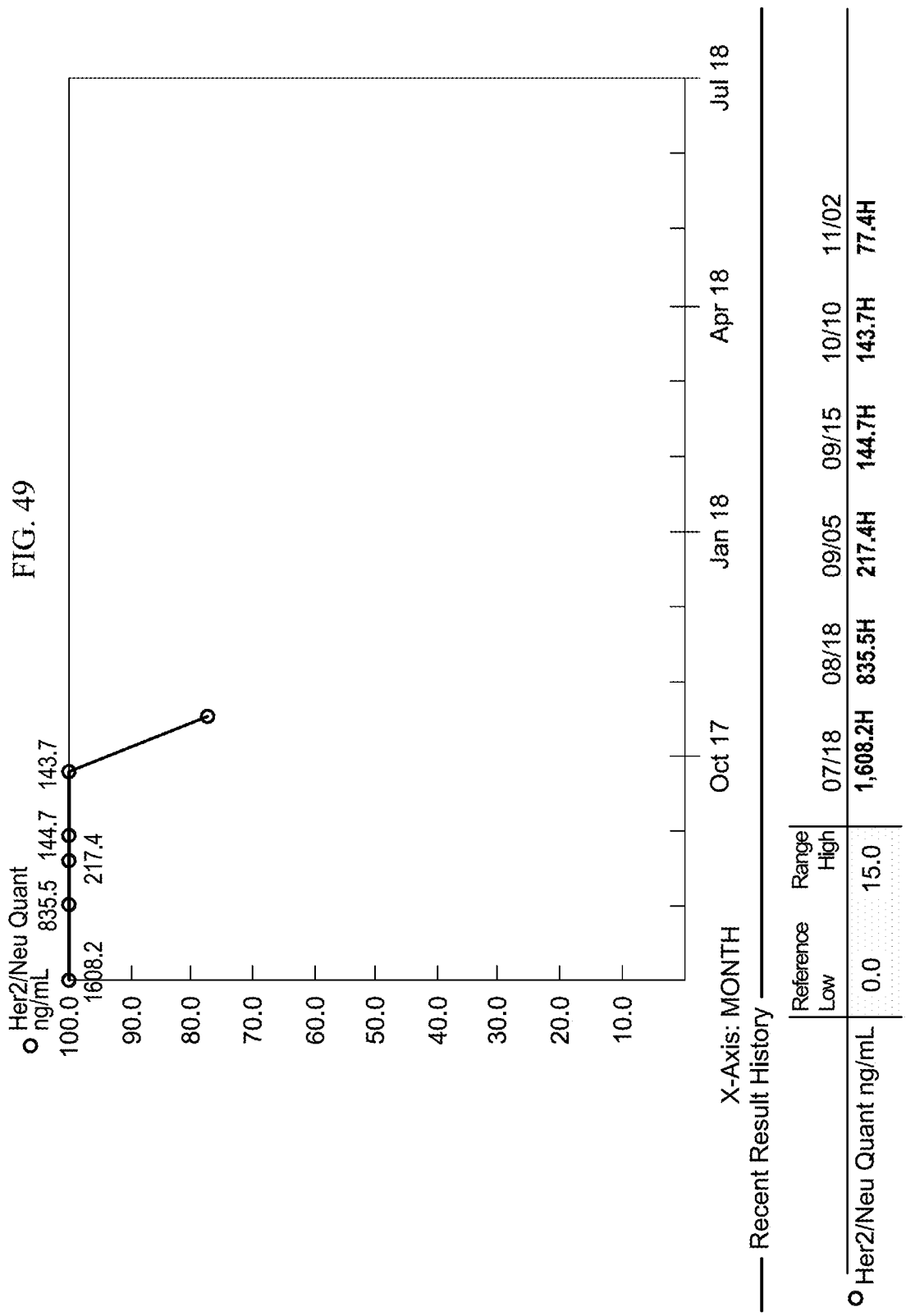

COMPOSITIONS, METHODS, SYSTEMS AND/OR KITS FOR PREVENTING AND/OR TREATING NEOPLASMS

PRIORITY AND CROSS REFERENCE TO RELATED APPLICATIONS

This application is the U.S. National Stage Application under 35 U.S.C. § 371 of International Application No. PCT/US. 2018/061390, filed Nov. 15, 2018, designating the U.S., and published as WO 2019/099750 on May 23, 2019, which claims the benefit of U.S. Provisional Application No. 62,588,188, filed on Nov. 17, 2017, which is hereby incorporated by reference in its entirety.

BACKGROUND

Field

The present disclosure is generally related to compositions, methods, systems and/or kits comprising, consisting of, or consisting essentially of, one or more anti-cancer response modulators in combination with one or more anti-cancer agents for preventing and/or treating neoplasms. Certain embodiments of the present disclosure are related to compositions, methods, systems and/or kits comprising, consisting of, or consisting essentially of, one or more anti-cancer response modulators in combination with one or more anti-cancer agents for preventing and/or treating neoplasms that are resistant to the one or more anti-cancer agents.

Description of the Related Art

Until the late 1990s nearly all drugs used in cancer treatment (with the exception of hormone treatments) worked by killing cells that were in the process of replicating their DNA and dividing to form 2 new cells. These chemotherapy drugs also killed some normal cells but had a greater effect on cancer cell.

Although targeted drugs have been introduced to oncology therapeutics aiming to reduce the toxicity of traditional cytotoxic therapies, and improving patients response, the limitation in their application has been an area of disappointment leading to an extensive effort on understanding the mechanism of failure, including resistance and secondary mutations on the actionable target.

SUMMARY

In some embodiments, a pharmaceutical composition for prophylaxis, treatment or both of a neoplasm is provided comprising, consisting of, or consisting essentially of, at least one anti-cancer agent, and a first anti-cancer response modulator, wherein the first anti-cancer response modulator is selected form the group consisting of quercetin, sodium phenyl butyrate (SPB) and epigallocatechin-3-gallate (EGCG). In some embodiments, the pharmaceutical composition further comprises, consists of, or consists essentially of, a second anti-cancer response modulator selected form the group consisting of quercetin, SPB and EGCG. In some embodiments, the pharmaceutical composition further comprises, consists of, or consists essentially of, a third anti-cancer response modulator selected form the group consisting of quercetin, SPB and EGCG. In some embodiments of the pharmaceutical composition, the first anti-cancer response modulator is quercetin. In some embodiments of the pharmaceutical composition, the first anti-cancer response modulator is SPB. In some embodiments of the pharmaceutical composition, the first anti-cancer response modulator is EGCG. In some embodiments of the pharmaceutical composition, the second anti-cancer response modulator is quercetin. In some embodiments of the pharmaceutical composition, the second anti-cancer response modulator is SPB. In some embodiments of the pharmaceutical composition, the second anti-cancer response modulator is EGCG. In some embodiments of the pharmaceutical composition, the first, second and third anti-cancer response modulators are quercetin, SPB and EGCG. In some embodiments of the pharmaceutical composition, at least one anti-cancer agent is selected from the group consisting of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) and Trametinib (Mekinist). In some embodiments of the pharmaceutical composition, at least a portion of the pharmaceutical composition is formulated for IV administration or oral administration.

In some embodiments of the pharmaceutical composition, the amount of the anti-cancer agent selected from the group consisting of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) and Trametinib (Mekinist) is about 0.01 mg/day, mg/kg, or mg/m$^2$ and about 1000 mg/day, mg/kg, or mg/m$^2$. In some embodiments of the pharmaceutical composition, the amount of quercetin is 0.1 g to 2.5 g. In some embodiments of the pharmaceutical composition, the quercetin is in solution at a concentration of 10 mg/ml to 500 mg/ml. In some embodiments of the pharmaceutical composition, the amount of SPB is 0.1 g to 40 g. In some embodiments of the pharmaceutical composition, the SPB is in solution at a concentration of 50 mg/ml to 500 mg/ml. In some embodiments of the pharmaceutical composition, the amount of EGCG is 0.1 g to 1.5 g. In some embodiments of the pharmaceutical composition, the EGCG is in solution at a concentration of 5 mg/ml to 50 mg/ml.

In some embodiments of the pharmaceutical composition, the anti-cancer agent and at least one anti-cancer response modulator are in a single dosage form for co-administration. In some embodiments of the pharmaceutical composition, the anti-cancer agent and at least one anti-cancer response modulator are in a single dosage form suitable for IV administration. In some embodiments of the pharmaceutical composition, the anti-cancer agent and at least one anti-cancer response modulator are in a single dosage form suitable for oral administration. In some embodiments of the pharmaceutical composition, the anti-cancer agent and at least one anti-cancer response modulator are in a separate dosage forms. In some embodiments of the pharmaceutical composition, the anti-cancer agent and at least one anti-cancer response modulator are each in dosage forms suitable for IV administration. In some embodiments of the pharmaceutical composition, the anti-cancer agent and at least one anti-cancer response modulator are each in dosage forms suitable for oral administration. In some embodiments of the pharmaceutical composition, either the anti-cancer agent or the at least one anti-cancer response modulator is in a dosage form suitable for oral administration and the other is in a dosage form for IV administration.

In some embodiments, the neoplasm is one or more of breast adenocarcinoma, pancreatic adenocarcinoma, lung carcinoma, prostate cancer, hormone refractory prostate cancer, solid tumor malignancies, colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, bladder cancer, hematological malignancies, squamous cell carcinomas, breast cancer, astrocytomas, pilocytic astrocytoma, diffuse astrocytoma, anaplastic astrocytoma, and brain stem gliomas, glioblastomas, glioblastoma multiforme, meningioma, gliomas, ependymomas, oligodendrogliomas, and mixed gliomas, brain tumors, pituitary tumors, craniopharyngiomas, germ cell tumors, pineal region tumors, medulloblastomas, and primary CNS lymphomas.

In some embodiments, a kit for prophylaxis, treatment or both of a neoplasm is provided wherein the kit comprises, consists of, or consists essentially of, a pharmaceutical composition, wherein the pharmaceutical composition is in a single container. In some embodiments of the kit, each of the at least one anti-cancer agent and the one or more modulators are contained in a single container in a single dosage form. In some embodiments of the kit, each of the at least one anti-cancer agent and the one or more modulators are contained in separate sub-containers.

In some embodiments, use of any of the pharmaceutical compositions or kits disclosed herein for treatment, prevention or both of a neoplasm in a subject in need thereof is provided. In some embodiments, the neoplasm is likely to develop resistance, develops resistance, and/or is already resistant to the at least one anti-cancer agent. In some embodiments, the neoplasm is likely to develop resistance, develops resistance, and/or is already resistant to the one or more modulators.

In some embodiments, a method of prevention, treatment or both of a neoplasm is provided comprising, consisting of, or consisting essentially of, administering any of the compositions disclosed herein to a patient in need thereof. In some embodiments of the method, the pharmaceutical composition is administered to the subject IV, orally or both. In some embodiments of the method, the effect on the neoplasm is an improved result as compared to an effect on the neoplasm of either the at least one anti-cancer agent alone or the one or more modulators alone. In some embodiments of the method, the anti-cancer agent selected from the group consisting of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) and Trametinib (Mekinist) is administered at a dose of about 0.01 mg/day, mg/kg, or mg/m$^2$ and about 1000 mg/day, mg/kg, or mg/m$^2$. In some embodiments of the method, the quercetin is administered at a dose of 0.1 g to 2.5 g. In some embodiments of the method, the SPB is administered at a dose of 0.1 g to 40 g. In some embodiments of the method, the EGCG is administered at a dose is 0.1 g to 1.5 g.

In some embodiments, any of the compositions, kits, uses or methods disclosed herein induces apoptosis in vitro in at least one cancer cell line. In some embodiments, the induction of apoptosis by the composition is additive as compared to the induction of apoptosis of each of the anti-cancer agents and at least one modulators alone. In some embodiments, the induction of apoptosis by the composition is synergistic as compared to the induction of apoptosis of each of the anti-cancer agents and at least one modulator alone.

In some embodiments, a pharmaceutical composition, kit, use and/or method is provided, wherein the modulator is in a nanoparticle formulation. In some embodiments, a pharmaceutical composition, kit, use and/or method is provided, the anti-cancer agent is in a nanoparticle formulation. In some embodiments, a pharmaceutical composition, kit, use and/or method is provided, wherein both the modulator and the anti-cancer agent are in a nanoparticle formulation.

In some embodiments, the composition, kit, use and/or method comprises, consists of, or consists essentially of Rituximab (Rituxan) as the at least one anti-cancer agent. In some embodiments, the composition, kit, use and/or method comprises, consists of, or consists essentially of, Ibrutinib (Imbruvica) as the at least one anti-cancer agent. In some embodiments, the composition, kit, use and/or method comprises, consists of, or consists essentially of, Cetuximab (Erbitux) as the at least one anti-cancer agent. In some embodiments, the composition, kit, use and/or method comprises, consists of, or consists essentially of, Crizotinib (Xalkori) as the at least one anti-cancer agent. In some embodiments, the composition, kit, use and/or method comprises, consists of, or consists essentially of, Ceritinib (Zykadia) as the at least one anti-cancer agent. In some embodiments, the composition, kit, use and/or method comprises, consists of, or consists essentially of, Trastuzumab (Herceptin) as the at least one anti-cancer agent. In some embodiments, the composition, kit, use and/or method comprises, consists of, or consists essentially of, Everolimus (Afinitor) as the at least one anti-cancer agent. In some embodiments, the composition, kit, use and/or method comprises, consists of, or consists essentially of, Afatinib (Gilotrif) as the at least one anti-cancer agent. In some embodiments, the composition, kit, use and/or method comprises, consists of, or consists essentially of, Bevacizumab (Avastin) as the at least one anti-cancer agent. In some embodiments, the composition, kit, use and/or method comprises, consists of, or consists essentially of, Trametinib (Mekinist) as the at least one anti-cancer agent. In some embodiments, the composition, kit, use and/or method comprises, consists of, or consists essentially of, Trametinib (Mekinist)+Temodar as the at least one anti-cancer agent.

BRIEF DESCRIPTION OF THE DRAWINGS

FIG. 31 shows an embodiment of a summary of somatic alterations (See, Example 26).

FIG. 43 shows an embodiment of a summary of somatic alterations (See, Example 37).

FIG. 46 shows an embodiment of a Guardant360 Tumor Response Map and an embodiment of a summary of somatic alterations (See, Example 38).

FIG. 47 shows an embodiment of a Guardant360 Tumor Response Map and an embodiment of a summary of somatic alterations (See, Example 40).

FIG. 49 shows an embodiment of a graph of serum Her2 levels before and after treatment (See, Example 17).

DETAILED DESCRIPTION

Figure 1:
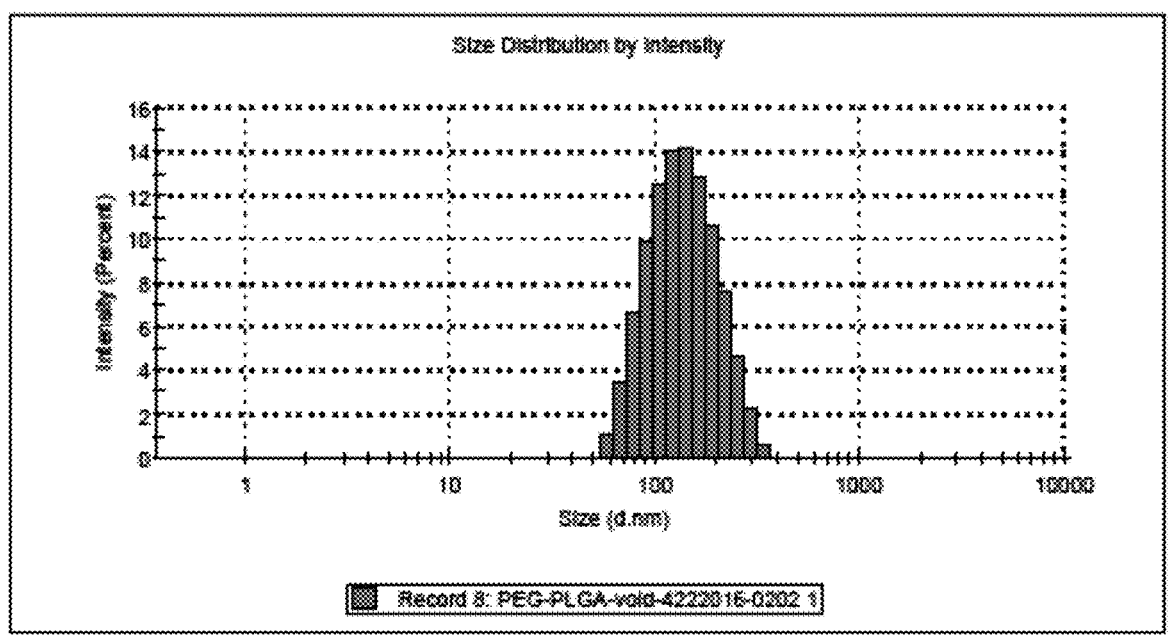
FIG. 1 shows size determination of an embodiment of Void-PLGA-PEG-NPs by Dynamic Light Scattering (DLS) (See, Example 1).
Figure 2:
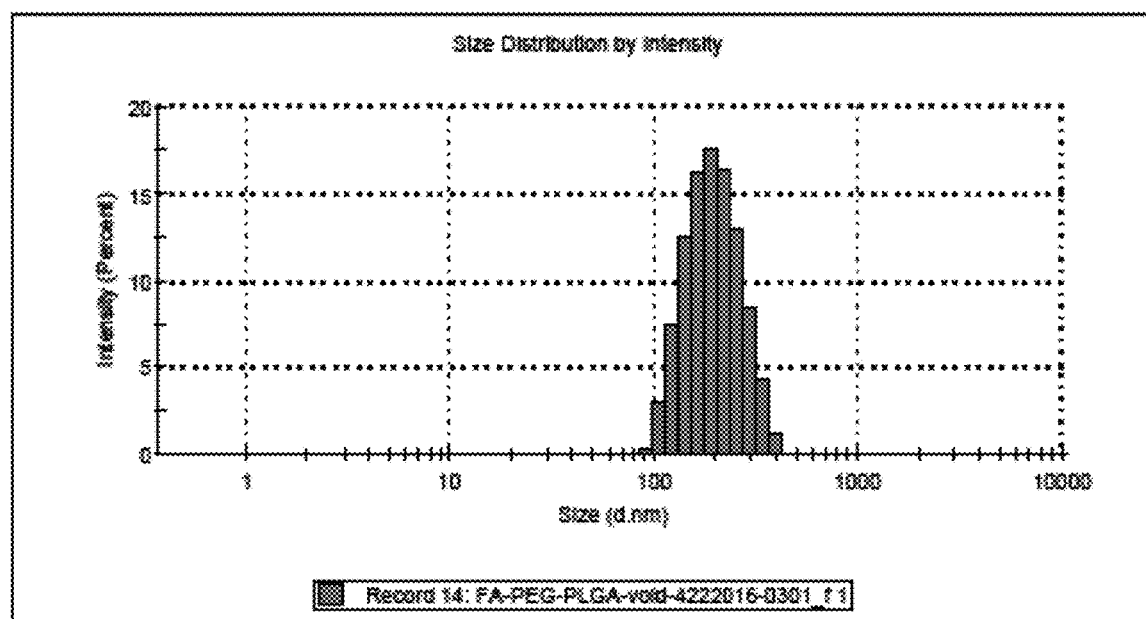
FIG. 2 shows size determination of an embodiment of FA-PLGA-PEG-NPs (Folic Acid conjugated PLGA-PEG-NPs) by DLS (See, Example 1).
Figure 3:
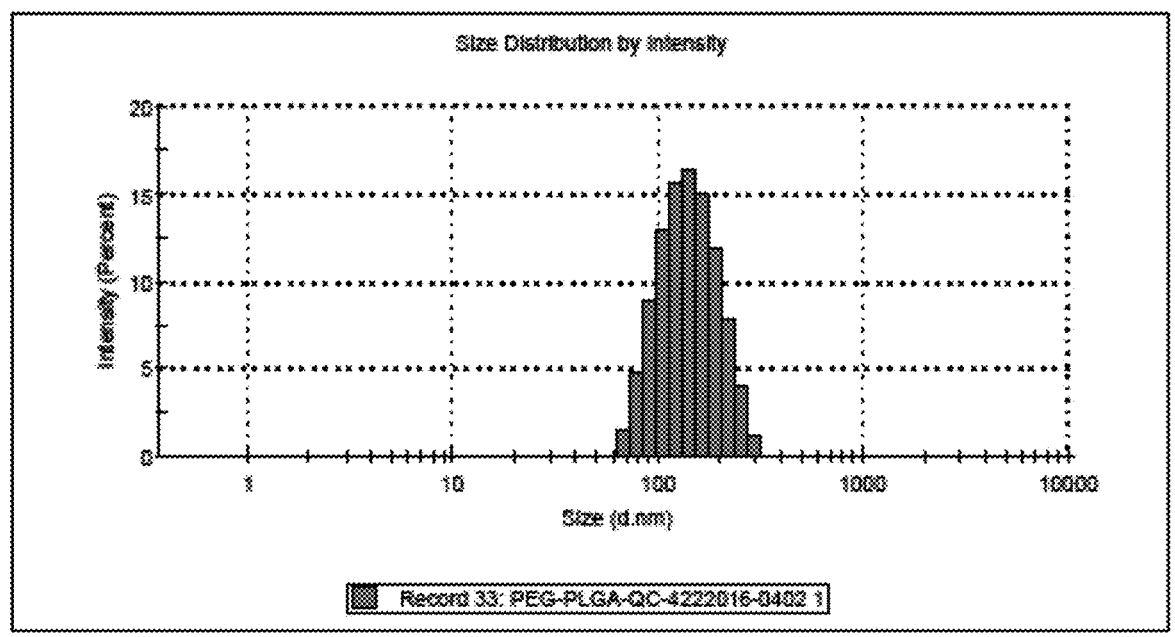
FIG. 3 shows size determination of an embodiment of PLGA-PEG-QC NPS (PLGA-PEG NPS encapsulating quercetin) by DLS (See, Example 1).
Figure 4:
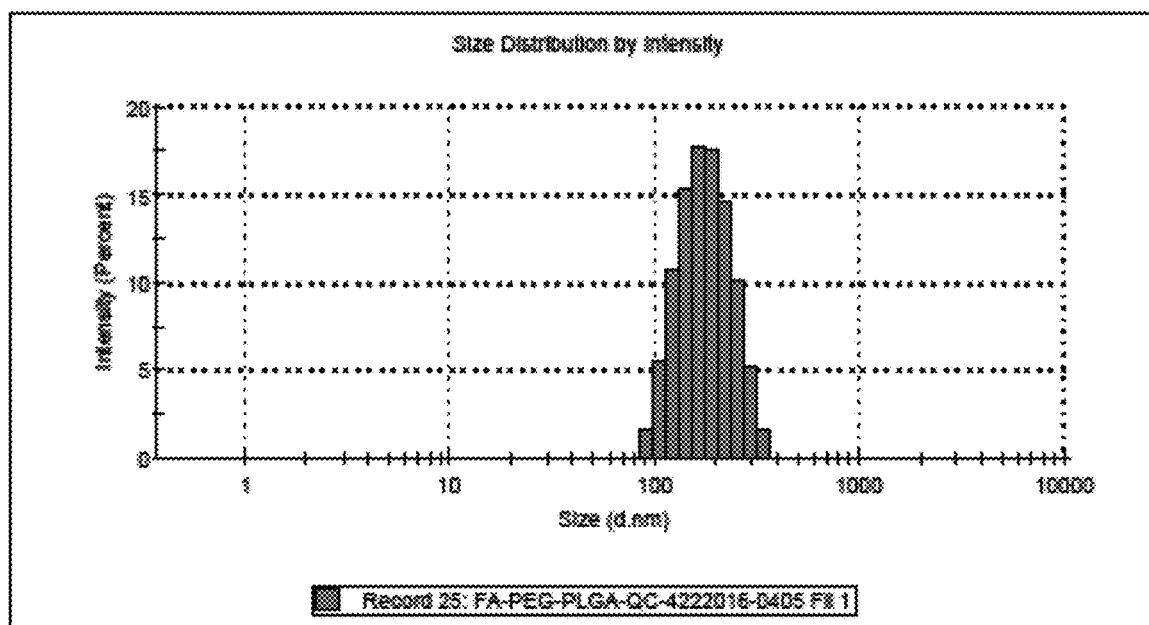
FIG. 4 shows size determination of an embodiment of FA-PLGA-PEG-QC NPS (Folic acid conjugated (PLGAPEG NPS encapsulating quercetin) by DLS (See, Example 1).
Figure 5:
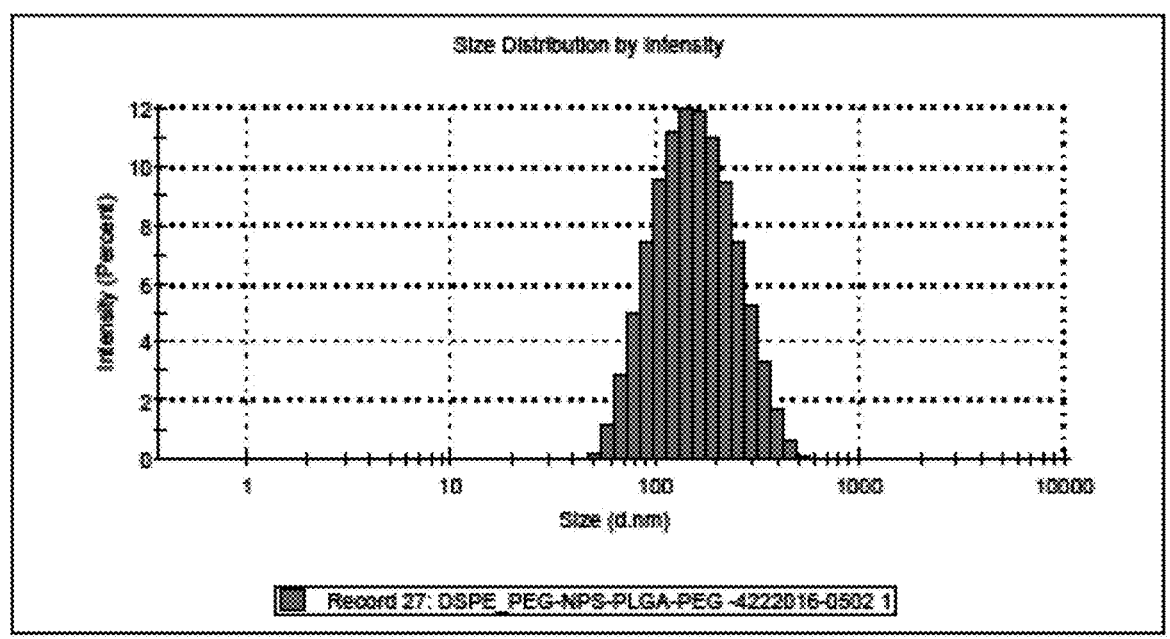
FIG. 5 shows size determination of an embodiment of DSPE-PEG-NPS (Void-DSPE-PEG/PLGA-PEG-NPS) by DLS
Figure 6:
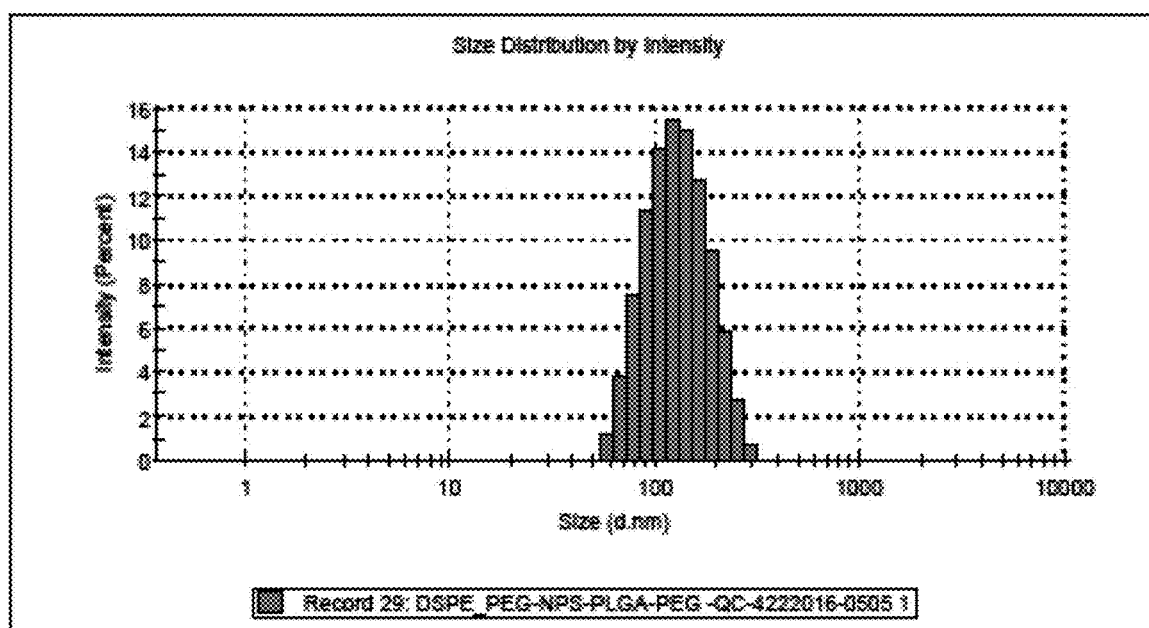
FIG. 6 shows size determination of an embodiment of DSPE-PEG-QC-NPS (DSPE-PEG/PLGA-PEG-NPS encapsulating quercetin) by DLS (See, Example 1).
Figure 7:
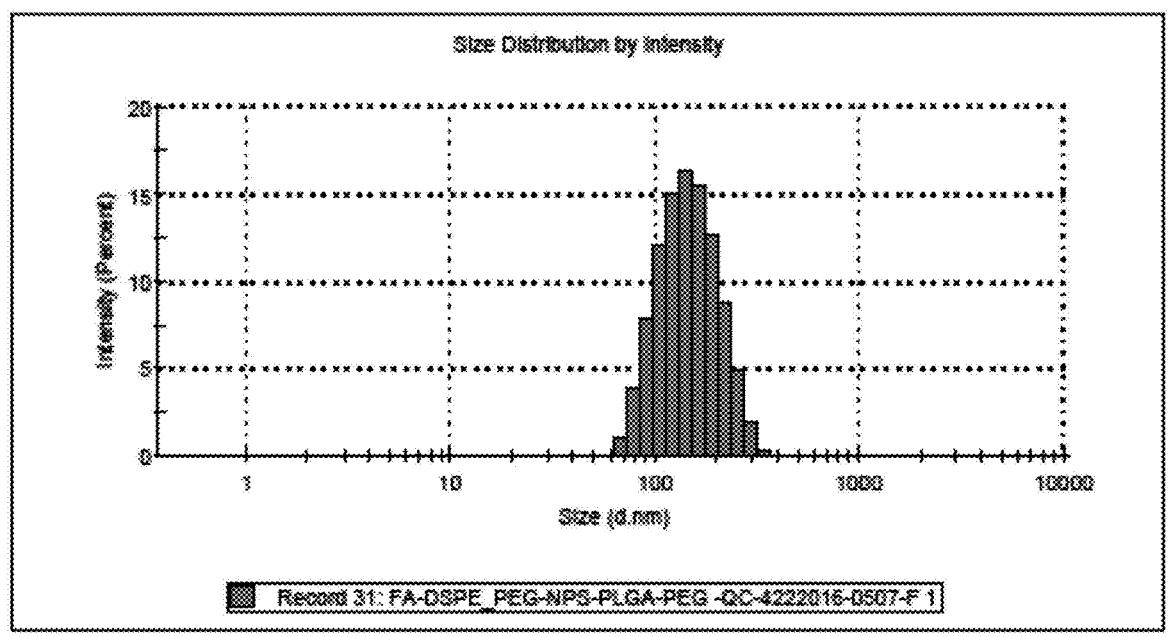
FIG. 7 shows size determination of an embodiment of FA-DSPE-PEG-QC-NPS (Folic acid conjugated DSPEPEG/PLGA-PEG-NPS encapsulating quercetin) by DLS (See, Example 1).

Statistics show that deaths caused by advanced cancers of various types have not significantly changed since a decade ago. Indeed, in some cases (e.g., lung cancer) the death rate is rising, especially among women. Even as novel anti-cancer agents are introduced to the market for advanced stages of the disease, patient survival rates have remained essentially unchanged. Moreover, potential toxicity of many novel anti-cancer agents can be a devastating factor both for the clinician and the patient. Additionally, the development of resistance to anti-cancer agents is another cause for concern.

Targeted therapies work by influencing the processes that control growth, division, and spread of cancer cells, as well as the signals that cause cancer cells to die naturally (the way normal cells do when they are damaged or old). Targeted therapies work in several ways including enhancing apoptosis, angiogenesis, and growth signal inhibition. Some examples drug for targeted therapies include trastuzumab (Herceptin), gefitinib (Iressa), imatinib (Gleevec), and cetuximab (Erbitux). Additional description about targeted therapies can be found under the URL mycancergenome.org/content/molecular-medicine/overview-of-targeted-therapies-for-cancer/, which is hereby incorporated by reference in its entirety.

Tumor cells are extremely adaptive and responsive. For example, when patients are treated with kinase inhibitors there is often a strong initial arrest of tumor growth. However, invariably the tumors become resistant.

Targeted therapies (e.g., trametinib) are designed to block specific signaling pathways that are overactive or abnormal in cancer. However, cancer cells can change the expression of genes in alternative protein pathways in order to skirt around the blocked pathway, allowing them to restart uncontrolled cell growth. In this regard, significant progress has been made in terms of identification of mechanisms of resistance, For example in response to treatment with trametinib, cells turn on new genes that allow them to overcome the action of trematinib.

As a result, efforts to enhance clinical response are highly limited as there are very few available drugs to provide clinical advantages and applications in many types of cancer. Without being bound by any theory, it is believed that the limited number of available drugs will continue to pose a barrier for the treatment of many types of cancer.

There are two categories of targeted therapies when it comes to such barrier. One are the drugs that actually have clinical benefit in certain type of tumors, but the clinical advantage is limited due to acquired resistance or the cancer mutations, and second the drugs that have completely failed the phase III trials and do not have any clinical advantage to begin with.

Newer drugs drug for targeted therapies that have failed to result in any meaningful survival benefit in phase III trials include: Mekinist, failed as first line therapy for wild BRAF melanoma and mutated BRAF colorectal cancer by Novartis; Veliparib, failed for triple negative breast cancer and NSCLC; Ramicurimab, failed as first line therapy for gastric and NCLCA; Iniparib (by Sanofi), failed for ovarian and triple negative breast cancer; Avastin, failed as first line therapy for colorectal cancer, breast cancer, prostate cancer and stomach cancer, first line glioblastoma; Rociletinib, failed for NSCLC-EGFR T790 C inhibitor; Ziv-aflibercept approved for colorectal cancer, failed for NSCLC; Figitumumab (by Pfizer), failed for NSCLC (IGF-1 inhibitor); Sorafenib (MTKI), failed for NSCLC); Algenpantucel, failed for pancreatic cancer; Tivantinib (For HCC)/met inhibitor; Selumetinib (multi-target inhibitor including MEK and MAPK), approved for thyroid CA, failed for NSCLC; ASP8273 (by AStellas), failed for NSCLC; Vandetanib, failed for NSCLC.

Examples of drugs that have approved indications but the clinical advantages are limited include: Afatinib/Gilotrif, approved for metastatic SC lung CA, or EGFR positive NSCLC) by Boehringer Ingelheim; Herceptin (by Roche), approved HER2 Positive Metastatic Breast Cancer and HER2 Positive Gastric Cancer); Afinitor (Everolimus) (by Novartis), approved for neuroendocrine tumors, advanced renal cancer, Her2-/ER+, breast cancer; Everolimus is also available from Biocon with the brand name Evertor; Mekinist (by Novartis), approved for metastatic mutated BRAF malignant melanoma, along with BRAF inhibitor; Denosumab (Xgeva), a RANK ligand (RANKL) inhibitor indicated for prevention of skeletal-related events in patients with bone metastases from solid tumors; Crizotonib (Xalkori), approved for NSCLC with ALK/ROS mutations; Erlotonib (Tarceva), approved for NSCLC with EGFR mutations; Rituximab (C20 antibody), approved for CLL, Non-Hodgkin's Lymphoma; Velcade (Bortezomib), a protoseome inhibitor approved for multiple myeloma and mantle cell lymphoma; Ibrutinib (Impruvica), a BTK inhibitor approved for multiple myeloma and mantle cell lymphoma and Waldenstrom Macroglobulinemia.

Provided herein are compositions, methods, systems and/or kits comprising, consisting of, or consisting essentially of, one or more anti-cancer response modulators in combination with one or more anti-cancer agents for preventing and/or treating neoplasms are provided. In some embodiments, compositions, methods, systems and/or kits comprising, consisting of, or consisting essentially of, one or more anti-cancer response modulators in combination with one or more anti-cancer agents for preventing and/or treating neoplasms that are resistant to the one or more anti-cancer agents are provided. In some embodiments, the one or more anti-cancer agents is Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist). In some embodiments, the one or more anti-cancer agents is Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination. In some embodiments, neoplasms are one or more types of brain cancer.

Also provided herein are embodiments of case studies based on novel combinatorial therapies that provide superior clinical results in a variety of tumor types. In some embodiments, the combinatorial therapies are based on combinations of one or more modulators provided herein and one or more drugs for targeted therapies provided herein.

Patient Population

Provided herein are embodiments of compositions, methods, systems and/or kits useful for preventing and/or treating one or more neoplasms in patients. A neoplasm could be a tumor, a cancer, any new and/or abnormal growth resembling a tumor and/or cancer, or any combination thereof.

In some embodiments, a patient is administered one or more anti-cancer agents to prevent and/or treat a neoplasm. In some embodiments, the patient is naïve and never been previously treated with one or more anti-cancer agents. In some cases, the patient may initially respond to the one or more anti-cancer agents resulting in an initial regression of the neoplasm. However, the neoplasm may become resistant to the one or more anti-cancer agents resulting in a relapse. In some embodiments, relapse may also occur due to discontinuing treatment, in which case the relapsed neoplasm may or may not be sensitive to the one or more anti-cancer agents previously administered. Therefore, the patient may either be re-administered the same anti-cancer agent or a different anti-cancer agent. In some embodiments, the patient is initially treated with a first anti-cancer agent, but is subsequently treated with a different second anti-cancer agent. This may be due to several reasons including, but not limited to, development of resistance to the first anti-cancer agent, adverse effects of the first anti-cancer agent, etc.

Therefore, the embodiments of the compositions, methods, systems and/or kits provided herein are desirable for patients who are initially responsive but will eventually become non-responsive to one or more anti-cancer agents, or in patients who were initially responsive but have now become non-responsive to one or more anti-cancer agents. The embodiments are also desirable for patients who are non-responsive because they have a neoplasm that is resistant to one or more anti-cancer agents.

In some embodiments, the patient is a male or a female. A patient is typically human but animals other than human are also contemplated. Non-limiting examples of the animals other than human include without limitation domestic animals, pets, experimental animals, and/or commercially important animals.

Tumor and/or Cancer Types

Disclosed herein are non-limiting examples of neoplasms, which could be a tumor, a cancer, any new and/or abnormal growth resembling a tumor and/or cancer, or any combination thereof. In some embodiments, the neoplasm is a breast carcinoma or a breast adenocarcinoma, or any neoplasm associated with breast. In some embodiments, neoplasm is a non-small cell lung carcinoma or lung adenocarcinoma, or any neoplasm associated with lung. In some embodiments, the neoplasm is a uterine sarcoma, or any neoplasm associated with uterus. In some embodiments, the neoplasm is a pancreatic adenocarcinoma, or any neoplasm associated with pancreas. In some embodiments, the neoplasm is a malignant melanoma, or any neoplasm associated with skin.

In some embodiments, the neoplasm is likely to become resistant and/or is already resistant to one or more anti-cancer agents. Thus, the embodiments provided herein are particularly useful for preventing and/or treating neoplasm that are resistant to or are likely to become resistant to one or more anti-cancer agents. In some embodiments, the neoplasm is not resistant and/or is not likely to become resistant to one or more anti-cancer agents. Thus, the embodiments provided herein are useful for preventing and/or treating neoplasm that is not resistant and/or is not likely to become resistant to one or more anti-cancer agents by administering a minimum dose of one or more anti-cancer agents sufficient to prevent and/or treat the neoplasm.

In some embodiments, the neoplasm is a glioblastoma, or any neoplasm associated with brain. In some embodiments, the neoplasm is related to one or more types of neoplasm provided herein.

Non-limiting examples of neoplasms include breast adenocarcinoma, pancreatic adenocarcinoma, lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, bladder cancer, hematological malignancies, squamous cell carcinomas, breast cancer, glioblastoma, or any neoplasm associated with brain including, but not limited to, astrocytomas (e.g., pilocytic astrocytoma, diffuse astrocytoma, anaplastic astrocytoma, and brain stem gliomas), glioblastomas (e.g., glioblastomas multiforme), meningioma, other gliomas (e.g., ependymomas, oligodendrogliomas, and mixed gliomas), and other brain tumors (e.g., pituitary tumors, craniopharyngiomas, germ cell tumors, pineal region tumors, medulloblastomas, and primary CNS lymphomas) (See, cancercenter.com/brain-cancer/types/tab/overview/, which is hereby incorporated by reference in its entirety). In some embodiments, the neoplasm is related to one or more types of neoplasm provided herein.

Anti-Cancer Agents

As used herein an "anti-cancer agent" can be an anti-cancer agent, anti-tumor agent, anti-cancer drug and/or anti-tumor drug that slows the growth, stops the growth, causes a reduction in size, eliminates and/or prevents relapse of a neoplasm. In some embodiments, the anti-cancer agent is a pro-drug.

In some embodiments, the anti-cancer agents are well-known in the art and in some embodiments are approved for therapeutic use and/or use in clinical trials by government agencies (e.g., FDA, EMEA, etc.). The dosing, route of administration, efficacy against known neoplasm types, side/adverse effects, mechanism of action, etc. of the anti-cancer agents may also be well-known in the art. In other embodiments, the anti-cancer agent is a compound that is believed to have anti-cancer effects (e.g., without being limiting, in vitro, in vivo and/or ex vivo in a laboratory and/or in a human clinical trial), but is not yet approved by a government agency for the treatment of cancer. Non-limiting example of anti-cancer agent includes Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) and Trametinib (Mekinist). Non-limiting example of anti-cancer agent includes Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), and Trametinib (Mekinist)-Temodar combination.

Anti-Cancer Response Modulators

As used herein an "anti-cancer response modulator" (also referred to herein as "modulator") improves the anti-cancer effect of a known or a novel anti-cancer agent against a neoplasm when used in combination with one or more of the modulators disclosed herein. In some embodiments, the anti-cancer agent may not have any effect in the absence of the modulator. In some embodiments the anti-cancer agent improves the anti-cancer activity of the modulator. In some embodiments, the modulator improves the anti-cancer activity of the anti-cancer agent. In some cases, the two work in concert to improve the anti-cancer activity of each other. In some embodiments, the neoplasm is likely to develop resistance, develops resistance, and/or is already resistant to the known or a novel anti-cancer agent. In some embodiments, the neoplasm is likely to develop resistance, develops resistance, and/or is already resistant to one or more modulators.

Several embodiments of modulators are contemplated. Non-limiting examples of modulators include those that improve the effect of anti-cancer agents including, but not limited to, anti-cancer agents that are effective against one or more types of neoplasm but ineffective against one or more other types of neoplasm.

Thus, modulators are contemplated that improve the effect of anti-cancer agents in a patient who may be non-responsive to a particular anti-cancer agent or the anti-cancer agent may be ineffective in a patient with a particular type of neoplasm even before initiation of treatment with the anti-cancer agent. The modulator can improve the effect of anti-cancer agents in a patient who may initially be responsive to a particular anti-cancer agent or the anti-cancer agent may initially be effective in a patient with a particular type of neoplasm but may eventually become ineffective. In some embodiments, the modulator can improve the effect of anti-cancer agents in a patient with a relapse of the neoplasm.

Non-limiting examples of modulators include quercetin, sodium phenyl butyrate (SPB) and epigallocatechin-3-gallate (EGCG). Other modulators are also contemplated. Quercetin is a flavonol found in many fruits, vegetables, leaves, and grains. It can be used as an ingredient in supplements, beverages, or foods. Quercetin is one of the most abundant dietary flavonoids with an average daily consumption of 25-50 mg. Sodium phenyl butyrate is a salt of an aromatic fatty acid, 4-phenylbutyrate (4-PBA) or 4-phenylbutyric acid and is classified by the FDA as an orphan drug for the treatment of urea cycle disorders. Epigallocatechin-3-gallate is a polyphenol and the most abundant catechin in tea. The modulators provided herein are non-toxic and/or minimally toxic with no and/or minimal side effects.

Dose of Modulator

The dose of modulators provided herein are exemplary and not intended to be limiting.

In some embodiments, quercetin is administered intravenously. The concentration of quercetin in a solution for intravenous administration is about 5 mg/ml to about 500 mg/ml. In some embodiments, the concentration of quercetin in a solution for intravenous administration is about 50 mg/ml. In some embodiments, quercetin is administered intravenously at a dose of about 0.05 g to about 10 g. In some embodiments, quercetin is administered intravenously at a dose of about 0.5 g to about 1 g. In some embodiments, quercetin is administered intravenously at a dose of about 0.05, 0.1, 0.2, 0.3, 0.4, 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5 or 10 g, or within a range defined by any two of the aforementioned values.

In some embodiments, quercetin is administered orally. The amount of quercetin in a composition for oral administration is about 100 mg to about 10 g. In some embodiments, quercetin is administered orally at a dose of about 0.5 g to about 4 g. In some embodiments, quercetin is administered orally at a dose of about 1 g. In some embodiments, quercetin is administered orally at a dose of about 0.05, 0.1, 0.2, 0.3, 0.4, 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5, 10, 15, 20, 25, 30, 35, 40, 45 or 50 g, or within a range defined by any two of the aforementioned values. In some embodiments, the composition for oral administration can be prepared into a solution for intravenous administration, wherein the concentration of quercetin is about 10 mg/ml to about 100 mg/ml. In some embodiments, quercetin is administered in a liposomal formulation. In some embodiments, quercetin is administered in a liposomal formulation at 50 mg a day. In some embodiments, quercetin is administered in a liposomal formulation at about 25 mg a day to about 75 mg a day. In some embodiments, quercetin is administered in a liposomal formulation at about 10, 15, 20, 25, 30, 35, 40, 45, 50, 55, 60, 65, 70, 75, 80, 85, 90, 95 or 100 mg a day, or within a range defined by any two of the aforementioned values.

In some embodiments, Quercetin by itself is not water soluble and therefore is administered in the oral dosage form. In some embodiments, Quercetin in the form of PG/PEG Propylene Glycol Quercetin (Quercetin PG) is water soluble and is used in the clinic as the IV dosage form.

In some embodiments, SPB is administered intravenously. The concentration of SPB in a solution for intravenous administration is about 20 mg/ml to about 2000 mg/ml. In some embodiments, the concentration of SPB in a solution for intravenous administration is about 200 mg/ml. In some embodiments, SPB is administered intravenously at a dose of about 0.5 g to about 100 g. In some embodiments, SPB is administered intravenously at a dose of about 1 g to about 10 g. In some embodiments, quercetin is administered intravenously at a dose of about 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95 or 100 g, or within a range defined by any two of the aforementioned values.

In some embodiments, SPB is administered orally. The amount of SPB in a composition for oral administration is about 0.1 g to about 50 g. In some embodiments, SPB is administered orally at a dose of about 0.5 g to about 1 g. In some embodiments, SPB is administered orally at a dose of 5 g to about 35 g. In some embodiments, SPB is administered orally at a dose of about 0.1, 0.2, 0.3, 0.4, 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5, 10, 15, 20, 25, 30, 35, 40, 45 or 50 g, or within a range defined by any two of the aforementioned values. In some embodiments, the composition for oral administration can be prepared into a solution for intravenous administration, wherein the concentration of SPB is about 20 mg/ml to about 2000 mg/ml.

In some embodiments, EGCG is administered intravenously. The concentration of EGCG in a solution for intravenous administration is about 5 mg/ml to about 100 mg/ml. In some embodiments, the concentration of EGCG in a solution for intravenous administration is about 20 mg/ml. In some embodiments, EGCG is administered intravenously at a dose of about 0.01 g to about 15 g. In some embodiments, EGCG is administered intravenously at a dose of about 0.1 g to about 1.5 g. In some embodiments, EGCG is administered intravenously at a dose of about 0.01, 0.05, 0.1 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 g, or within a range defined by any two of the aforementioned values.

In some embodiments, EGCG is administered orally. The amount of EGCG in a composition for oral administration is about 0.1 g to about 3 g. In some embodiments, EGCG is administered orally at a dose of about 0.2 g to about 1 g. In some embodiments, EGCG is administered orally at a dose of 0.5 g to about 2.5 g. In some embodiments, EGCG is administered orally at a dose of about 0.1 0.2, 0.3, 0.4, 0.5, 0.6, 0.7, 0.8, 0.9, 1, 1.5, 2, 2.5 or 3 g, or within a range defined by any two of the aforementioned values. In some embodiments, the composition for oral administration can be prepared into a solution for intravenous administration, wherein the concentration of EGCG is about 5 mg/ml to about 100 mg/ml. In some embodiments, a preventive dose of EGCG is about 0.27 g administered 2 times a day. In some embodiments, a preventive dose of EGCG is about 0.27 g administered 3 times a day.

Combinations

A surprising and unexpected anti-cancer effect was observed when one or more anti-cancer agents were used in combination with one or more modulators provided herein. The surprising and unexpected result was a better than expected result wherein the effectiveness of the one or more anti-cancer agents was improved when used in combination with one or more modulators as compared to the anti-cancer agent in the absence of the modulator(s). The potentiation was achieved by co-administering the one or more anti-cancer agents and one or more modulators.

Therefore, provided herein are combinations of one or more anti-cancer agents and one or more modulators. The one or more modulators can improve the effect of one or more anti-cancer agent against one or more neoplasm types provided herein. The potentiation can occur in several ways. Non-limiting examples include enhancing the effectiveness of an already effective anti-cancer agent, making an ineffective anticancer agent effective (the anticancer agent could also have been previously effective but become ineffective following long term and/or short term use in a patient), increasing the length of time for which an anti-cancer agent is effective, decreasing the effective dose of administration of the anti-cancer agent, decreasing the duration of time for which anti-cancer agent is administered, decreasing the frequency of administration of an anti-cancer agent, and/or enabling the administration of anti-cancer agent via a more amenable route.

The one or more anti-cancer agents can be provided at any dose, via any of the routes of administration, in any order of administration, at any frequency of administration, and/or any dosage form provided herein. Similarly, the one or more modulators can be provided at any dose, via any of the routes of administration, in any order of administration, at any frequency of administration, and/or any dosage form provided herein. Also, the combination of one or more anti-cancer agent and one or more modulators can be provided at any dose, via any of the routes of administration, in any order of administration, at any frequency of administration, and/or any dosage form provided herein.

Combinations can comprise, consist of, or consist essentially of, one or more anti-cancer agents and one or more modulators. In some embodiments, the combination comprises, consists of, or consists essentially of, one or more anti-cancer agents and one modulator selected from the group consisting of quercetin, SPB and EGCG. In some embodiments, the modulator is quercetin. In some embodiments, the modulator is SPB. In some embodiments, the modulator is EGCG. In some embodiments, the combination comprises, consists of, or consists essentially of, one or more anti-cancer agents and at least one modulator. In some embodiments, the at least one modulator is selected from the group consisting of quercetin, SPB and EGCG. For example, in some embodiments, the combination can comprise, consist of, or consist essentially of, the anticancer agent and quercetin, or the anti-cancer agent and SPB, or the anti-cancer agent and EGCG. In some embodiments, the combination comprises, consists of, or consists essentially of, one or more anti-cancer agents and at least two modulators. In some embodiments, the at least two modulators are selected from the group consisting of quercetin, SPB and EGCG. For example, in some embodiments, the combination can comprise, consist of, or consist essentially of, the anticancer agent and quercetin and SPB as the modulators, or the anticancer agent and quercetin and EGCG as the modulators, or the anticancer agent and SPB and EGCG as the modulators. In some embodiments, the anti-cancer agent is Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist). In some embodiments, the anti-cancer agents is Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination.

In some embodiments, the combination may comprise, consist of, or consist essentially of, one or more additional modulators, for example, a third modulator selected from the group consisting of quercetin, SPB and EGCG. In some embodiments, if the first two modulators are quercetin and SPB, the third modulator is EGCG, if the first two modulators are quercetin and EGCG, the third modulator is SPB, and if the first two modulators are SPB and EGCG, the third modulator is quercetin. Therefore, for example, the combination can comprise, consist of, or consist essentially of, the anticancer agent and quercetin, SPB and EGCG as the three modulators. In some embodiments, the anti-cancer agent is Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist). In some embodiments, anti-cancer agents is Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination.

In some embodiments, the combinations in the compositions, kits, uses and/or methods described herein comprise, consist of, or consist essentially of, Quercetin+Rituximab (Rituxan). In some embodiments, the combinations in the compositions, kits, uses and/or methods described herein comprise, consist of, or consist essentially of, SPB+Rituximab (Rituxan). In some embodiments, the combinations in the compositions, kits, uses and/or methods described herein comprise, consist of, or consist essentially of, EGCG+Rituximab (Rituxan). In some embodiments, the combinations in the compositions, kits, uses and/or methods described herein comprise, consist of, or consist essentially of, Quercetin+SPB+Rituximab (Rituxan). In some embodiments, the combinations in the compositions, kits, uses and/or methods described herein comprise, consist of, or consist essentially of, Quercetin+EGCG+Rituximab (Rituxan). In some embodiments, the combinations in the compositions, kits, uses and/or methods described herein comprise, consist of, or consist essentially of, SPB+EGCG+Rituximab (Rituxan). In some embodiments, the combinations in the compositions, kits, uses and/or methods described herein comprise, consist of, or consist essentially of, Quercetin+SPB+EGCG+Rituximab (Rituxan).

In some embodiments, the combinations in the compositions, kits, uses and/or methods described herein comprise, consist of, or consist essentially of, Quercetin+Ibrutinib (Imbruvica). In some embodiments, the combinations in the compositions, kits, uses and/or methods described herein comprise, consist of, or consist essentially of, SPB+Ibrutinib (Imbruvica). In some embodiments, the combinations in the compositions, kits, uses and/or methods described herein comprise, consist of, or consist essentially of, EGCG+Ibrutinib (Imbruvica). In some embodiments, the combinations in the compositions, kits, uses and/or methods described herein comprise, consist of, or consist essentially of, Quercetin+SPB+Ibrutinib (Imbruvica). In some embodiments, the combinations in the compositions, kits, uses and/or methods described herein comprise, consist of, or consist essentially of, Quercetin+EGCG+Ibrutinib (Imbruvica). In some embodiments, the combinations in the compositions, kits, uses and/or methods described herein comprise, consist of, or consist essentially of, SPB+EGCG+Ibrutinib (Imbruvica). In some embodiments, the combinations in the compositions, kits, uses and/or methods described herein comprise, consist of, or consist essentially of, Quercetin+SPB+EGCG+Ibrutinib (Imbruvica).

In some embodiments, the combinations in the compositions, kits, uses and/or methods described herein comprise, consist of, or consist essentially of, Quercetin+Cetuximab (Erbitux). In some embodiments, the combinations in the compositions, kits, uses and/or methods described herein comprise, consist of, or consist essentially of, SPB+Cetuximab (Erbitux). In some embodiments, the combinations in the compositions, kits, uses and/or methods described herein comprise, consist of, or consist essentially of, EGCG+Cetuximab (Erbitux). In some embodiments, the combinations in the compositions, kits, uses and/or methods described herein comprise, consist of, or consist essentially of, Quercetin+SPB+Cetuximab (Erbitux). In some embodiments, the combinations in the compositions, kits, uses and/or methods described herein comprise, consist of, or consist essentially of, Quercetin+EGCG+Cetuximab (Erbitux). In some embodiments, the combinations in the compositions, kits, uses and/or methods described herein comprise, consist of, or consist essentially of, SPB+EGCG+Cetuximab (Erbitux). In some embodiments, the combinations in the compositions, kits, uses and/or methods described herein comprise, consist of, or consist essentially of, Quercetin+SPB+EGCG+Cetuximab (Erbitux).

In some embodiments, the combinations in the compositions, kits, uses and/or methods described herein comprise, consist of, or consist essentially of, Quercetin+Crizotinib (Xalkori). In some embodiments, the combinations in the compositions, kits, uses and/or methods described herein comprise, consist of, or consist essentially of, SPB+Crizotinib (Xalkori). In some embodiments, the combinations in the compositions, kits, uses and/or methods described herein comprise, consist of, or consist essentially of, EGCG+Crizotinib (Xalkori). In some embodiments, the combinations in the compositions, kits, uses and/or methods described herein comprise, consist of, or consist essentially of, Quercetin+SPB+Crizotinib (Xalkori). In some embodiments, the combinations in the compositions, kits, uses and/or methods described herein comprise, consist of, or consist essentially of, Quercetin+EGCG+Crizotinib (Xalkori). In some embodiments, the combinations in the compositions, kits, uses and/or methods described herein comprise, consist of, or consist essentially of, SPB+EGCG+Crizotinib (Xalkori). In some embodiments, the combinations in the compositions, kits, uses and/or methods described herein comprise, consist of, or consist essentially of, Quercetin+SPB+EGCG+Crizotinib (Xalkori).

In some embodiments, the combinations in the compositions, kits, uses and/or methods described herein comprise, consist of, or consist essentially of, Quercetin+Ceritinib (Zykadia). In some embodiments, the combinations in the compositions, kits, uses and/or methods described herein comprise, consist of, or consist essentially of, SPB+Ceritinib (Zykadia). In some embodiments, the combinations in the compositions, kits, uses and/or methods described herein comprise, consist of, or consist essentially of, EGCG+Ceritinib (Zykadia). In some embodiments, the combinations in the compositions, kits, uses and/or methods described herein comprise, consist of, or consist essentially of, Quercetin+SPB+Ceritinib (Zykadia). In some embodiments, the combinations in the compositions, kits, uses and/or methods described herein comprise, consist of, or consist essentially of, Quercetin+EGCG+Ceritinib (Zykadia). In some embodiments, the combinations in the compositions, kits, uses and/or methods described herein comprise, consist of, or consist essentially of, SPB+EGCG+Ceritinib (Zykadia). In some embodiments, the combinations in the compositions, kits, uses and/or methods described herein comprise, consist of, or consist essentially of, Quercetin+SPB+EGCG+Ceritinib (Zykadia).

In some embodiments, the combinations in the compositions, kits, uses and/or methods described herein comprise, consist of, or consist essentially of, Quercetin+Trastuzumab (Herceptin). In some embodiments, the combinations in the compositions, kits, uses and/or methods described herein comprise, consist of, or consist essentially of, SPB+Trastuzumab (Herceptin). In some embodiments, the combinations in the compositions, kits, uses and/or methods described herein comprise, consist of, or consist essentially of, EGCG+Trastuzumab (Herceptin). In some embodiments, the combinations in the compositions, kits, uses and/or methods described herein comprise, consist of, or consist essentially of, Quercetin+SPB+Trastuzumab (Herceptin). In some embodiments, the combinations in the compositions, kits, uses and/or methods described herein comprise, consist of, or consist essentially of, Quercetin+EGCG+Trastuzumab (Herceptin). In some embodiments, the combinations in the compositions, kits, uses and/or methods described herein comprise, consist of, or consist essentially of, SPB+EGCG+Trastuzumab (Herceptin). In some embodiments, the combinations in the compositions, kits, uses and/or methods described herein comprise, consist of, or consist essentially of, Quercetin+SPB+EGCG+Trastuzumab (Herceptin).

In some embodiments, the combinations in the compositions, kits, uses and/or methods described herein comprise, consist of, or consist essentially of, Quercetin+Everolimus (Afinitor). In some embodiments, the combinations in the compositions, kits, uses and/or methods described herein comprise, consist of, or consist essentially of, SPB+Everolimus (Afinitor). In some embodiments, the combinations in the compositions, kits, uses and/or methods described herein comprise, consist of, or consist essentially of, EGCG+Everolimus (Afinitor). In some embodiments, the combinations in the compositions, kits, uses and/or methods described herein comprise, consist of, or consist essentially of, Quercetin+SPB+Everolimus (Afinitor). In some embodiments, the combinations in the compositions, kits, uses and/or methods described herein comprise, consist of, or consist essentially of, Quercetin+EGCG+Everolimus (Afinitor). In some embodiments, the combinations in the compositions, kits, uses and/or methods described herein comprise, consist of, or consist essentially of, SPB+EGCG+Everolimus (Afinitor). In some embodiments, the combinations in the compositions, kits, uses and/or methods described herein comprise, consist of, or consist essentially of, Quercetin+SPB+EGCG+Everolimus (Afinitor).

In some embodiments, the combinations in the compositions, kits, uses and/or methods described herein comprise, consist of, or consist essentially of, Quercetin+Afatinib (Gilotrif). In some embodiments, the combinations in the compositions, kits, uses and/or methods described herein comprise, consist of, or consist essentially of, SPB+Afatinib (Gilotrif). In some embodiments, the combinations in the compositions, kits, uses and/or methods described herein comprise, consist of, or consist essentially of, EGCG+Afatinib (Gilotrif). In some embodiments, the combinations in the compositions, kits, uses and/or methods described herein comprise, consist of, or consist essentially of, Quercetin+SPB+Afatinib (Gilotrif). In some embodiments, the combinations in the compositions, kits, uses and/or methods described herein comprise, consist of, or consist essentially of, Quercetin+EGCG+Afatinib (Gilotrif). In some embodiments, the combinations in the compositions, kits, uses and/or methods described herein comprise, consist of, or consist essentially of, SPB+EGCG+Afatinib (Gilotrif). In some embodiments, the combinations in the compositions, kits, uses and/or methods described herein comprise, consist of, or consist essentially of, Quercetin+SPB+EGCG+Afatinib (Gilotrif).

In some embodiments, the combinations in the compositions, kits, uses and/or methods described herein comprise, consist of, or consist essentially of, Quercetin+Bevacizumab (Avastin). In some embodiments, the combinations in the compositions, kits, uses and/or methods described herein comprise, consist of, or consist essentially of, SPB+Bevacizumab (Avastin). In some embodiments, the combinations in the compositions, kits, uses and/or methods described herein comprise, consist of, or consist essentially of, EGCG+Bevacizumab (Avastin). In some embodiments, the combinations in the compositions, kits, uses and/or methods described herein comprise, consist of, or consist essentially of, Quercetin+SPB+Bevacizumab (Avastin). In some embodiments, the combinations in the compositions, kits, uses and/or methods described herein comprise, consist of, or consist essentially of, Quercetin+EGCG+Bevacizumab (Avastin). In some embodiments, the combinations in the compositions, kits, uses and/or methods described herein comprise, consist of, or consist essentially of, SPB+EGCG+Bevacizumab (Avastin). In some embodiments, the combinations in the compositions, kits, uses and/or methods described herein comprise, consist of, or consist essentially of, Quercetin+SPB+EGCG+Bevacizumab (Avastin).

In some embodiments, the combinations in the compositions, kits, uses and/or methods described herein comprise, consist of, or consist essentially of, Quercetin+Trametinib (Mekinist). In some embodiments, the combinations in the compositions, kits, uses and/or methods described herein comprise, consist of, or consist essentially of, SPB+Trametinib (Mekinist). In some embodiments, the combinations in the compositions, kits, uses and/or methods described herein comprise, consist of, or consist essentially of, EGCG+Trametinib (Mekinist). In some embodiments, the combinations in the compositions, kits, uses and/or methods described herein comprise, consist of, or consist essentially of, Quercetin+SPB+Trametinib (Mekinist). In some embodiments, the combinations in the compositions, kits, uses and/or methods described herein comprise, consist of, or consist essentially of, Quercetin+EGCG+Trametinib (Mekinist). In some embodiments, the combinations in the compositions, kits, uses and/or methods described herein comprise, consist of, or consist essentially of, SPB+EGCG+Trametinib (Mekinist). In some embodiments, the combinations in the compositions, kits, uses and/or methods described herein comprise, consist of, or consist essentially of, Quercetin+SPB+EGCG+Trametinib (Mekinist).

In some embodiments, the combinations in the compositions, kits, uses and/or methods described herein comprise, consist of, or consist essentially of, Quercetin+Trametinib (Mekinist)+Temodar. In some embodiments, the combinations in the compositions, kits, uses and/or methods described herein comprise, consist of, or consist essentially of, SPB+Trametinib (Mekinist)+Temodar. In some embodiments, the combinations in the compositions, kits, uses and/or methods described herein comprise, consist of, or consist essentially of, EGCG+Trametinib (Mekinist)+Temodar. In some embodiments, the combinations in the compositions, kits, uses and/or methods described herein comprise, consist of, or consist essentially of, Quercetin+SPB+Trametinib (Mekinist)+Temodar. In some embodiments, the combinations in the compositions, kits, uses and/or methods described herein comprise, consist of, or consist essentially of, Quercetin+EGCG+Trametinib (Mekinist)+Temodar. In some embodiments, the combinations in the compositions, kits, uses and/or methods described herein comprise, consist of, or consist essentially of, SPB+EGCG+Trametinib (Mekinist)+Temodar. In some embodiments, the combinations in the compositions, kits, uses and/or methods described herein comprise, consist of, or consist essentially of, Quercetin+SPB+EGCG+Trametinib (Mekinist)+Temodar.

The potentiation can be additive or synergistic. A synergistic effect is greater than an additive effect. An additive effect is observed when the potentiation is equal to the sum of the individual effects of the anti-cancer agent(s) and modulator(s). A synergistic effect is observed when the potentiation is greater than the sum of the individual effects of the anti-cancer agent and modulator(s). Synergistic effect, additive effect or both can occur human patients, non-human patients, non-patient human volunteers, in vivo models, ex vivo models, in vitro models, etc.

Potentiation can range from about <1 to about 100 fold. In some embodiments, the synergistic effect is about 3 to about 30 fold. In some embodiments, the potentiation ranges from <1, 1, >1, 2, 3, 4, 5, 6, 7, 8, 9, 10, 20, 30, 40, 50, 60, 70, 80, 90, or 100 fold, or within a range defined by any two of the aforementioned values. In some embodiments, a synergistic effect allows for a reduction in the requirement of an anti-cancer agent to about 25% to about 75% of the recommended dose. In some embodiments, a synergistic effect allows for a reduction in the requirement of an anti-cancer agent to about 5, 10, 20, 30, 40, 50, 60, 70, 80, 90, or 95% of the recommended dose, or a value within a range defined by any two of the aforementioned values.

For example, the combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) with quercetin can produce a synergistic effect on a neoplasm as compared to Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) alone. In some embodiments, the combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) with quercetin and SPB can produce a synergistic effect on a neoplasm as compared to Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) alone. In some embodiments, the combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) or a derivative thereof with SPB can produce a synergistic effect on a neoplasm as compared to Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) alone. In some embodiments, the combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar with quercetin can produce a synergistic effect on a neoplasm as compared to Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar alone. In some embodiments, the combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar with quercetin and SPB can produce a synergistic effect on a neoplasm as compared to Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar alone. In some embodiments, the combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar or a derivative thereof with SPB can produce a synergistic effect on a neoplasm as compared to Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar alone.

In some embodiments, additive and/or synergistic or sustained response to combinational therapy is seen with tyrosine kinase inhibitors and monoclonal antibodies targets for which include Pi3k, M-TOR, EGFR (including Her2), Mek, VEGF, RANK, CD20, ALK, and c-Met.

In some embodiments, "combination therapy" is intended to encompass administration of these therapeutic agents in a sequential manner, wherein each therapeutic agent is administered at a different time, as well as administration of these therapeutic agents, or at least two of therapeutic agents concurrently, or in a substantially simultaneous manner. Simultaneous administration can be accomplished, for example, by administering to the subject a single dosage form, for example a solution, pill or capsule, having a fixed ratio of each therapeutic agent or in multiple, single dosage forms for each of therapeutic agents. Sequential or substantially simultaneous administration of each therapeutic agent can be effected by any appropriate route including, but not limited to, oral routes, intravenous routes, intramuscular routes, and direct absorption through mucous membrane tissues.

In some embodiments, mixtures of compositions of the present invention can also be administered to the patient as a simple mixture or in suitable formulated pharmaceutical compositions. In some embodiments, combination therapy can be achieved by administering two or more agents, e.g., two or more other therapeutic agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

The potentiation can be measured in one or more assays that measure effects such as apoptosis, cellular metabolic changes, cellular morphological changes, etc., or other effects that would be well-known to one of ordinary skill in the art. In some embodiments, the combination of anti-cancer agent(s) and one or more modulators causes an induction of apoptosis, which can be measured using the MiCK® assay (Example 42). In some embodiments, the modulator can suppress angiogenesis within/around the neoplasm. For example, Quercetin causes suppression of angiogenesis in glioma cells.

In some embodiments, the one or more modulators provided herein are effective as anticancer agents without the presence of an anti-cancer agent. Thus, in some embodiments, the one or more modulators provided herein are independently effective as anti-cancer agents, i.e., without co-administration of one or more anti-cancer agents. For example, an anti-cancer effect is observed when quercetin and SPB are co-administered without co-administration of one or more anti-cancer agents (See, Example 15-Example 20). (See, Example 15, and Example 17-Example 20).

However, when the one or more modulators provided herein are administered in combination with one or more anti-cancer agents, a synergistic anti-cancer effect is observed. Thus, in some embodiments, a synergistic anti-cancer effect is observed when the one or more modulators provided herein are co-administered with the one or more anti-cancer agents provided herein. For example, a synergistic anti-cancer effect is observed when Quercetin PG is co-administered with Afatinib (See, Example 16). In some embodiments, a synergistic anti-cancer effect is achieved when Quercetin PG is co-administered with Temodar and Trametinib (Mekinist) (See, Example 18). In some embodiments, a synergistic anti-cancer effect is achieved when Quercetin-PG and SPB are co-administered with Afatinib (See, Example 14, Example 15, and Example 17). In some embodiments, a synergistic anti-cancer effect is observed when Quercetin PG is co-administered with Trametinib (See, Example 18). Additional data related to synergistic anti-cancer effects are provided in Example 19-Example 45.

Route of Administration

The route of administration of the modulator(s) and anti-cancer agent(s) can be determined by one of ordinary skill in the art based on the circumstances. Several non-limiting routes of administrations are possible including parenteral, subcutaneous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal.

Any route of administration provided herein can be used for the combination of anti-cancer agent(s) and modulator(s) or for the individual components of the combination. For example, the combination of anti-cancer agent and modulator can be administered intravenously, orally or both. In some embodiments, one or more components in the combination can be administered via one route (e.g., intravenously) and the other components can be administered via a different route (e.g., orally). In some embodiments, all components in the combination are administered via the same route (e.g., either intravenously or orally). The anti-cancer agent and modulators can be administered via any combination of intravenous and oral routes as shown in the non-limiting examples of Table 1 and Table 2.

TABLE 1

Combinations comprising, consisting of, or consisting essentially of, one anti-cancer agent and two modulators (S1, S2)

| Combination | Route of administration | | |
|---|---|---|---|
| | Anti-cancer agent | S1 | S2 |
| 1 | IV | IV | IV |
| 2 | Oral | IV | IV |
| 3 | IV | Oral | IV |
| 4 | IV | IV | Oral |
| 5 | Oral | Oral | IV |
| 6 | Oral | IV | Oral |
| 7 | IV | Oral | Oral |
| 8 | Oral | Oral | Oral |

TABLE 2

Combinations comprising, consisting of, or consisting essentially of, one anti-cancer agent and three modulators (S1, S2, S3)

| | Route of administration | | | |
|---|---|---|---|---|
| Combination | Anti-cancer agent | S1 | S2 | S3 |
| 1 | IV | IV | IV | IV |
| 2 | Oral | IV | IV | IV |
| 3 | IV | Oral | IV | IV |
| 4 | IV | IV | Oral | IV |
| 5 | IV | IV | IV | Oral |
| 6 | Oral | Oral | IV | IV |
| 7 | Oral | IV | Oral | IV |
| 8 | Oral | IV | IV | Oral |
| 9 | IV | Oral | Oral | IV |
| 10 | IV | Oral | IV | Oral |
| 11 | IV | IV | Oral | Oral |
| 12 | Oral | Oral | Oral | IV |
| 13 | IV | Oral | Oral | Oral |
| 14 | Oral | IV | Oral | Oral |
| 15 | Oral | Oral | IV | Oral |
| 16 | Oral | Oral | Oral | Oral |

In some embodiments of Table 1 and Table 2, the anti-cancer agent is Rituximab, Ibrutinib (Imbruvica), Crizotonib (Xalkori), Ceritinib, Herceptin (Everolimus), Afatinib, or Trametinib (Mekinist), S1 is quercetin, S2 is SPB, and S3 is EGCG. In some embodiments of Table 1 and Table 2, the anti-cancer agent is Rituximab, Ibrutinib (Imbruvica), Crizotonib (Xalkori), Ceritinib, Herceptin (Everolimus), Afatinib, Trametinib (Mekinist), or Trametinib (Mekinist)-Temodar combination, S1 is quercetin, S2 is SPB, and S3 is EGCG.

Order of Administration

Any order of administration can be used for the one or more anti-cancer agents and one or more modulators in a combination. For example, the one or more anti-cancer agents and the one or more modulators in the combination can be administered simultaneously or sequentially. For example, all components of the combination are administered simultaneously, or only some of the components of the combination are administered simultaneously and the rest are administered sequentially. In some embodiments, none of the components are administered simultaneously, i.e., all the components are administered sequentially. When administering sequentially, any order of administration can be used. For example, when administering a combination of one anti-cancer agent and two modulators, the anti-cancer agent can be administered first followed by the two modulators either simultaneously or sequentially in any order, or the two modulators can be administered first either simultaneously or sequentially in any order followed by the anti-cancer agent, or one of the modulator each can be administered before and after the administration of the anti-cancer agent. Additional orders of administration are possible and contemplated when the combination comprises, consists of, or consists essentially of, additional components, for example, a third modulator.

Frequency of Administration

Frequency of administration of the anti-cancer agent is as known in the art. Frequency of administration of the anti-cancer agent can be varied depending various parameters such as level of potentiation, prognosis following administration of a combination provided herein, patient compliance, side effects, etc., for example, daily, weekly, biweekly, monthly, bimonthly, or as is known in the art. Modulators can be administered along with the anti-cancer agent daily, weekly, biweekly, monthly, bimonthly, less frequently compared to the anti-cancer agent, or more frequently compared to the anti-cancer agent.

Administration can be daily, or 1, 2, 3, 4, 5, 6 or more times weekly, or more or less frequently as required. Administration can be provided as a single dose or as divided doses, such that a daily dose may be given in 2, 3, 4, or more portions in a single day.

Co-administration of the components of a combination may comprise, consist of, or consist essentially of, administering the components simultaneously, or within about 1, 5, 15, 30, 45 or 60 minute of one another, or within any range defined by the aforementioned values. Co-administration of the components of a combination may comprise, consist of, or consist essentially of, administering the components within about 1 hour to within about 6 hours of one another, or within any range defined by the aforementioned values.

Pharmaceutical Formulations

In some embodiments, pharmaceutical formulations for prophylaxis, treatment or both of a neoplasm are provided. The formulation can be a single composition for co-administration comprising, consisting of, or consisting essentially of, at least one anti-cancer agent and one, two, three or more modulators. In some embodiments, the formulation comprises, consists of, or consists essentially of, more than one composition, e.g. the anti-cancer agent in one dosage form, and the one or more modulators in a second, third or fourth dosage form. Several compositions are contemplated. The type of composition to be administered can be determined by one of ordinary skill in the art based on the circumstances under which administration is desired.

The compositions provided herein comprise, consist of, or consist essentially of, active ingredients, inactive ingredients, excipients, additives, and/or pharmaceutically acceptable carriers. Examples of additives include natural polymer compounds, inorganic salts, binders, lubricants, disintegrants, surfactants, thickeners, coating agents, pH adjusters, antioxidants, flavoring agents, preservatives, and colorants among others. Examples of other pharmaceutically acceptable carriers include liquid carriers such as water, alcohol, emulsion, and solid carriers such as gel, powder, etc. Standard pharmaceutical formulation techniques and ingredients can be used, such as those disclosed in *Remington's The Science and Practice of Pharmacy*, 21st Ed., Lippincott Williams & Wilkins (2005), which is hereby incorporated by reference in its entirety.

Compositions for intravenous administration comprise, consist of, or consist essentially of, excipient and pharmaceutically acceptable carries including one or more of sodium chloride, dextrose, and sterile water. Compositions can comprise, consist of, or consist essentially of, aqueous isotonic sterile injection solutions, which can comprise, consist of, or consist essentially of, one or more of antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Compositions for oral administration can be any dosage form that is suitable for oral ingestion, for example, liquid compositions such as elixir, suspension, syrup, emulsion, ampoule, etc., solid compositions such as gel, gum, drop, powder, granule, pill, sugar-coated tablet, film-coated tablet, capsule, package agent, etc. Also contemplated are sustained-release compositions such as gel-coated compositions, multi-coated compositions, localized release compositions.

In some embodiments, the compositions are administered by intravenous infusion. The compositions can be presented in unit-dose or multi-dose sealed containers, such as ampules and/or vials. Injection solutions and suspensions can be prepared from sterile powders, granules, and/or tablets. In some embodiments, the compositions to be administered can be formulated as pharmaceutical formulations for delivery via one or more of the routes provided herein.

A composition can comprise, consist of, or consist essentially of, a combination of one or more anti-cancer agents and one or more modulators, wherein the one or more anti-cancer agents and one or more modulators can be present in any dosage form. For example, in a composition comprising, consisting of, or consisting essentially of, a combination of one anti-cancer agent and two modulators, all three components can be in the same dosage form (e.g., for intravenous administration or for oral administration), or one of the components in the combination can be of one dosage form (e.g., for intravenous administration or for oral administration) and other two component in the combination can be of a different dosage form (e.g., for intravenous administration or for oral administration). In some embodiments, all three components in the combination may be of a different dosage form (e.g., for intravenous administration, for oral administration, and a third dosage form). In some embodiments, when the combination additionally comprises, consists of, or consists essentially of, a third modulator, the dosage form of the third modulator may be the same as one of the other components in the combination or the third modulator may be present in a different (e.g., fourth) dosage form. The various dosage forms can be administered in an order as disclosed herein.

For example, in a composition comprising, consisting of, or consisting essentially of, a combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) as the anti-cancer agent and quercetin and SPB as the two modulators, all three can be in an intravenous or oral dosage form, or Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) can be in an intravenous dosage form and quercetin and SPB can be in an oral dosage form, or Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) can be in oral dosage form and quercetin and SPB can be in an intravenous dosage form. In some embodiments, the combination may comprise, consist of, or consist essentially of, a third modulator (e.g., EGCG) that is in the same or a different dosage form than the anti-cancer agent and/or one or more of the modulators. In some embodiments, in a composition comprising, consisting of, or consisting essentially of, a combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar as the anti-cancer agent and quercetin and SPB as the two modulators, all three can be in an intravenous or oral dosage form, or Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar can be in an intravenous dosage form and quercetin and SBP can be in an oral dosage form, or Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar can be in oral dosage form and quercetin and SPB can be in an intravenous dosage form. In some embodiments, the combination may comprise, consist of, or consist essentially of, a third modulator (e.g., EGCG) that is in the same or a different dosage form than the anti-cancer agent and/or one or more of the modulators.

Kits

Inasmuch as it may desirable to administer one or more combinations provided herein, for example, for the purpose of preventing and/or treating a neoplasm, it is within the scope of the present disclosure to provide the components of a combination as a kit such that the components of the combination are suitable for co-administration.

A kit comprising, consisting of, or consisting essentially of, one or more anti-cancer agents to be used in combination with one or more modulators is provided.

In some embodiments, the kit comprises, consists of, or consists essentially of, one anti-cancer agent to be used in combination with two modulators. In some embodiments, the kit further comprises, consists of, or consists essentially of, a third modulator. Thus, the kit comprises, consists of, or consists essentially of, one anti-cancer agent to be used in combination with three modulators.

The components can be separately provided such as in separate containers, or in separate compartments of a divided bottle or divided foil packet (e.g., a blister pack used for the packaging of tablets, capsules, etc.).

The kit is particularly suitable for administering different dosage forms, for example, oral and intravenous, for administering the components at different dosage intervals, and/or for titration of components against one another. The kit typically comprises, consists of, or consists essentially of, directions for administration and may additionally be provided with a memory aid to ensure compliance.

The components in the kit may exist in dissolved form, undissolved form or a combination thereof. If present in undissolved form, the undissolved component may be combined with another component present in a dissolved form in a specific stoichiometric amount prior to use. If all the components are present in an undissolved form, the components can either be administered as such (e.g., orally) or dissolved into a solvent (e.g., water) prior to administration (e.g., intravenously).

In some embodiments, the kit comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) as the anti-cancer agent to be used in combination with quercetin and SPB as the two modulators. In some embodiments, the kit can comprise, consist of, or consist essentially of, EGCG as the third modulator. Thus, the kit comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) as the anti-cancer agent to be used in combination with quercetin, SPB and EGCG as the three modulators. In some embodiments, the kit comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combiantion as the anti-cancer agent to be used in combination with quercetin and SPB as the two modulators. In some embodiments, the kit can comprise, consist of, or consist essentially of, EGCG as the third modulator. Thus, the kit comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination as the anti-cancer agent to be used in combination with quercetin, SPB and EGCG as the three modulators.

Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) and Trametinib (Mekinist)

In any of the methods, uses, and kits disclosed herein, the compositions can be used for the treatment of disease, including but not limited to cancer, including but not limited to the following and any other disease or cancer known in the art to be treated by the disclosed compounds.

Rituximab is used to treat certain autoimmune diseases and types of cancer such as non-Hodgkin's lymphoma, chronic lymphocytic leukemia, rheumatoid arthritis, idiopathic thrombocytopenic purpura, pemphigus vulgaris and myasthenia gravis. Rituximab eliminates cells that have CD20 on their surfaces (e.g., normal and cancerous B cells) and is used to treat B cell-related diseases.

Ibrutinib (Imbruvica) is used to treat chronic lymphocytic leukemia, Waldenstrom's macroglobulinemia, and as a second-line treatment for mantle cell lymphoma, marginal zone lymphoma, and chronic graft versus host disease. Ibrutinib is a small molecule drug that binds to Bruton's tyrosine kinase (BTK) that is important in B cells.

Crizotinib (trade name Xalkori) is an anti-cancer ALK (anaplastic lymphoma kinase) and ROS1 (c-ros oncogene 1) inhibitor approved for treatment of some non-small cell lung carcinoma (NSCLC), and undergoing clinical trials testing its safety and efficacy in anaplastic large cell lymphoma, neuroblastoma, and other advanced solid tumors in both adults and children. Crizotinib has an aminopyridine structure and functions as a protein kinase inhibitor by competitive binding within the ATP-binding pocket of target kinases.

Ceritinib (trade name Zykadia) is an anaplastic lymphoma kinase (ALK) inhibitor drug for the treatment of a specific type of lung cancer.

Trastuzumab (Herceptin, Evrolimus) is a monoclonal antibody used to treat breast cancer, specifically, HER2 receptor positive breast cancer.

Afatinib (Trade name Gilotrif) is a drug approved for first-line treatment of patients with distinct types of metastatic (EGFR mutation positive) non-small cell lung carcinoma (NSCLC). It acts as an irreversible covalent inhibitor of the receptor tyrosine kinases epidermal growth factor receptor (EGFR) and erbB-2 (HER2).

Erlotinib (trade name Tarceva) is also another receptor tyrosine kinase inhibitor, which acts on the epidermal growth factor receptor (EGFR). IT is approved for the treatment of locally advanced or metastatic non-small cell lung cancer that has failed at least one prior chemotherapy regimen. It is also approved in combination with gemcitabine for treatment of locally advanced, unresectable, or metastatic pancreatic cancer. Cetuximab (Trade name ERBITUX) is a monoclonal antibody targeted therapy, in combination with radiation therapy, is approved for the initial treatment of locally or regionally advanced head and neck cancer, it also is approved for the treatment of certain patients who have colorectal cancer that has spread to other parts of the body.

Everolimus (Afinitor) is a derivative of sirolimus as an inhibitor of mammalian target of rapamycin (mTOR).approved for prevention of kidney cancer, Prevention of organ rejection after renal transplant, Progressive or metastatic pancreatic neuroendocrine tumors not surgically removable, Breast cancer in post-menopausal women with advanced hormone-receptor positive, HER2-negative type cancer, in conjunction with exemestane, Progressive, well-differentiated non-functional, neuroendocrine tumors (NET) of gastrointestinal (GI) or lung origin with unresectable, locally advanced or metastatic disease.

Bevacizumab (Avastin) is a monoclonal antibody treatment that is approved in 6 cancer types: metastatic colorectal cancer (MCRC), metastatic non-squamous non-small cell lung cancer (NSCLC), metastatic renal cell carcinoma (mRCC), recurrent glioblastoma (rGBM), persistent, recurrent, or metastatic cervical cancer (CC), and recurrent epithelial ovarian, fallopian tube or primary peritoneal cancer (rOC).

Trametinib (trade name Mekinist) is a MEK (mitogen-activated protein kinase enzymes) inhibitor with anti-cancer activity and inhibits MEK1 and MEK2. Trametinib is used for treating metastatic melanoma.

In some embodiments, the dose for the targeted therapies provided herein, is defined based on biological effective dose (BED). In some embodiments, the BED ranges from about 0.01 mg/day to about 1000 mg/day. In some embodiments, the BED ranges between about 0.1 mg/day and about 100 mg/day. In some embodiments, the BED ranges between about 0.5 mg/day and about 500 mg/day. In some embodiments, the BED is about 0.01, 0.05, 0.1, 0.25, 0.5, 0.75, 1, 2.5, 5, 7.5, 10, 25, 50, 75, 100, 250, 500, 750, 1000, 1500, 2000, 2500, 3000, 3500, 4000, 4500, or 5000 mg/day, or within a range defined by any two of the aforementioned values. In some embodiments, the BED is about 0.0015, 0.003, 0.006, 0.012, 0.024, 0.036, 0.048, 0.060, 0.072, 0.084, 0.096, 0.2, 0.25, 0.5, 0.75, 1, 2, 3, 6, 12, 18, 24, 30, 40, 50, 60, 70, 80, 90 or 100 mg/day, or within a range defined by any two of the aforementioned values.

In some embodiments, the BED ranges from about 0.01 mg/kg of body weight to about 1000 mg/kg. In some embodiments, the BED ranges between about 0.1 mg/kg and about 100 mg/kg. In some embodiments, the BED ranges between about 0.5 mg/kg and about 500 mg/kg. In some embodiments, the BED is about 0.01, 0.05, 0.1, 0.25, 0.5, 0.75, 1, 2.5, 5, 7.5, 10, 25, 50, 75, 100, 250, 500, 750, 1000, 1500, 2000, 2500, 3000, 3500, 4000, 4500, or 5000 mg/kg, or within a range defined by any two of the aforementioned values. In some embodiments, the BED is about 0.0015, 0.003, 0.006, 0.012, 0.024, 0.036, 0.048, 0.060, 0.072, 0.084, 0.096, 0.2, 0.25, 0.5, 0.75, 1, 2, 3, 6, 12, 18, 24, 30, 40, 50, 60, 70, 80, 90 or 100 mg/kg, or within a range defined by any two of the aforementioned values.

In some embodiments, the BED ranges from about 0.01 mg/m$^2$ of body surface area (BSA) to about 1000 mg/m$^2$. In some embodiments, the BED ranges between about 0.1 mg/m$^2$ and about 100 mg/m$^2$. In some embodiments, the BED ranges between about 0.5 mg/m$^2$ and about 500 mg/m². In some embodiments, the BED is about 0.01, 0.05, 0.1, 0.25, 0.5, 0.75, 1, 2.5, 5, 7.5, 10, 25, 50, 75, 100, 250, 500, 750, 1000, 1500, 2000, 2500, 3000, 3500, 4000, 4500, or 5000 mg/m², or within a range defined by any two of the aforementioned values. In some embodiments, the BED is about 0.0015, 0.003, 0.006, 0.012, 0.024, 0.036, 0.048, 0.060, 0.072, 0.084, 0.096, 0.2, 0.25, 0.5, 0.75, 1, 2, 3, 6, 12, 18, 24, 30, 40, 50, 60, 70, 80, 90 or 100 mg/m², or within a range defined by any two of the aforementioned values.

In some embodiments, the frequency of administration is normally daily. In some embodiments, the frequency of administration is once a week. In some embodiments, the frequency of administration is once every two weeks. In some embodiments, the frequency of administration is once every three weeks (e.g., Herceptin). In some embodiments, the frequency of administration can be dose is once every 6 months (e.g., Rituximab). In some embodiments, the frequency of administration can be adjusted as desired by one of ordinary skill in the art based on parameters such as the type of drug, the route of administration, the disease, and the like.

Other regimens of intravenous and oral Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) and Trametinib (Mekinist) have also been reported. Dosages must be adjusted in accord with objective indicator for regulating dosage, for example, evidence of antitumor activity, leukopenia or both. Total leukocyte count is a good, objective indicator for regulating dosage.

Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) is effective alone for susceptible malignancies. However, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) can be used concurrently or sequentially with one or more other antineoplastic drugs. When Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) is included in combined cytotoxic regimens, the doses of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) as well as that of the other drugs are adjusted accordingly as known to those of skill in the art.

The compositions, methods, systems and/or kits provided herein can be used for treating neoplasms. In some embodiments, the neoplasm is one or more types of brain cancer. Non-limiting examples of one or more types of brain cancer include glioblastoma, or any neoplasm associated with brain, astrocytomas (e.g., pilocytic astrocytoma, diffuse astrocytoma, anaplastic astrocytoma, and brain stem gliomas), glioblastomas (e.g., glioblastomas multiforme), meningioma, other gliomas (e.g., ependymomas, oligodendrogliomas, and mixed gliomas), and other brain tumors (e.g., pituitary tumors, craniopharyngiomas, germ cell tumors, pineal region tumors, medulloblastomas, and primary CNS lymphomas). See, cancercenter.com/brain-cancer/types/tab/overview/, which is hereby incorporated by reference in its entirety. In some embodiments, the neoplasms are sarcomas, non-small cell lung cancers, solid tumors with CNS metastatic disease. In some embodiments, the neoplasms are related to one or more types of neoplasm provided herein. -cell) leukemia, mycosis fungoides (advanced disease), neuroblastoma (disseminated disease), adenocarcinoma of the ovary, retinoblastoma, carcinoma of the breast, triple negative breast cancer, and biopsy-proven minimal change nephrotic syndrome in pediatrics patients who failed to adequately respond to or are unable to tolerate adrenocorticosteroid therapy.

Provided herein are combinations comprising, consisting of, or consisting essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and at least one modulator selected from the group consisting of quercetin, SPB and EGCG. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and quercetin. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and SPB. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and EGCG. The combinations can comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin, SPB and EGCG at any of the doses provided herein for each. In some embodiments, provided herein are combinations comprising, consisting of, or consisting essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and at least one modulator selected from the group consisting of quercetin, SPB and EGCG. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and quercetin. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and SPB. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and EGCG. The combinations can comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin, SPB and EGCG at any of the doses provided herein for each.

Also provided are combinations comprising, consisting of, or consisting essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and at least two modulators selected from the group consisting of quercetin, SPB and EGCG. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin and SPB. In some embodiments, the combination Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin and EGCG. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), SPB and EGCG. The combinations can comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin, SPB and EGCG at any of the doses provided herein for each. Also provided are combinations comprising, consisting of, or consisting essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and at least two modulators selected from the group consisting of quercetin, SPB and EGCG. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin and SPB. In some embodiments, the combination Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin and EGCG. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, SPB and EGCG. The combinations can comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin, SPB and EGCG at any of the doses provided herein for each.

In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and three modulators. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin, SPB and EGCG. The combinations can comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin, SPB and EGCG at any of the doses provided herein for each. In some embodiments, the combination comprises, consists of, or consists essentially of, one or more additional anti-cancer agents and one or more additional modulators. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and three modulators. In some embodiments, the combination comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin, SPB and EGCG. The combinations can comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin, SPB and EGCG at any of the doses provided herein for each. In some embodiments, the combination comprises, consists of, or consists essentially of, one or more additional anti-cancer agents and one or more additional modulators.

In some embodiments, the dose for the targeted therapies provided herein, is defined based on biological effective dose (BED). In some embodiments, the BED ranges from about 0.01 mg/day to about 1000 mg/day. In some embodiments, the BED ranges between about 0.1 mg/day and about 100 mg/day. In some embodiments, the BED ranges between about 0.5 mg/day and about 500 mg/day. In some embodiments, the BED is about 0.01, 0.05, 0.1, 0.25, 0.5, 0.75, 1, 2.5, 5, 7.5, 10, 25, 50, 75, 100, 250, 500, 750, 1000, 1500, 2000, 2500, 3000, 3500, 4000, 4500, or 5000 mg/day, or within a range defined by any two of the aforementioned values. In some embodiments, the BED is about 0.0015, 0.003, 0.006, 0.012, 0.024, 0.036, 0.048, 0.060, 0.072, 0.084, 0.096, 0.2, 0.25, 0.5, 0.75, 1, 2, 3, 6, 12, 18, 24, 30, 40, 50, 60, 70, 80, 90 or 100 mg/day, or within a range defined by any two of the aforementioned values.

In some embodiments, the BED ranges from about 0.01 mg/kg of body weight to about 1000 mg/kg. In some embodiments, the BED ranges between about 0.1 mg/kg and about 100 mg/kg. In some embodiments, the BED ranges between about 0.5 mg/kg and about 500 mg/kg. In some embodiments, the BED is about 0.01, 0.05, 0.1, 0.25, 0.5, 0.75, 1, 2.5, 5, 7.5, 10, 25, 50, 75, 100, 250, 500, 750, 1000, 1500, 2000, 2500, 3000, 3500, 4000, 4500, or 5000 mg/kg, or within a range defined by any two of the aforementioned values. In some embodiments, the BED is about 0.0015, 0.003, 0.006, 0.012, 0.024, 0.036, 0.048, 0.060, 0.072, 0.084, 0.096, 0.2, 0.25, 0.5, 0.75, 1, 2, 3, 6, 12, 18, 24, 30, 40, 50, 60, 70, 80, 90 or 100 mg/kg, or within a range defined by any two of the aforementioned values.

In some embodiments, the BED ranges from about 0.01 mg/m$^2$ of body surface area (BSA) to about 1000 mg/m$^2$. In some embodiments, the BED ranges between about 0.1 mg/m$^2$ and about 100 mg/m$^2$. In some embodiments, the BED ranges between about 0.5 mg/m$^2$ and about 500 mg/m$^2$. In some embodiments, the BED is about 0.01, 0.05, 0.1, 0.25, 0.5, 0.75, 1, 2.5, 5, 7.5, 10, 25, 50, 75, 100, 250, 500, 750, 1000, 1500, 2000, 2500, 3000, 3500, 4000, 4500, or 5000 mg/m$^2$, or within a range defined by any two of the aforementioned values. In some embodiments, the BED is about 0.0015, 0.003, 0.006, 0.012, 0.024, 0.036, 0.048, 0.060, 0.072, 0.084, 0.096, 0.2, 0.25, 0.5, 0.75, 1, 2, 3, 6, 12, 18, 24, 30, 40, 50, 60, 70, 80, 90 or 100 mg/m$^2$, or within a range defined by any two of the aforementioned values.

In some embodiments, the frequency of administration is normally daily. In some embodiments, the frequency of administration is once a week. In some embodiments, the frequency of administration is once every two weeks. In some embodiments, the frequency of administration is once every three weeks (e.g., Herceptin). In some embodiments, the frequency of administration can be dose is once every 6 months (e.g., Rituximab). In some embodiments, the frequency of administration can be adjusted as desired by one of ordinary skill in the art based on parameters such as the type of drug, the route of administration, the disease, and the like.

Doses of quercetin, SPB and EGCG for intravenous administration can be any one of the doses provided herein. For example, doses of quercetin for intravenous administration include, without limitations, 0.5 g to 1 g. Doses of SPB for intravenous administration include, without limitations, 5 g to 10 g. Doses of EGCG for intravenous administration include, without limitations, 0.1 g to 1.5 g.

In some embodiments, the any of the combinations herein are provided as compositions, methods and/or kits for preventing neoplasms in patients and/or treating neoplasms in patients. Any of the doses, routes of administration, frequency of administration, sequence of administration, etc. provided herein can be used for the components of the combinations.

The dose, route of administrations, mechanism of action, etc. of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) and Trametinib (Mekinist) are well-known in the art. The doses of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) and Trametinib (Mekinist) can be varied depending on, among other aspects, patient age, route of administration, neoplasm type, etc. The dose, route of administrations, mechanism of action, etc. of Temodar are well-known in the art. The doses of Temodar can be varied depending on, among other aspects, patient age, route of administration, neoplasm type, etc.

Nanoparticle Formulations

In some embodiments, the pharmaceutical formulation is formulated as one or more of a nanoparticle formulation, a liposomal formulation, or folic acid receptor conjugates. Nanoparticle formulations have many advantages over traditional dosage forms, such as enhanced dissolution properties and potential for efficient intracellular delivery of drugs. Nanoparticles have unique physical and chemical properties that offer several advantages as drug delivery carriers, or 'nano-carriers.' Nanoparticles-based composition for detection and/or treatment of cancers can comprise, consist of, or consist essentially of, nanoparticles in the form of, without limitations, quantum dots, magnetic nanoparticles, gold nanoshells (which are useful in detecting tumors and metastasis in many solid tumors), poly (lactide-co-glycolide) (PLGA)-based nanoparticles (e.g., PLGA/montmorillonite (PLGA/MMT) nanoparticles, Vitamin E-TPGS-emulsified PLGA nanoparticles, PLGA-mPEG nanoparticles), dendrimers, and SPIO and USPIO nanoparticles. See, Mousa S. A. and Bharali D. J., Nanotechnology-Based Detection and Targeted Therapy in Cancer: Nano-Bio Paradigms and Applications, *Cancers* (Basel), Vol. 3, No. 3, pp. 2888-2903, September 2011, which is hereby incorporated by reference in its entirety. Other nanoparticle-based examples are provided in Bharali D. J. and Mousa S. A., Emerging nanomedicines for early cancer detection and improved treatment: current perspective and future promise, *Pharmacology & Therapeutics*, Vol. 128, No. 2, pp. 324-335, November 2010, and Bharali D. J., et al., Nanoparticles and cancer therapy: a concise review with emphasis on dendrimers, *International Journal of Nanomedicine*, Vol. 4, pp. 1-7, Apr. 1, 2009, which are hereby incorporated by reference in their entirety. Pharmaceutical compositions can also be formulated as nano-micelles-based compositions, for example, as provided in U.S. Pat. No. 9,308,270 B2, which is hereby incorporated by reference in its entirety. Folic acid receptor conjugates based on a conjugating a molecule/drug with folic acid to form a "folate conjugate." Owing to the naturally high affinity of folate for the folate receptor protein commonly expressed on the surface of many human cancers, folate conjugates bind tightly to the folate receptor protein and trigger cellular uptake via endocytosis. Diverse molecules/drugs can be successfully delivered inside folate receptor protein expressing cells and tissues. Liposomal formulations comprise, consist of, or consist essentially of, liposomes that are used as vehicles for administration of drugs. Liposomes are most often composed of phospholipids, especially phosphatidylcholine, but may also include any lipids that are compatible with a lipid bilayer structure (e.g., as egg phosphatidylethanolamine). A liposomal formulation can comprise, consist of, or consist essentially of, liposomes that may employ surface ligands for attaching to unhealthy tissue. The major types of liposomes are multilamellar vesicle with several lamellar phase lipid bilayers, small unilamellar liposome vesicle with one lipid bilayer, large unilamellar vesicle, and cochleate vesicle.

In some embodiments, nanoparticle formulations are provided. The nanoparticle formulations comprise, consist of, or consist essentially of, one or more anti-cancer agents and/or one or more modulators, wherein the one or more anti-cancer agents and/or one or more modulators can be present in any dosage form, for example liquids for injection or oral administration, or pills or capsules. In some embodiments, the nanoparticles contain a single compound, i.e., one anti-cancer agent or one modulator (e.g., Rituximab (Rituxan), Ibrutinib (Imbruvica), Cetuximab (Erbitux) Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin, or SPB). In some embodiments, the nanoparticles contain two compounds (e.g., Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and quercetin, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and SPB, or quercetin and SPB. In some embodiments, the nanoparticles contain three compounds (e.g., Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin and SPB). In some embodiments, the nanoparticles contain a single compound, i.e., one anti-cancer agent or one modulator (e.g., Rituximab (Rituxan), Ibrutinib (Imbruvica), Cetuximab (Erbitux) Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin, or SPB). In some embodiments, the nanoparticles contain two compounds (e.g., Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and quercetin, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and SPB, or quercetin and SPB. In some embodiments, the nanoparticles contain three compounds (e.g., Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin and SPB).

In some embodiments, nanoparticle formulations comprise, consist of, or consist essentially of, at least one compound as nanoparticles. For example, in some embodiments, when nanoparticle formulations comprise, consist of, or consist essentially of, two compounds (e.g Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and quercetin, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and SPB, or quercetin and SPB), at least one compound is present as nanoparticles. In some embodiments, when nanoparticle formulations comprise, consist of, or consist essentially of, two compounds (e.g., Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and quercetin, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and SPB, or quercetin and SPB), both compounds are present as nanoparticles. In some embodiments, when nanoparticle formulations comprise, consist of, or consist essentially of, three compounds (e.g., Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin and SPB), at least one of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin, or SPB is present as nanoparticles. In some embodiments, when nanoparticle formulations comprise, consist of, or consist essentially of, three compounds (e.g., Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin and SPB), at least two of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin, or SPB are present as nanoparticles. In some embodiments, when nanoparticle formulations comprise, consist of, or consist essentially of, three compounds (e.g., Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist), quercetin and SPB), all three are present as nanoparticles. In some embodiments, nanoparticle formulations comprise, consist of, or consist essentially of, at least one compound as nanoparticles. For example, in some embodiments, when nanoparticle formulations comprise, consist of, or consist essentially of, two compounds (e.g Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and quercetin, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and SPB, or quercetin and SPB), at least one compound is present as nanoparticles. In some embodiments, when nanoparticle formulations comprise, consist of, or consist essentially of, two compounds (e.g., Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and quercetin, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and SPB, or quercetin and SPB), both compounds are present as nanoparticles. In some embodiments, when nanoparticle formulations comprise, consist of, or consist essentially of, three compounds (e.g., Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin and SPB), at least one of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin, or SPB is present as nanoparticles. In some embodiments, when nanoparticle formulations comprise, consist of, or consist essentially of, three compounds (e.g., Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin and SPB), at least two of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin, or SPB are present as nanoparticles. In some embodiments, when nanoparticle formulations comprise, consist of, or consist essentially of, three compounds (e.g., Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination, quercetin and SPB), all three are present as nanoparticles.

In some embodiments, nanoparticle formulations comprise, consist of, or consist essentially of, nanoparticles containing a single compound, i.e., one anti-cancer agent or one modulator (e.g., nano-Rituximab (Rituxan), -Ibrutinib (Imbruvica), -Cetuximab (Erbitux), -Crizotinib (Xalkori), -Ceritinib (Zykadia), -Trastuzumab (Herceptin), -Everolimus (Afinitor), -Afatinib (Gilotrif), -Bevacizumab (Avastin) or -Trametinib (Mekinist), nano-quercetin, or nano-SPB). In some embodiments, nanoparticle formulations comprise, consist of, or consist essentially of, nanoparticles containing two compounds (e.g., nano-Rituximab (Rituxan), -Ibrutinib (Imbruvica), -Cetuximab (Erbitux), -Crizotinib (Xalkori), -Ceritinib (Zykadia), -Trastuzumab (Herceptin), -Everolimus (Afinitor), -Afatinib (Gilotrif), -Bevacizumab (Avastin) or -Trametinib (Mekinist) and nano-quercetin, nano-Rituximab (Rituxan), -Ibrutinib (Imbruvica), -Cetuximab (Erbitux), -Crizotinib (Xalkori), -Ceritinib (Zykadia), -Trastuzumab (Herceptin), -Everolimus (Afinitor), -Afatinib (Gilotrif), -Bevacizumab (Avastin) or -Trametinib (Mekinist) and nano-SPB, or nano-quercetin and nano-SPB). In some embodiments, nanoparticle formulations comprise, consist of, or consist essentially of, nanoparticles containing three compounds (e.g., nano-Rituximab (Rituxan), -Ibrutinib (Imbruvica), -Cetuximab (Erbitux), -Crizotinib (Xalkori), -Ceritinib (Zykadia), -Trastuzumab (Herceptin), -Everolimus (Afinitor), -Afatinib (Gilotrif), -Bevacizumab (Avastin) or -Trametinib (Mekinist), nano-quercetin and nano-SPB). In some embodiments, nanoparticle formulations comprise, consist of, or consist essentially of, nanoparticles containing a single compound, i.e., one anti-cancer agent or one modulator (e.g., nano-Rituximab (Rituxan), -Ibrutinib (Imbruvica), -Cetuximab (Erbitux), -Crizotinib (Xalkori), -Ceritinib (Zykadia), -Trastuzumab (Herceptin), -Everolimus (Afinitor), -Afatinib (Gilotrif), -Bevacizumab (Avastin), -Trametinib (Mekinist), or -Trametinib (Mekinist)-Temodar combination, nano-quercetin, or nano-SPB). In some embodiments, nanoparticle formulations comprise, consist of, or consist essentially of, nanoparticles containing two compounds (e.g., nano-Rituximab (Rituxan), -Ibrutinib (Imbruvica), -Cetuximab (Erbitux), -Crizotinib (Xalkori), -Ceritinib (Zykadia), -Trastuzumab (Herceptin), -Everolimus (Afinitor), -Afatinib (Gilotrif), -Bevacizumab (Avastin), -Trametinib (Mekinist), or -Trametinib (Mekinist)-Temodar combination and nano-quercetin, nano-Rituximab (Rituxan), -Ibrutinib (Imbruvica), -Cetuximab (Erbitux), -Crizotinib (Xalkori), -Ceritinib (Zykadia), -Trastuzumab (Herceptin), -Everolimus (Afinitor), -Afatinib (Gilotrif), -Bevacizumab (Avastin), -Trametinib (Mekinist), or -Trametinib (Mekinist)-Temodar combination and nano-SPB, or nano-quercetin and nano-SPB). In some embodiments, nanoparticle formulations comprise, consist of, or consist essentially of, nanoparticles containing three compounds (e.g., nano-Rituximab (Rituxan), -Ibrutinib (Imbruvica), -Cetuximab (Erbitux), -Crizotinib (Xalkori), -Ceritinib (Zykadia), -Trastuzumab (Herceptin), -Everolimus (Afinitor), -Afatinib (Gilotrif), -Bevacizumab (Avastin), -Trametinib (Mekinist), or -Trametinib (Mekinist)-Temodar combination, nano-quercetin and nano-SPB).

In some embodiments, provided herein are nanoparticle formulations for preventing and/or treating one or more neoplasms. Non-limiting examples of neoplasms include breast adenocarcinoma, pancreatic adenocarcinoma, lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, bladder cancer, hematological malignancies, squamous cell carcinomas, breast cancer, glioblastoma, or any neoplasm associated with brain including, but not limited to, astrocytomas (e.g., pilocytic astrocytoma, diffuse astrocytoma, anaplastic astrocytoma, and brain stem gliomas), glioblastomas (e.g., glioblastomas multiforme), meningioma, other gliomas (e.g., ependymomas, oligodendrogliomas, and mixed gliomas), and other brain tumors (e.g., pituitary tumors, craniopharyngiomas, germ cell tumors, pineal region tumors, medulloblastomas, and primary CNS lymphomas) (See, cancercenter.com/brain-cancer/types/tab/overview/, which is hereby incorporated by reference in its entirety). In some embodiments, the neoplasm is related to one or more types of neoplasm provided herein.

In some embodiments, nanoparticles comprise, consist of, or consist essentially of, one or more of quercetin, sodium phenyl butyrate, and a chemotherapeutic agent. In some embodiments, nanoparticle formulations comprise, consist of, or consist essentially of, a combination of nanoparticles wherein a first population of nanoparticles contains quercetin, and a second population of nanoparticles contains a chemotherapeutic agent. In some embodiments, a third population of nanoparticles contains SPB. In some embodiments, the formulation comprises, consists of, or consists essentially of, a first population of nanoparticles containing quercetin, and a second population of nanoparticles containing SPB. In some embodiments, the formulation comprises, consists of, or consists essentially of, a first population of nanoparticles containing a chemotherapeutic agent, and a second population of nanoparticles containing SPB. In some of these embodiments, one or more additional compounds, e.g., chemotherapeutic agent, anticancer agent, modulator (e.g. quercetin or SPB), etc., that are not in a nanoparticle formulation are added to the nanoparticle formulation. In some embodiments, the chemotherapeutic agent is Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist). In some embodiments, the chemotherapeutic agent is Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination.

In some embodiments, the nanoparticle formulation comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and quercetin in a nanoparticle, or a combination of a first population of nanoparticles containing Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and a second population of nanoparticles containing quercetin. Without being limited by any theory, it is believed that the nanoparticles are expected to improve the ability of a compound to cross the blood brain barrier. For example, in a nanoparticle formulation comprising, consisting of, or consisting essentially of, a combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and quercetin in a single nanoparticle or in two separate nanoparticle populations, it is expected that the nanoparticles will improve the ability of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and quercetin to cross the blood brain barrier. In some embodiments, the nanoparticle formulation comprises, consists of, or consists essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and quercetin in a nanoparticle, or a combination of a first population of nanoparticles containing Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and a second population of nanoparticles containing quercetin. Without being limited by any theory, it is believed that the nanoparticles are expected to improve the ability of a compound to cross the blood brain barrier. For example, in a nanoparticle formulation comprising, consisting of, or consisting essentially of, a combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and quercetin in a single nanoparticle or in two separate nanoparticle populations, it is expected that the nanoparticles will improve the ability of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination and quercetin to cross the blood brain barrier.

In some embodiments, the nanoparticles can be one or more nanospheres, nanocylinders, nanoplates, nanoshells, nanorods, nanorices, nanofibers, nanowires, nanopyramids, nanoprisms, nanostars, nanocrescents, nanorings, and nanoantennas. In some embodiments, the dimensions of the nanoparticles can range from about 1 nm to about 100 nm. In some embodiments, the dimensions of the nanoparticles can range from about 100 nm to about 250 nm. In some embodiments, the dimensions of the nanoparticles can range from about 20 nm to about 1000 nm. In some embodiments, the dimensions of the nanoparticles can range from about 4 nm to about 6250 nm. In some embodiments, the dimensions of the nanoparticles is about 1, 5, 10, 20, 30, 40, 50, 60, 70, 80, 90, 100, 200, 300, 400, 500, 750, 1000, 1250, 2500, 3750, 5000, 7500, 10000 nm, or a value within a range defined by any two of the aforementioned values. In some embodiments, the amount of modulator and/or the amount of anti-cancer agent that can be incorporated within a nanoparticle depends on the size of the nanoparticle. Thus, the greater the size of a nanoparticle, the greater the amount of one or more modulators and/or anti-cancer agent that can be incorporated within the nanoparticle.

In some embodiments, the nanoparticles comprise, consist of, or consist essentially of, one or more stabilizers, which comprise, consist of, or consist essentially of, the structural components of the nanoparticle. Non-limiting examples of stabilizers include deoxycholic acid, polyvinyl alcohol (PVA), Polyvinylpyrrolidone (PVP), and polyethylene glycol (PEG). Stabilizers and their use in the production of nanoparticles are well known to one of ordinary skill in the art. In some embodiments, physico-chemical characterization of nanoparticles is well known to one of ordinary skill in the art. For example, in some embodiments, the heterogeneity of sizes (molecular weight) of the nanoparticles can be measured by determining the dispersity of the nanoparticles, which can be expressed in terms of the polydispersity index (PDI).

In some embodiments, the nanoparticles are conjugate to one or more small molecules (e.g. folic acid). In some embodiments, the one or more small molecules allow for the nanoparticles to be specifically taken up by target cells (e.g., brain cancer cells). Without being bound by any theory, enhanced expression of folic acid receptor is commonly found on cancer cells. Therefore, conjugating nanoparticles to folic acid can selectively enhance the uptake of the nanoparticles by cancer cells (e.g., FIG. 18). One of ordinary skill in the art can select a conjugate for modifying a nanoparticle based on the cancer(s) to be targeted. For example, in some embodiment, two or more conjugates can be used to modify a nanoparticle to specifically target the nanoparticle to more than one type of cancer.

In some embodiments, additional treatment options can be combined with the one or more combinations disclosed herein. For example, radiation therapy can be provided and/or radiosurgery can be performed. Non-limiting examples include whole brain radiation therapy, Gamma knife, and Cyberknife. Thus, for example, in some embodiments, subjects with recurrent and/or refractory glioblastoma can be treated with a combination of nano-Quercetin (e.g., nanospheres with Quercetin) administered intravenously and Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination administered orally along with Leading Edge® Gamma Knife Technique radiation therapy.

Additional Embodiments

In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+Quercetin, wherein Quercetin is administered intravenously, wherein the concentration of Quercetin in a solution for intravenous administration is about 5 mg/ml to about 500 mg/ml, and wherein Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is administered intravenously, wherein the Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is in a solution for intravenous administration.

In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+Quercetin, wherein Quercetin is administered intravenously, wherein the dose of Quercetin in a solution for intravenous administration is about 0.05 g to about 10 g, and wherein Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is administered intravenously, wherein the Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is in a solution for intravenous administration.

In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+Quercetin, wherein Quercetin is administered orally, wherein the amount of Quercetin in a composition for oral administration is about 100 mg to about 50 g, and wherein Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is administered orally, wherein the Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is in a composition for oral administration.

In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+Quercetin, wherein Quercetin is administered in a liposomal formulation, wherein the dose of Quercetin for administration in a liposomal formulation is about 25 mg a day to about 100 mg a day, and wherein Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is either administered intravenously, wherein the Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is in a solution for intravenous administration, or wherein Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is administered orally, wherein the Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is in a composition for oral administration.

In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+SPB, wherein SPB is administered intravenously, wherein the concentration of SPB in a solution for intravenous administration is about 20 mg/ml to about 2000 mg/ml, and wherein Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is administered intravenously, wherein the Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is in a solution for intravenous administration.

In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+SPB, wherein SPB is administered intravenously, wherein the dose of SPB in a solution for intravenous administration is about 0.5 g to about 100 g, and wherein Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is administered intravenously, wherein the Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is in a solution for intravenous administration.

In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+SPB, wherein SPB is administered orally, wherein the amount of SPB in a composition for oral administration is about 0.1 g to about 50 g, and wherein Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is administered orally, wherein the Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is in a composition for oral administration.

In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+EGCG, wherein EGCG is administered intravenously, wherein the concentration of EGCG in a solution for intravenous administration is about 5 mg/ml to about 100 mg/ml, and wherein Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is administered intravenously, wherein the Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is in a solution for intravenous administration.

In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+EGCG, wherein EGCG is administered intravenously, wherein the dose of EGCG in a solution for intravenous administration is at a dose of about 0.01 g to about 15 g, and wherein Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is administered intravenously, wherein the Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is in a solution for intravenous administration.

In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+EGCG, wherein EGCG is administered orally, wherein the amount of EGCG in a composition for oral administration is about 0.1 g to about 3 g, and wherein Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is administered orally, wherein the Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination is in a composition for oral administration.

In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+Quercetin+SPB. In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+Quercetin+EGCG. In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+SPB+EGCG. In some embodiments, the combinations in the compositions, and the compositions for the kits, uses and/or methods described herein comprise, consist of, or consist essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), Trametinib (Mekinist), or Trametinib (Mekinist)-Temodar combination+Quercetin+SPB+EGCG.

In some embodiments, wherein the anticancer agent the combinations in the compositions, and the compositions for the kits, uses and/or methods described herein comprising, consisting of, consisting essentially of, the Trametinib (Mekinist)-Temodar combination, the Trametinib (Mekinist) can be in a solution for intravenous administration or in a composition for oral administration, and independently the Temodar can be in a solution for intravenous administration or in a composition for oral administration.

The formulations of compositions and compositions for the kits, uses and/or methods described herein include but are not limited to the combinations provided in Table 0.3 below.

TABLE 0.3

Combinations for formulations of compositions and compositions for the kits, uses and/or methods described herein

| | Combination | | | |
|---|---|---|---|---|
| | Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatanib (Gilotrif), Bevacizumab (Avastin), Trametinib (Mekinist), or Trametinib (Mekinist)-Temodar combination (Oral) | Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatanib (Gilotrif), Bevacizumab (Avastin), Trametinib (Mekinist), or Trametinib (Mekinist)-Temodar combination (IV) | Quercetin | |
| | | | IV; about 5 mg/ml to about 500 mg/ml | IV; about 0.05 g to about 10 g |
| 1. | X | | | |
| 2. | X | | | |
| 3. | X | | | |
| 4. | X | | | |
| 5. | X | | | |
| 6. | X | | | |
| 7. | X | | | |
| 8. | X | | | |
| 9. | X | | | |
| 10. | X | | | |
| 11. | X | | | |
| 12. | X | | X | |
| 13. | X | | | X |
| 14. | X | | | |
| 15. | X | | | |
| 16. | X | | | |
| 17. | X | | | |
| 18. | X | | | |
| 19. | X | | X | |
| 20. | X | | X | |
| 21. | X | | | |
| 22. | X | | X | |
| 23. | X | | X | |
| 24. | X | | | |
| 25. | X | | | X |
| 26. | X | | | X |
| 27. | X | | | X |
| 28. | X | | | X |
| 29. | X | | | |
| 30. | X | | | |
| 31. | X | | | |
| 32. | X | | | |
| 33. | X | | X | |
| 34. | X | | X | |
| 35. | X | | X | |
| 36. | X | | X | |
| 37. | X | | | X |
| 38. | X | | | X |
| 39. | X | | | X |
| 40. | X | | | X |
| 41. | | X | | |
| 42. | | X | | |
| 43. | | X | | |

TABLE 0.3-continued

Combinations for formulations of compositions and compositions for the kits, uses and/or methods described herein

| | | | | |
|---|---|---|---|---|
| 44. | X | | | |
| 45. | X | | | |
| 46. | X | | | |
| 47. | X | | | |
| 48. | X | | | |
| 49. | X | | | |
| 50. | X | | | |
| 51. | X | | | |
| 52. | X | X | | |
| 53. | X | X | | X |
| 54. | X | | | |
| 55. | X | | | |
| 56. | X | | | |
| 57. | X | | | |
| 58. | X | | | |
| 59. | X | X | | |
| 60. | X | X | | |
| 61. | X | | | |
| 62. | X | X | | |
| 63. | X | X | | |
| 64. | X | | | |
| 65. | X | | | X |
| 66. | X | | | X |
| 67. | X | | | X |
| 68. | X | | | X |
| 69. | X | | | |
| 70. | X | | | |
| 71. | X | | | |
| 72. | X | | | |
| 73. | X | X | | |
| 74. | X | X | | |
| 75. | X | X | | |
| 76. | X | X | | |
| 77. | X | | | X |
| 78. | X | | | X |
| 79. | X | | | X |
| 80. | X | | | X |

| | Combination | | | | | | | |
|---|---|---|---|---|---|---|---|---|
| | Quercetin | | SPB | | | EGCG | | |
| | Oral; about 100 mg to about 50 g | Liposomal; about 25 mg a day to about 100 mg a day | IV; about 20 mg/ml to about 2000 mg/ml | IV; about 0.5 g to about 100 g | Oral; about 0.1 g to about 50 g | IV: about 5 mg/ml to about 100 mg/ml | IV; about 0.01 g to about 15 g | Oral; about 0.1 g to about 3 g |
| 1. | X | | | | | | | |
| 2. | | X | | | | | | |
| 3. | | | | | X | | | |
| 4. | | | | | | | | X |
| 5. | X | | | | X | | | |
| 6. | X | | | | | | | X |
| 7. | | | | | X | | | X |
| 8. | X | | | | X | | | X |
| 9. | | X | | | X | | | |
| 10. | | X | | | | | | X |
| 11. | | X | | | X | | | X |
| 12. | | | | | | | | |
| 13. | | | | | | | | |
| 14. | | X | | | | | | |
| 15. | | | X | | | | | |
| 16. | | | | X | | | | |
| 17. | | | | | | X | | |
| 18. | | | | | | | X | |
| 19. | | | X | | | | | |
| 20. | | | | | | X | | |
| 21. | | | X | | | X | | |
| 22. | | | | X | | | | |
| 23. | | | | | | | X | |
| 24. | | | | X | | | X | |
| 25. | | | X | | | | | |
| 26. | | | | | | X | | |
| 27. | | | | X | | | | |
| 28. | | | | | | | X | |

TABLE 0.3-continued

Combinations for formulations of compositions and compositions for the kits, uses and/or methods described herein

| # | 1 | 2 | 3 | 4 | 5 | 6 |
|---|---|---|---|---|---|---|
| 29. | X | X | | | | |
| 30. | X | | | X | | |
| 31. | X | | X | | | |
| 32. | X | | | | X | |
| 33. | | X | | X | | |
| 34. | | X | | | X | |
| 35. | | | X | X | | |
| 36. | | | X | | X | |
| 37. | | X | | X | | |
| 38. | | X | | | X | |
| 39. | | | X | X | | |
| 40. | | | X | | X | |
| 41. | X | | | | | |
| 42. | | X | | | | |
| 43. | | | | X | | |
| 44. | | | | | | X |
| 45. | X | | | X | | |
| 46. | X | | | | | X |
| 47. | | | | X | | X |
| 48. | X | | | X | | X |
| 49. | | X | | X | | |
| 50. | | X | | | | X |
| 51. | | X | | X | | X |
| 52. | | | | | | |
| 53. | | | | | | |
| 54. | | X | | | | |
| 55. | | | X | | | |
| 56. | | | | X | | |
| 57. | | | | | X | |
| 58. | | | | | | X |
| 59. | | | X | | | |
| 60. | | | | | X | |
| 61. | | | X | | X | |
| 62. | | | | X | | |
| 63. | | | | | | X |
| 64. | | | | X | | X |
| 65. | | | X | | | |
| 66. | | | | | X | |
| 67. | | | | X | | |
| 68. | | | | | | X |
| 69. | | X | X | | | |
| 70. | | X | | | X | |
| 71. | | X | | X | | |
| 72. | | X | | | | X |
| 73. | | | X | | X | |
| 74. | | | X | | | X |
| 75. | | | | X | X | |
| 76. | | | | X | | X |
| 77. | | | X | | X | |
| 78. | | | X | | | X |
| 79. | | | | X | X | |
| 80. | | | | X | | X |

In Table 0.3, "X" indicates the components of the combinations for formulations of compositions and compositions for the kits, uses and/or methods described herein. The dosing of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin), or Trametinib (Mekinist), can be, but is not limited to, a BED range of about 0.01 mg/day to about 1000 mg/day, a BED range of about 0.01 mg/kg of body weight to about 1000 mg/kg, or a BED range of about 0.01 mg/m$^2$ of body surface area (BSA) to about 1000 mg/m$^2$. Intravenous dosing of Temodar can be, but is not limited to, 40 mg/kg to 50 mg/kg in divided doses over a period of 2 to 5 days, or 10 mg/kg to 15 mg/kg every 7 to 10 days, or 3 mg/kg to 5 mg/kg twice weekly. Oral dosing Temodar can be, but is not limited to, 1 mg per kg per day to 5 mg per kg per day, or 1 mg/kg/day to 5 mg/kg/day, or 2 mg/kg/day for 8 to 12 weeks (maximum cumulative dose 168 mg per kg). In some embodiments, including those in Table 0.3, in a combination comprising Quercetin and SPB, the ratio of the concentration and/or dosing of Quercetin and SPB ranges from about 1:2 to about 1:30. In some embodiments, including those in Table 0.3, in a combination comprising Quercetin and SPB, the ratio of the concentration and/or dosing of Quercetin and SPB is about 1:10. In some embodiments, including those in Table 0.3, in a combination comprising Quercetin and SPB, the ratio of the concentration and/or dosing of Quercetin and SPB is about 1:1.25, 1:1.5, 1:1.75, 1:2, 1:4, 1:6, 1:8, 1:10, 1:12, 1:14, 1:16, 1:18, 1:20, 1:22, 1:24, 1:26, 1:28, 1:30, 1:32, 1:34, 1:36, 1:38, 1:40, or a ratio within a range defined by any two of the aforementioned ratios.

In some embodiments, including but not limited to those in Table 0.3, the dose of Quercetin ranges from about 0.5 g to about 2 g. In some embodiments, the dose of quercetin is about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 or 10 g, or within a range defined by any two of the aforementioned values. In some embodiments, the dose of SPB ranges from about 1 g to 15 g. In some embodiments, SPB is administered orally at a dose of about 0.2, 0.3, 0.4, 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, or 75 g, or within a range defined by any two of the aforementioned values.

EXAMPLES

The following Examples are non-limiting. The concentrations and doses of the anti-cancer agents and modulators disclosed in the following Examples are non-limiting. Other acceptable concentrations, ranges of concentrations, doses or ranges of doses are also contemplated.

Example 1—Synthesis and Characterization of Nanoparticles

Several nanoparticles (NPs) were synthetized and characterized. PLGA-PEG-NPs, FA-PLGA-PEG-NPs, DSPE-PEG-NPs and FA-DSPE-PEG-NPs encapsulating quercetin were synthesized. The corresponding void nanoparticles (without encapsulating quercetin) were synthesized as controls. During the process of nanoparticles synthesis, various parameters such as different types of stabilizers, amount of stabilizer, amount of drug (quercetin), etc. were tested.

While PLGA-PEG and DSPE-PEG are commercially available, PLGA-PEG conjugated to folic acid was synthesized using carbodiimide chemistry. The nanoparticles were characterized using Dynamic Light Scattering (DLS), UV-Vis-spectrophotometer. FIG. 1-FIG. 7 show graphs showing size distribution of the different nanoparticles.

Example 2-Example 5

As described in Example 2-Example 5, before choosing the nanoformulation for in vitro and/or in vivo studies, different parameters that determine the size, amount of encapsulating drug (quercetin), stability, etc. of nanoparticles were explored. During this process, nanoparticles of different sizes were synthesized, for example, ranging from about 100 nm to about 250 nm in diameter. Different type of stabilizer like Polyvinyl alcohol (PVA), deoxycholic acid were used to explore the synthesis of the nanoformulations.

Example 2

Figure 8:
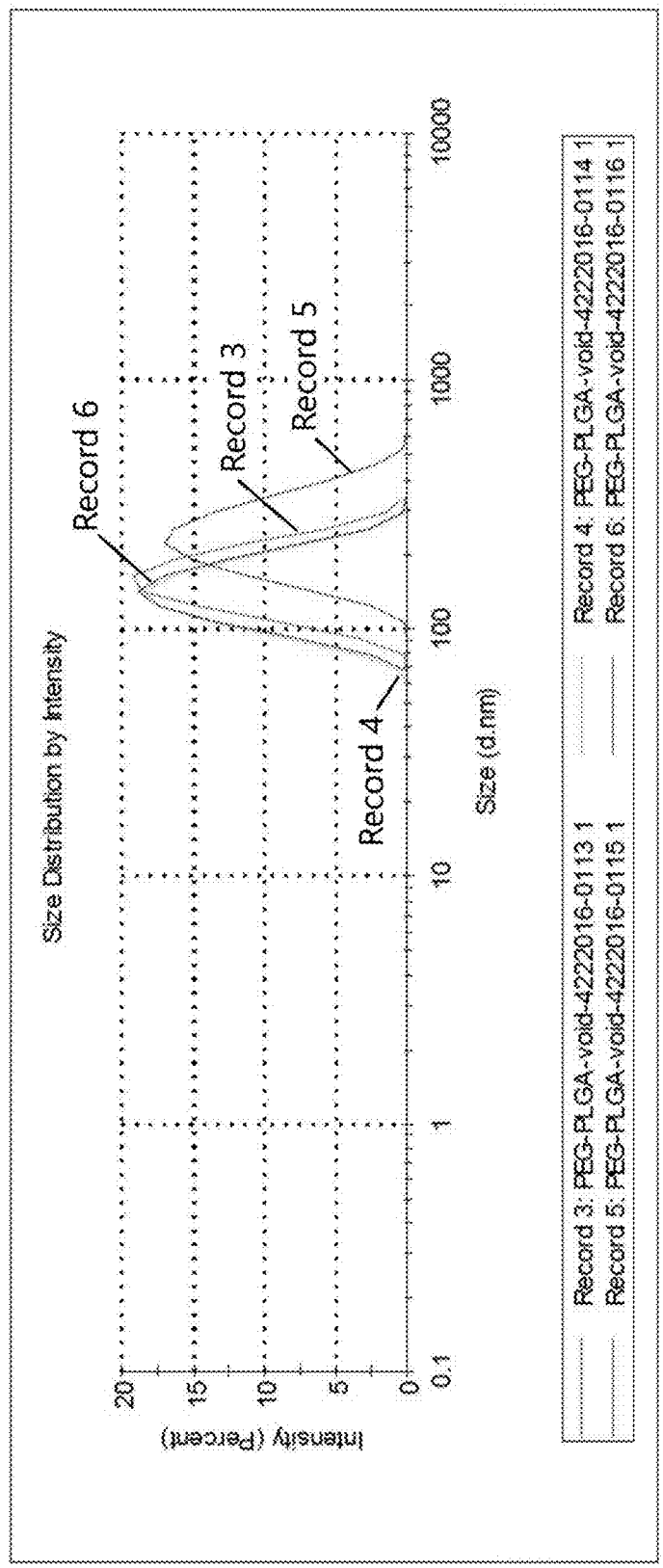
FIG. 8 shows synthesis of an embodiment of Void-PLGA-PEG nanoparticles using polyvinyl alcohol as a stabilizer (See, Example 2).

Data related to synthesis of different batches of Void-PLGA-PEG nanoparticles using polyvinyl alcohol as a stabilizer are provided (FIG. 8; TABLE 3).

TABLE 3

| Record | Sample Name | Size (Z avg diameter in nm) | PDI |
| --- | --- | --- | --- |
| 3 | PEG-PLGA-void-4222016-0013 | 150.9 | 0.69 |
| 4 | PEG-PLGA-void-4222016-0014 | 133.3 | 0.073 |
| 5 | PEG-PLGA-void-4222016-0015 | 220.2 | 0.152 |
| 6 | PEG-PLGA-void-4222016-0016 | 135.8 | 0.076 |

Example 3

Figure 9:
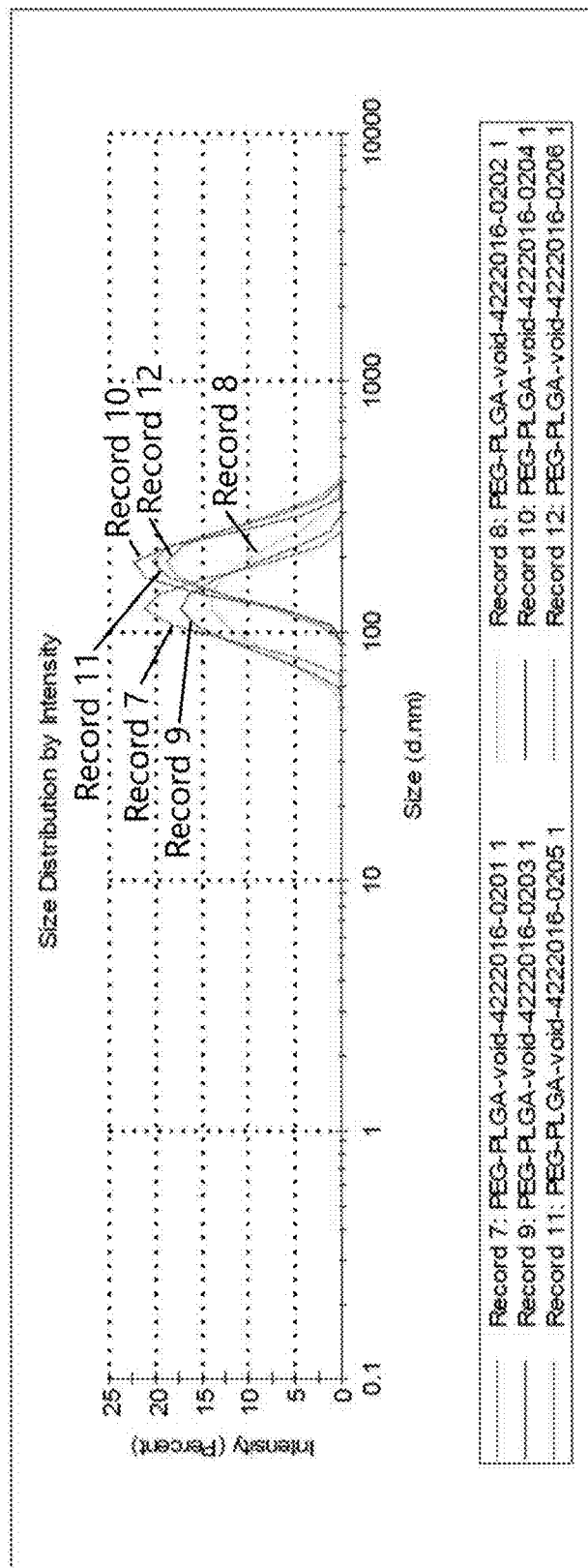
FIG. 9 shows synthesis of an embodiment of Void-PLGA-PEG nanoparticles using deoxycholic acid as a stabilizer (See, Example 3).

Data related to synthesis of different batches of Void-PLGA-PEG nanoparticles using deoxycholic acid as a stabilizer. Various amount of PLGA-PEG and deoxycholic acid was used to synthesized the nanoparticles are provided (FIG. 9; TABLE 4). Record 8 was selected to be tested further in in vitro/in vivo studies.

TABLE 4

| Record | Sample Name | Size (Z avg diameter in nm) | PDI |
| --- | --- | --- | --- |
| 7 | PEG-PLGA-void-4222016-0201 | 123.5 | 0.039 |
| 8 | PEG-PLGA-void-4222016-0202 | 127.1 | 0.124 |
| 9 | PEG-PLGA-void-4222016-0203 | 120.2 | 0.088 |
| 10 | PEG-PLGA-void-4222016-0204 | 179.6 | 0.040 |
| 11 | PEG-PLGA-void-4222016-0205 | 184.9 | 0.059 |
| 12 | PEG-PLGA-void-4222016-0206 | 184.3 | 0.062 |

Example 4—Exploration of Amount of Quercetin in the Nanofomulations

Figure 10:
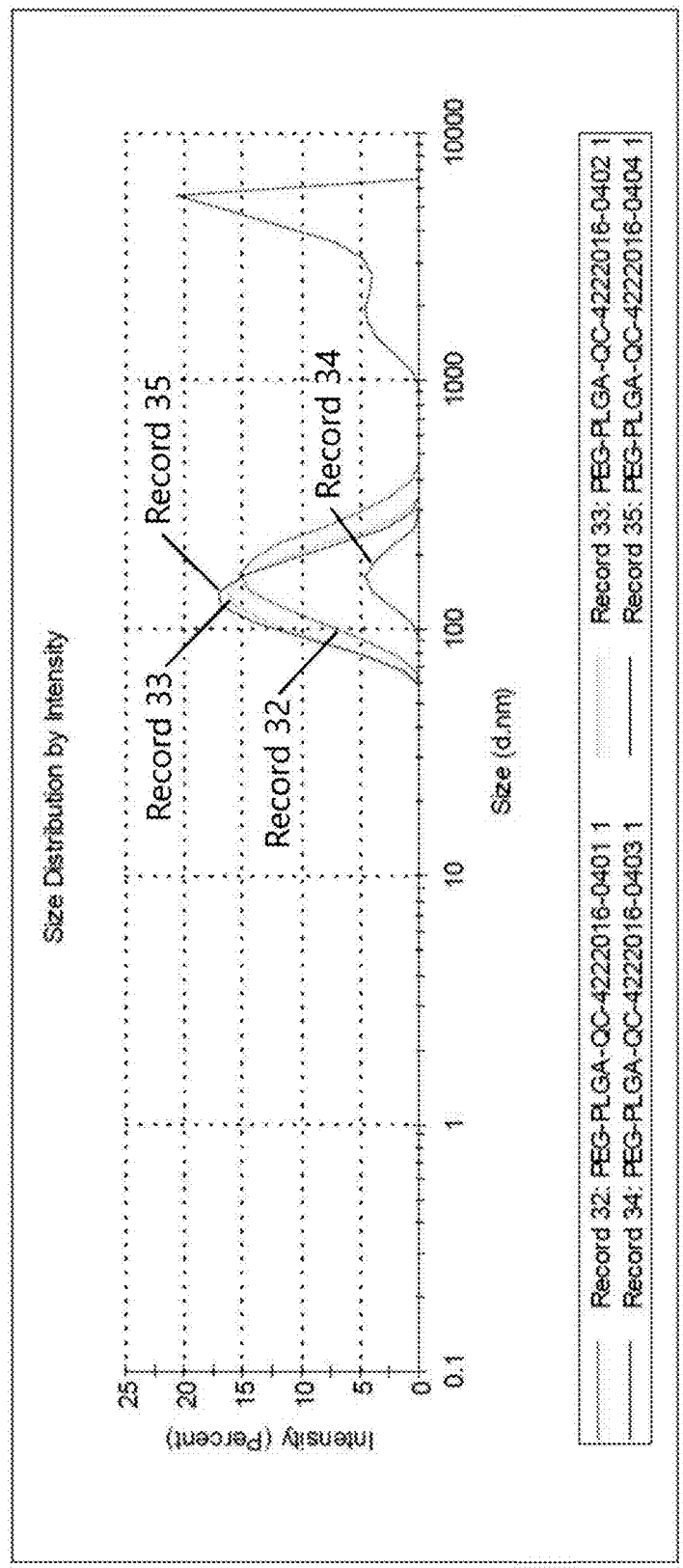
FIG. 10 shows synthesis and optimization of an embodiment of PLGA-PEG nanoparticles encapsulating quercetin (See, Example 4).

Data related to synthesis and exploration of different batches of PLGA-PEG nanoparticles encapsulating quercetin are provided. Deoxycholic acid was used as a stabilizer. Different ratios quercetin: PLGA-PEG were used to explore the synthesize process of the nanoparticles (FIG. 10; TABLE 5). Record 33 was selected to be tested further in in vitro/in vivo studies.

TABLE 5

| Record | Sample Name | Size (Z avg diameter in nm) | PDI |
| --- | --- | --- | --- |
| 32 | PEG-PLGA-QC-4222016-0401 | 154.9 | 0.115 |
| 33 | PEG-PLGA-QC-4222016-0402 | 132.8 | 0.093 |
| 34 | PEG-PLGA-QC-4222016-0403 | 2513 | 0.688 |
| 35 | PEG-PLGA-QC-4222016-0404 | 130.1 | 0.092 |

Example 5—DSPE-PEG-NPs Synthesis and Characterization

Figure 11:
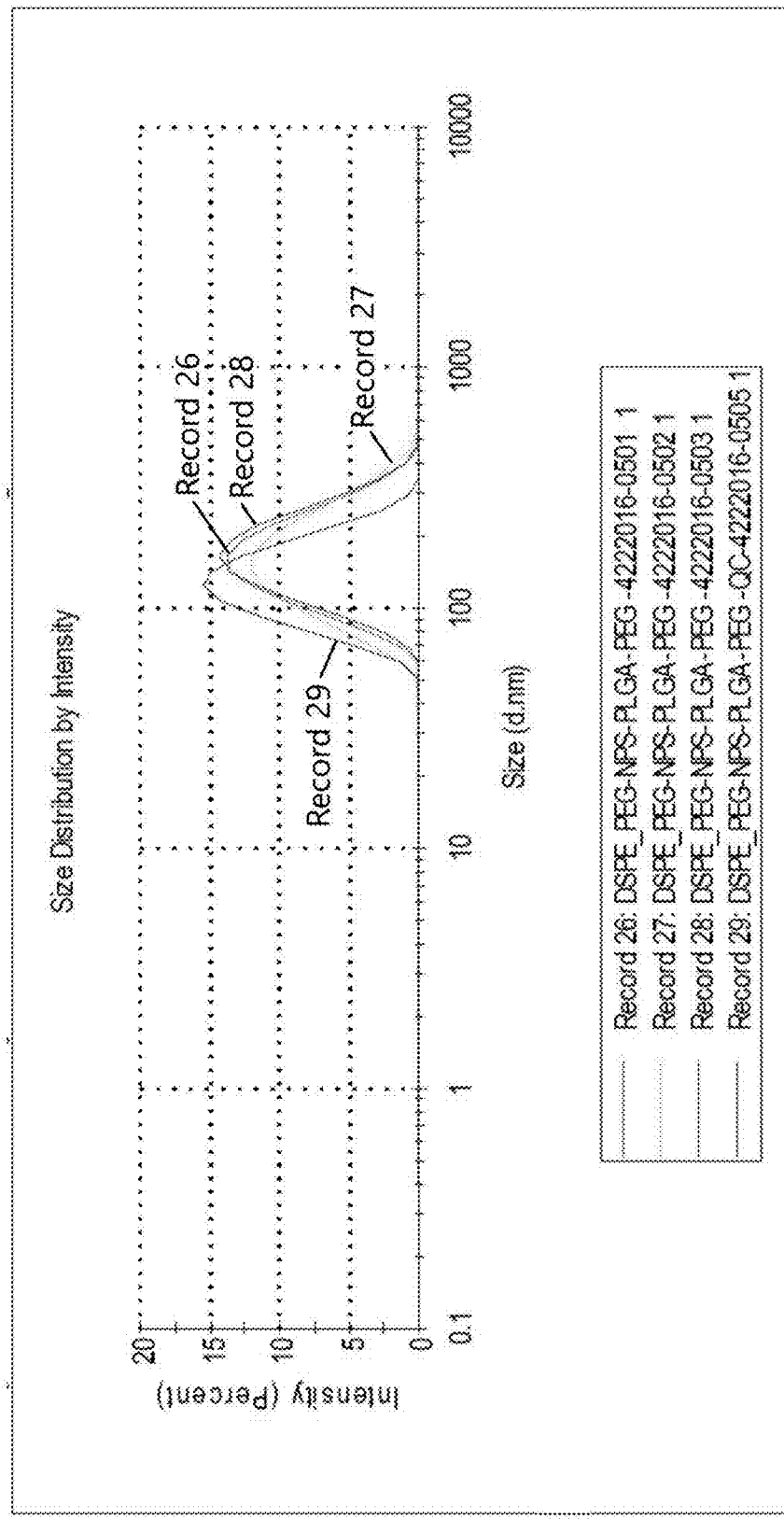
FIG. 11 shows synthesis and optimization of an embodiment of DSPE-PEG-NPs (See, Example 5).

Similar to Example 4, the method for the synthesis of different batches of DSPE-PEG-NPs was optimized (FIG. 11; TABLE 6). Record 29 was selected to be tested further in in vitro/in vivo studies.

TABLE 6

| Record | Sample Name | Size (Z avg diameter in nm) | PDI |
| --- | --- | --- | --- |
| 26 | DSPE-PEG/PEG-PLGA-4222016-0501 | 150.0 | 0.115 |
| 27 | DSPE-PEG/PEG-PLGA-4222016-0502 | 141.4 | 0.161 |
| 28 | DSPE-PEG/PEG-PLGA-4222016-0503 | 152.2 | 0.171 |
| 29 | DSPE-PEG/PEG-PLGA-4222016-0505 | 120.2 | 0.108 |

Example 6—Confocal Imaging of the Nanoparticles in Cancer Cells

PLGA-PEG-NPS, DSPE-PEG-NPS, FA-PEG-NPS and FA-DSPE-PEG-NPS particles labeled with a dye (Cy5) were synthesized. These nanoparticles were used to examine the preferential uptake of the nanoparticles with or without folic acid in a cancer cell line that overexpress the folic acid receptor.

Figure 18:
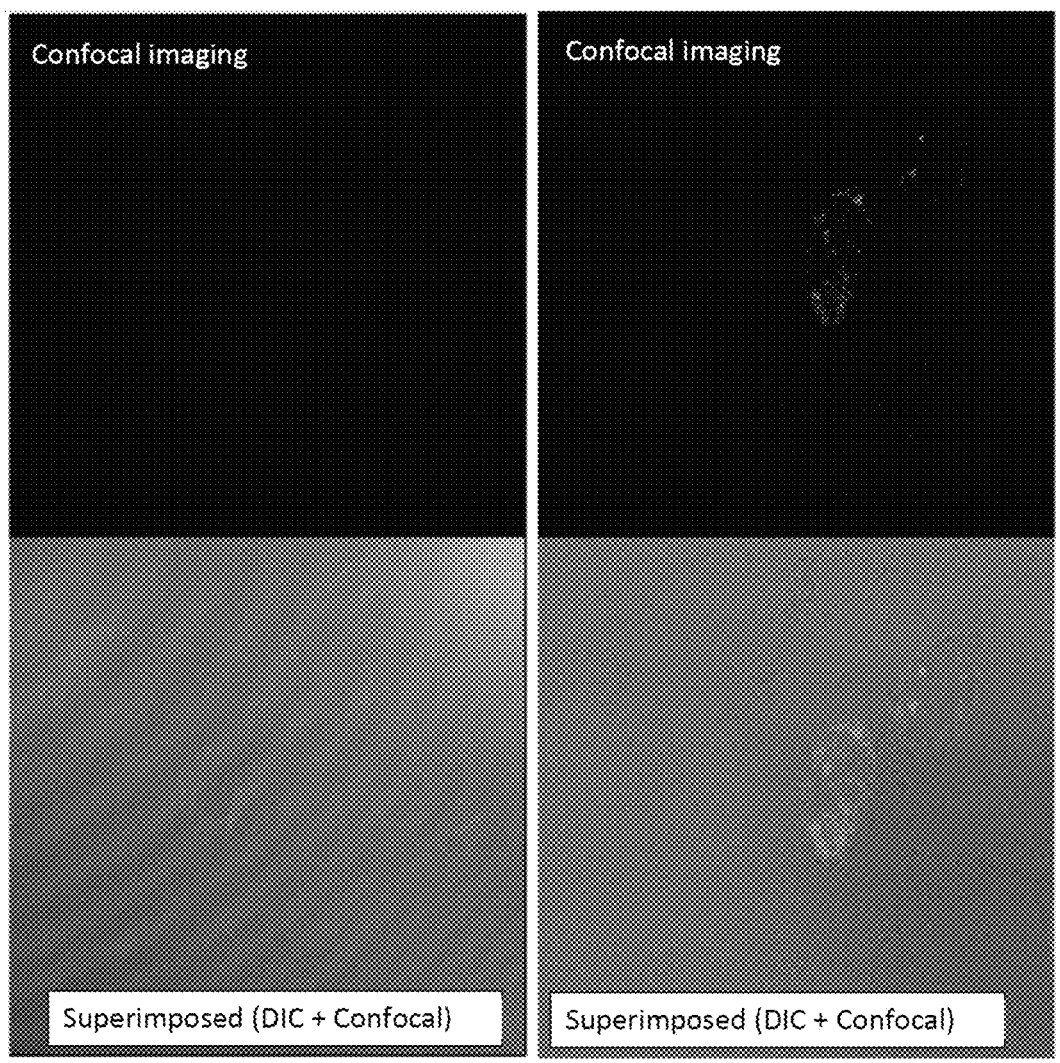
FIG. 18 shows an embodiment of confocal imaging showing uptake of PLGA-PEG nanoparticles encapsulating Quercetin in cancer cells overexpressing folate receptor (See, Example 6).

FIG. 18 shows confocal imaging data showing the uptake PLGA-PEG nanoparticles encapsulating Quercetin in cancer cells overexpressing the folic acid receptor. FIG. 18, top left shows confocal image of uptake of PLGA-PEG-QC-NPs labeled with Cy5 dye without folic acid conjugation, and FIG. 18, bottom left shows superimposed confocal and DIC images of uptake of PLGA-PEG-QC-NPs labeled with Cy5 dye without folic acid conjugation. FIG. 18, top right shows confocal image of uptake of PLGA-PEG-QC-NPs labeled with Cy5 dye with folic acid conjugation, and FIG. 18, bottom right shows superimpose confocal and DIC images of uptake of PLGA-PEG-QC-NPs labeled with Cy5 dye with folic acid conjugation.

Preferential uptake by cancer cells of PLGA-PEG-QC nanoparticles conjugated to folic acid was observed (FIG. 18; top right and bottom right) compared to non-conjugated nanoparticle (i.e., not conjugated to folic acid) (FIG. 18; top and bottom left).

Example 7—Confocal Imaging of the Nanoparticles in OVACAR3 Cells

PLGA-PEG-NPS, DSPE-PEG-NPS, FA-PEG-NPS and FA-DSPE-PEG-NPS particles labeled with a dye (Cy5) are synthesized. These nanoparticles are used to examine the preferential uptake of the nanoparticles with or without folic acid in an ovarian cancer cell line (OVACAR3) that overexpress the folic acid receptor.

Confocal image data are collected of the uptake of PLGA-PEG-QC-NPs labeled with Cy5 dye without folic acid conjugation. Superimposed confocal and DIC images of uptake of PLGA-PEG-QC-NPs labeled with Cy5 dye without folic acid conjugation are also collected. Confocal image data are collected of uptake of PLGA-PEG-QC-NPs labeled with Cy5 dye with folic acid conjugation. Superimposed confocal and DIC images of uptake of PLGA-PEG-QC-NPs labeled with Cy5 dye with folic acid conjugation are also collected.

Preferential uptake by cancer cells of PLGA-PEG-QC of nanoparticles conjugated to folic acid is observed compared to non-conjugated nanoparticle (i.e., not conjugated to folic acid).

Example 8—Accumulation of the Nano Formulations in the Animal with Implanted Tumor Data related to studies on accumulation of the nano formulations in the animal with implanted tumor are provided.

Animals—Immunodeficient, female athymic mice aged 5-6 weeks and weighing between 18 and 20 g were purchased from Taconic Biosciences (Albany, NY). All animal studies were conducted at the animal facility of the Veteran Affairs Medical Center, Albany, NY in accordance with and approved by institutional guidelines for humane animal treatment and according to the current guidelines. Mice were maintained under specific pathogen-free conditions and housed under controlled conditions of temperature (20-24° C.) and humidity (60-70%) and 12 h light/dark cycle with ad libitum access to water and food. Mice were allowed to acclimatize for 5 d prior to the start of study.

Treatment—OVCAR 3 Cancer cells ($1\times10^6$) were implanted subcutaneously in right flank of each animal. In the first set of experiments, control, free Quercetin (3 mg/kg), NPS-quercetin(3 mg/kg), and FA-NPs-quercetin (3 mg/kg) were injected subcutaneously to the mice everyday (for 14 days). The control was PBS, after humane sacrifice of animals at 14 days, tumors were harvested and amount of QC was measured.

Figure 12:
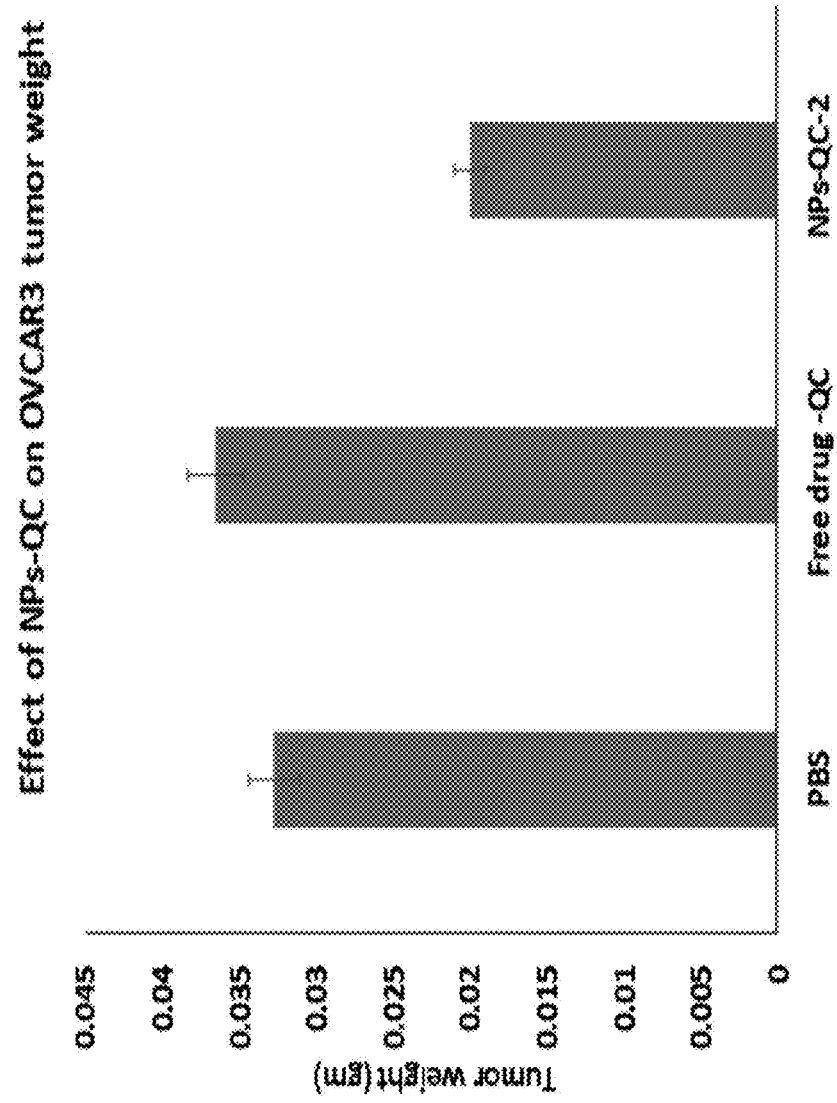
FIG. 12 shows effect of an embodiment of nanoformulated quercetin on tumor weight (See, Example 8).

FIG. 12 shows the effect of Quercetin and nano-formulated quercetin on tumor weight. Though Free QC and NPS-QC does not have any adverse toxic effect on the health of tumor bearing mice, however, in case FA-NPS-QC there was black patch observed in the injection site and tumor (after 24 hrs. of injection).

Figure 13:
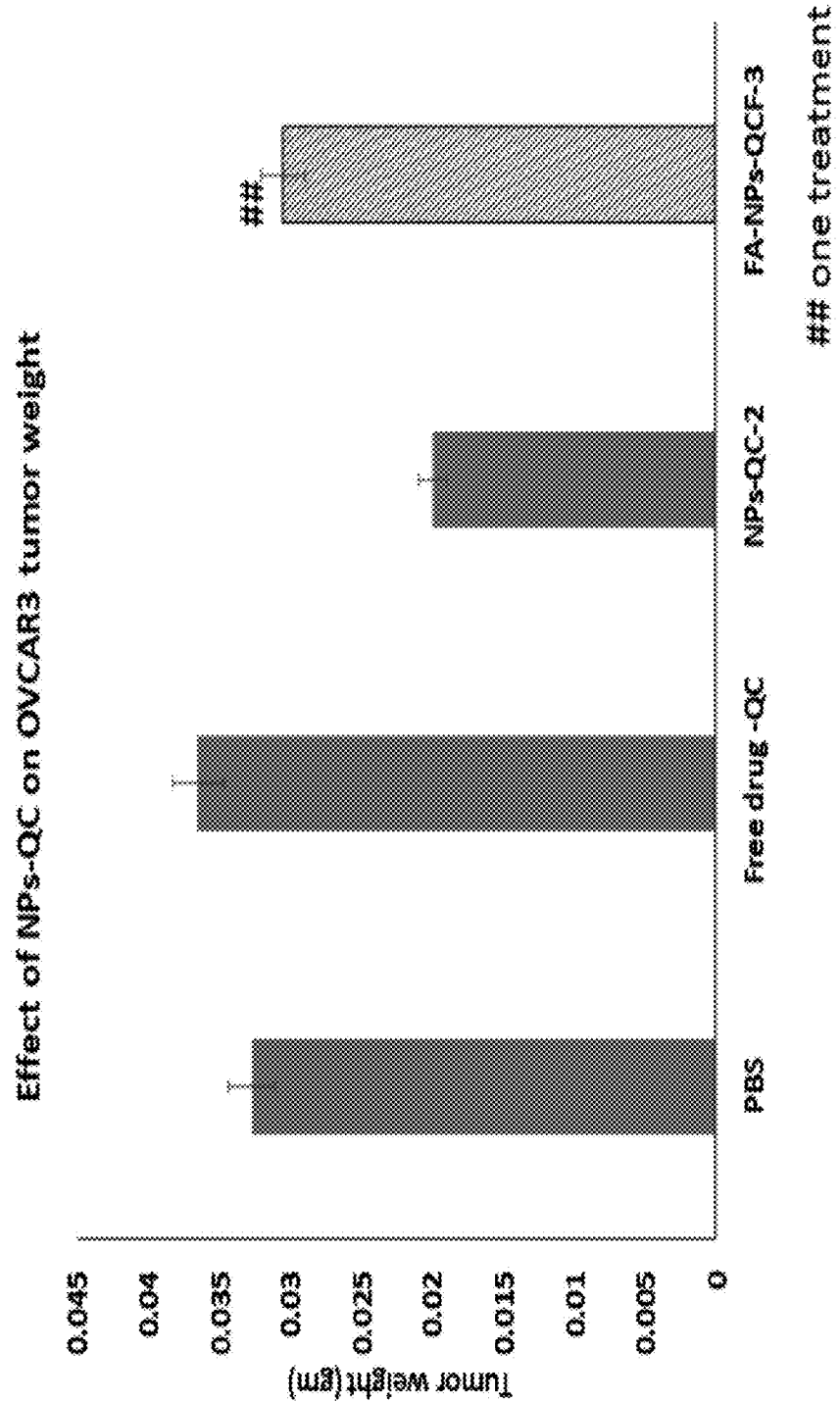
FIG. 13 shows effect of a single dose of an embodiment of nanoformulated quercetin on tumor weight (See, Example 8).

FIG. 13 shows effect of Quercetin and nano-formulated quercetin on tumor weight. Because administration of FA-NPS-QC resulted in a black patch at the injection site and tumor (after 24 hrs. of injection), the mice were administered a only one single dose of FA-QC-NPS.

Figure 14:
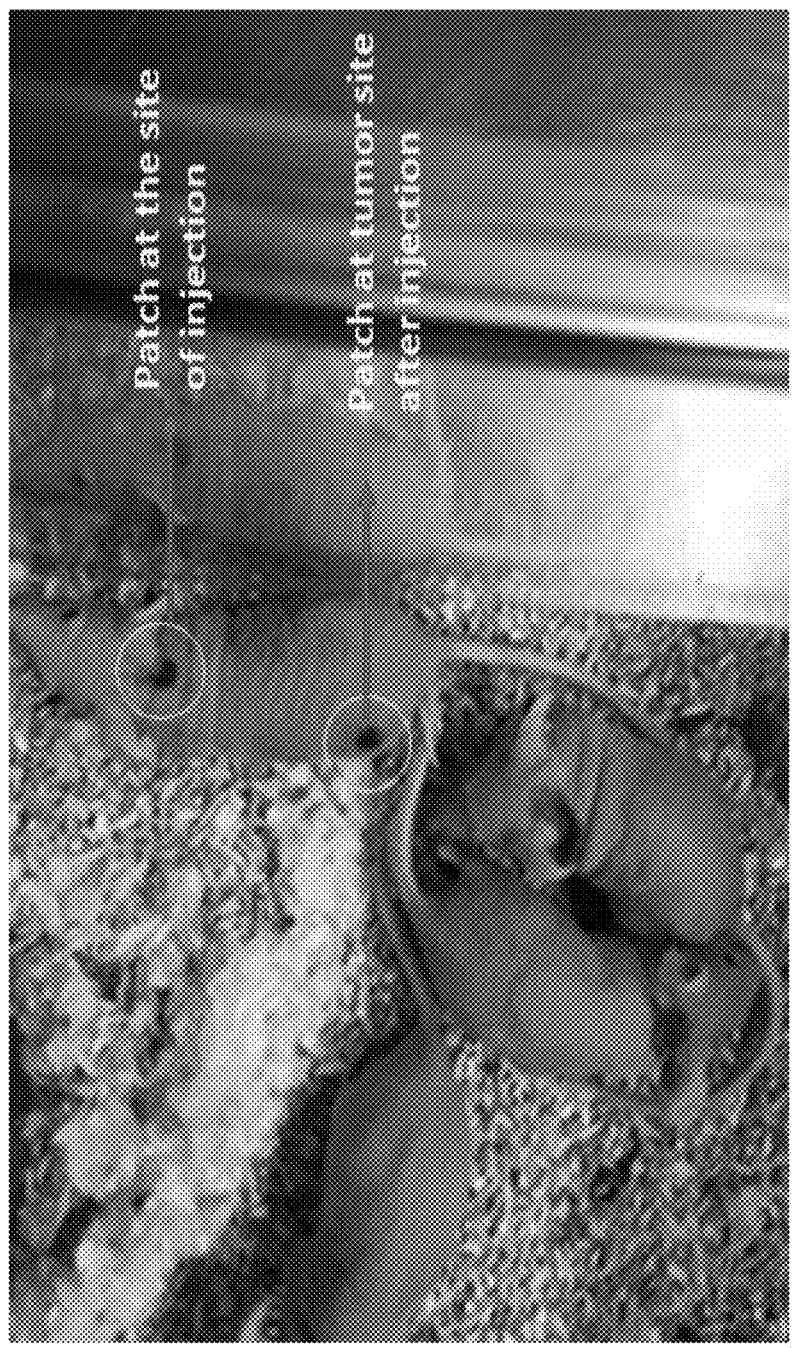
FIG. 14 shows side effects of an embodiment of the FA-NPS-QC on tumor bearing mice (See, Example 8).

FIG. 14 shows side effects of the FA-NPS-QC on tumor bearing mice.

Though this black patch was observed in 24 hours of injection, however, there was other adverse toxic effect (like weight loss, behavioral change) were not observed.

Figure 15:
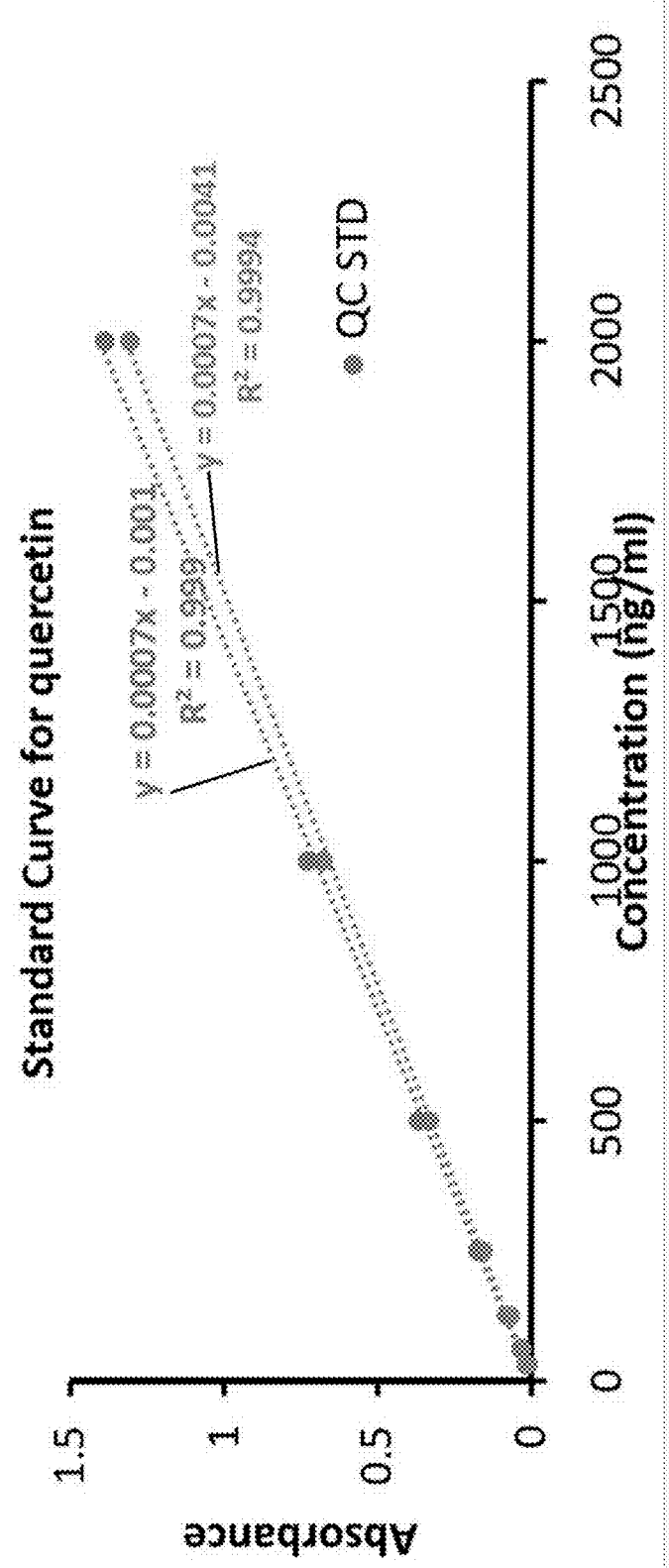
FIG. 15 shows an embodiment of a standard curve graph for measurement of quercetin (See, Example 8).
Figure 16:
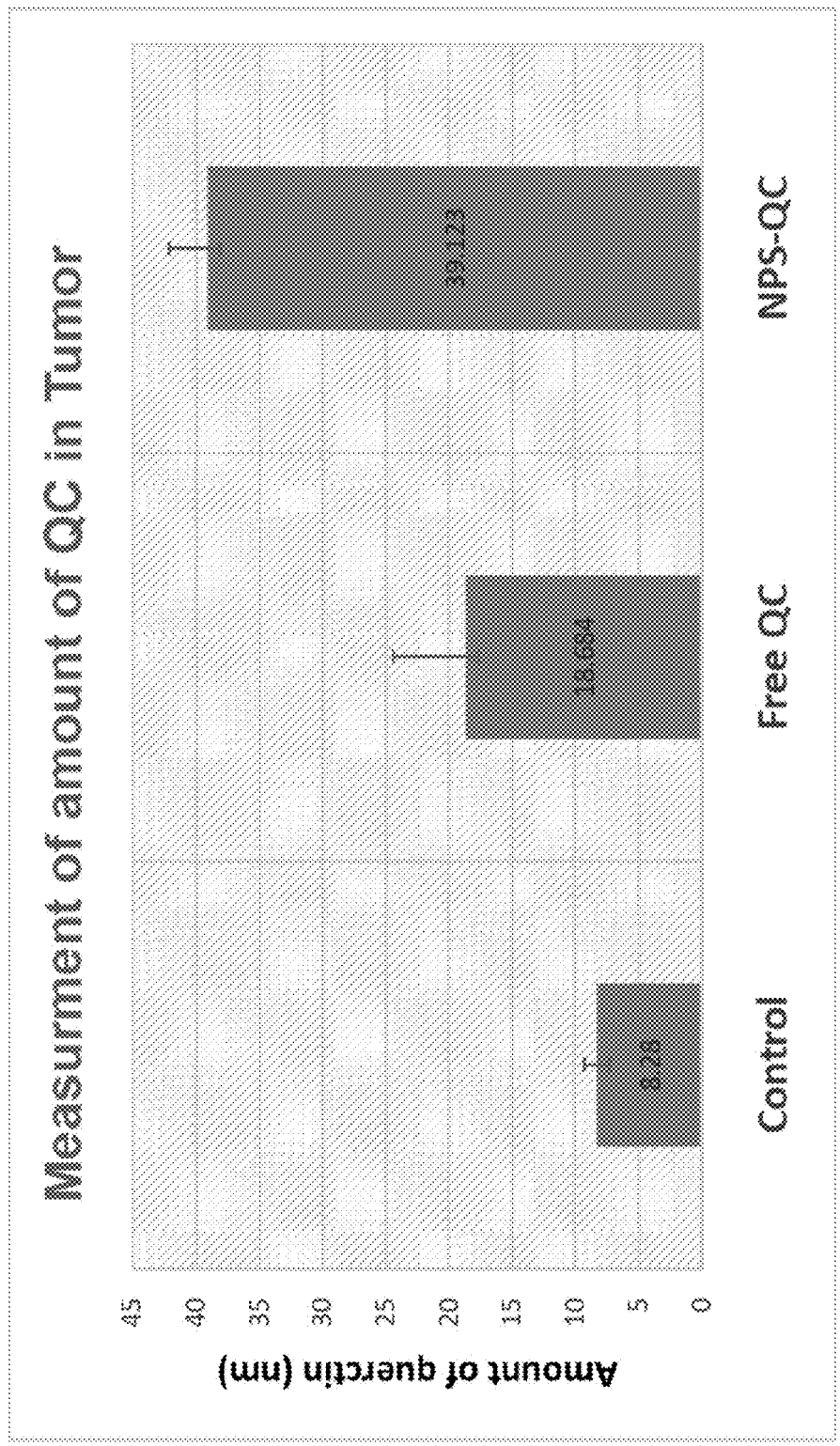
FIG. 16 shows an embodiment of a graph of amount of QC in tumor (See, Example 8).
Figure 17:
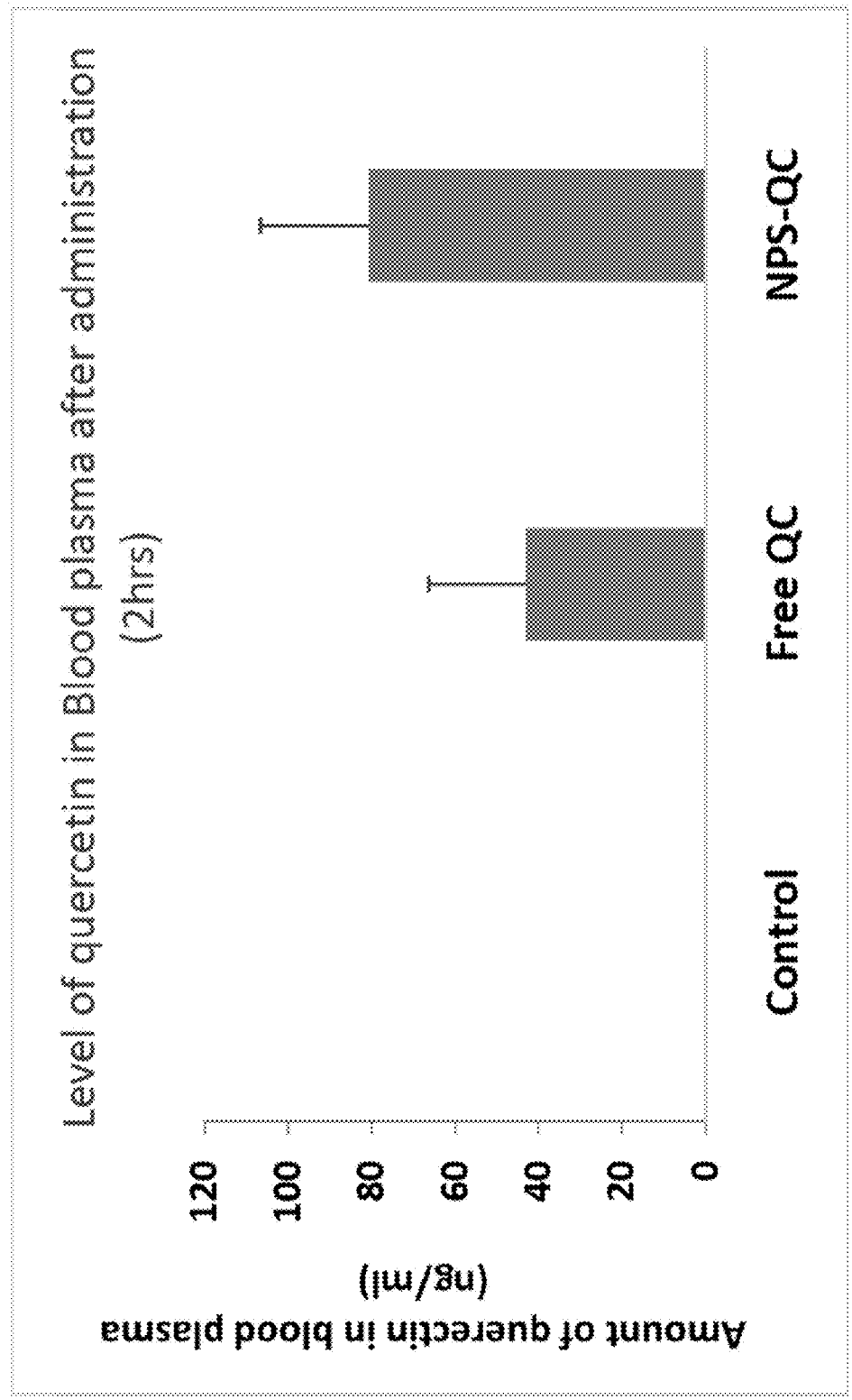
FIG. 17 shows an embodiment of a graph of amount of QC in blood plasma (See, Example 8).

FIG. 15 shows standard curve of Quercetin (with and without spiking in the blood). For the measurement of QC levels in blood/plasma, tumor and other major organs of the treated mice, a method of measurement of QC was developed. This method was validated by spiking known amount of QC in whole blood and extracting the QC using acetonitrile and methanol solution. The method of extraction from blood/plasma, tumor and other organs were developed and it was observed that % of extraction of QC was more than 90%. FIG. 16 shows measurement of amount of quercetin in the tumor after the termination of the study. FIG. 17 shows measurement of quercetin in blood plasma after 2 hrs. of injection (subcutaneous).

Example 9—Treatment of Rituximab (Rituxan)-, Ibrutinib (Imbruvica)-, Cetuximab (Erbitux)-, Crizotinib (Xalkori)-, Ceritinib (Zykadia)-, Trastuzumab (Herceptin)-, Everolimus (Afinitor)-, Afatinib (Gilotrif)-, Bevacizumab (Avastin)-, Trametinib (Mekinist)- or Temodar-resistant neoplasm with a combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and at least one modulator One or more patients are identified who have one or more cancers selected from astrocytomas, pilocytic astrocytoma, diffuse astrocytoma, anaplastic astrocytoma, and brain stem gliomas, glioblastomas, glioblastomas multiforme, meningioma, gliomas, ependymomas, oligodendrogliomas, and mixed gliomas, brain tumors, pituitary tumors, craniopharyngiomas, germ cell tumors, pineal region tumors, medulloblastomas, and primary CNS lymphomas.

The one or more patients are administered a formulation comprising, consisting of, or consisting essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) only. Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) is given at a dose of about 0.01 mg/day, mg/kg, or mg/m² to about 1000 mg/day, mg/kg, or mg/m².

On the day of the next administration and prior to the administration, as assessment of the outcome of treatment until that point is conducted and compared to all previous assessments.

Assessment of the patients after an initial period of treatment in terms of parameters such as cancer progression, growth and size, indicates that the cancers have not progressed, slowed in growth, stopped growing/progressing, reduced in size, and/or eliminated. However, following the initial response period, patients show a decline in response to Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist).

The cancers eventually become resistant to Afatinib. The cancers resume progressing and growing in size.

Patients are then administered a combination comprising, consisting of, or consisting essentially of, a Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and at least one modulator selected from quercetin, SPB and EGCG as disclosed herein. Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) is given at a dose of about 0.01 mg/day, mg/kg, or mg/m$^2$ to about 1000 mg/day, mg/kg, or mg/m$^2$. The at least one modulator is given at a dose as disclosed herein. An assessment of the outcome of treatment is periodically made.

After a minimum period of treatment (e.g., one day), the patient shows improvement. Assessments of the cancer in terms of parameters such as its progression, growth and/or size, indicates that the cancer has not progressed, slowed in growth, stopped growing/progressing, remained the same or reduced in size, and/or been eliminated. Additional assessment shows that after therapy, patients have improved in one or more measures selected from the group of: Natural Killer cell activity, increased WBC count, decreased LDH activity, decreased tumor markers, shrinkage of tumor in radiographic studies, decrease in CRP (correlation with improved survival), improved IgF-1. In some cases, the patients do not show a decline in response to the combination comprising, consisting of, or consisting essentially of, a Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) plus at least one modulator selected from quercetin, SPB and EGCG as disclosed herein during the course of the treatment, and the cancers are eventually eliminated without relapse.

Example 10—Treatment of neoplasm with Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and at least one modulator One or more patients are identified who have one or more cancers selected from astrocytomas, pilocytic astrocytoma, diffuse astrocytoma, anaplastic astrocytoma, and brain stem gliomas, glioblastomas, glioblastomas multiforme, meningioma, gliomas, ependymomas, oligodendrogliomas, and mixed gliomas, brain tumors, pituitary tumors, craniopharyngiomas, germ cell tumors, pineal region tumors, medulloblastomas, and primary CNS lymphomas.

Patients are then administered a combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and at least one modulator selected from quercetin, SPB and EGCG as disclosed herein Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) is given at a dose of about 0.01 mg/day, mg/kg, or mg/m$^2$ to about 1000 mg/day, mg/kg, or mg/m$^2$. The at least one modulator is given at a dose as disclosed herein. An assessment of the outcome of treatment is periodically made.

After a minimum period of treatment (e.g., one day) at a minimum dose required to prevent and/or treat the neoplasm, the patient shows improvement. Assessments of the cancer in terms of parameters such as its progression, growth and/or size, indicates that the cancer has not progressed, slowed in growth, stopped growing/progressing, remained the same or reduced in size, and/or been eliminated. Additional assessment shows that after therapy, patients have improved in one or more measures selected from the group of: Quality of Life, Tumor burden, clinical (progression-free and overall survival) and laboratory markers, including markers for tumor growth and metastasis, angiogenesis (Plasma VEGF, TGF, FGF2, and other growth factors), stem cell activity, and epidermo-mesenchymal transition (EMT), circulatory DNA, circulatory tumor cells (CTC), and serum Her2 levels. Natural Killer cell activity, increased WBC count, decreased LDH activity, decreased tumor markers, shrinkage of tumor in radiographic studies, decrease in CRP (correlation with improved survival), improved IgF-1. In some cases, the patients do not show a decline in response to the combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) plus at least one modulator selected from quercetin, SPB and EGCG as disclosed herein during the course of the treatment, and the cancers are eventually eliminated without relapse.

Example 11—Treatment of Rituximab (Rituxan)-, Ibrutinib (Imbruvica)-, Cetuximab (Erbitux)-, Crizotinib (Xalkori)-, Ceritinib (Zykadia)-, Trastuzumab (Herceptin)-, Everolimus (Afinitor)-, Afatinib (Gilotrif)-, Bevacizumab (Avastin)-, Trametinib (Mekinist)- or Temodar-resistant neoplasm with a combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and at least one modulator in a nanoparticle One or more patients are identified who have one or more types of brain cancers selected from astrocytomas, pilocytic astrocytoma, diffuse astrocytoma, anaplastic astrocytoma, and brain stem gliomas, glioblastomas, glioblastomas multiforme, meningioma, gliomas, ependymomas, oligodendrogliomas, and mixed gliomas, brain tumors, pituitary tumors, craniopharyngiomas, germ cell tumors, pineal region tumors, medulloblastomas, and primary CNS lymphomas.

The one or more patients are administered a formulation comprising, consisting of, or consisting essentially of, Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) is given at a dose of about 0.01 mg/day, mg/kg, or mg/m² to about 1000 mg/day, mg/kg, or mg/m².

On the day of the next administration and prior to the administration, as assessment of the outcome of treatment until that point is conducted and compared to all previous assessments.

Assessment of the patients after an initial period of treatment in terms of parameters such as cancer progression, growth and size, indicates that the cancers have not progressed, slowed in growth, stopped growing/progressing, reduced in size, and/or eliminated. However, following the initial response period, patients show a decline in response to Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist).

The cancers resume progressing and growing in size.

Patients are then administered a nanoparticle formulation comprising, consisting of, or consisting essentially of, a combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and nano-quercetin. Nano-Rituximab (Rituxan), -Ibrutinib (Imbruvica), -Cetuximab (Erbitux),-Crizotinib (Xalkori), -Ceritinib (Zykadia), -Trastuzumab (Herceptin), -Everolimus (Afinitor), -Afatinib (Gilotrif), -Bevacizumab (Avastin) or -Trametinib (Mekinist) is given at a dose of about 0.01 mg/day, mg/kg, or mg/m² to about 1000 mg/day, mg/kg, or mg/m². Nano-Quercetin is given at a dose of Quercetin as disclosed herein. An assessment of the outcome of treatment is periodically made.

After a minimum period of treatment (e.g., one day), the patient shows improvement. Assessments of the cancer in terms of parameters such as its progression, growth and/or size, indicates that the cancer has not progressed, slowed in growth, stopped growing/progressing, remained the same or reduced in size, and/or been eliminated. Additional assessment shows that after therapy, patients have improved in one or more measures selected from the group of: Natural Killer cell activity, increased WBC count, decreased LDH activity, decreased tumor markers, shrinkage of tumor in radiographic studies, decrease in CRP (correlation with improved survival), improved IgF-1. In some cases, the patients do not show a decline in response to the combination comprising, consisting of, or consisting essentially of, a Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) plus quercetin during the course of the treatment, and the cancers are eventually eliminated without relapse.

Example 12—Treatment of neoplasm with a nano-formulation of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and at least one modulator One or more patients are identified who have one or more types of brain cancer selected from astrocytomas, pilocytic astrocytoma, diffuse astrocytoma, anaplastic astrocytoma, and brain stem gliomas, glioblastomas, glioblastomas multiforme, meningioma, gliomas, ependymomas, oligodendrogliomas, and mixed gliomas, brain tumors, pituitary tumors, craniopharyngiomas, germ cell tumors, pineal region tumors, medulloblastomas, and primary CNS lymphomas.

Patients are then administered a nanoparticle formulation comprising, consisting of, or consisting essentially of, a combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and quercetin, in which at least one or both are present as nanoparticles. Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) is given at a dose of about 0.01 mg/day, mg/kg, or mg/m² to about 1000 mg/day, mg/kg, or mg/m². Quercetin is given at a dose as disclosed herein. An assessment of the outcome of treatment is periodically made.

After a minimum period of treatment (e.g., one day), the patient shows improvement. Assessments of the cancer in terms of parameters such as its progression, growth and/or size, indicates that the cancer has not progressed, slowed in growth, stopped growing/progressing, remained the same or reduced in size, and/or been eliminated. Additional assessment shows that after therapy, patients have improved in one or more measures selected from the group of: Natural Killer cell activity, increased WBC count, decreased LDH activity, decreased tumor markers, shrinkage of tumor in radiographic studies, decrease in CRP (correlation with improved survival), improved IgF-1. In some cases, the patients do not show a decline in response to the combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) plus quercetin during the course of the treatment, and the cancers are eventually eliminated without relapse.

Example 13—Treatment of neoplasm with a nano-formulation of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and at least one modulator One or more patients are identified who have one or more types of brain cancer selected from astrocytomas, pilocytic astrocytoma, diffuse astrocytoma, anaplastic astrocytoma, and brain stem gliomas, glioblastomas, glioblastomas multiforme, meningioma, gliomas, ependymomas, oligodendrogliomas, and mixed gliomas, brain tumors, pituitary tumors, craniopharyngiomas, germ cell tumors, pineal region tumors, medulloblastomas, and primary CNS lymphomas.

Patients are then administered a nanoparticle formulation comprising, consisting of, or consisting essentially of, a combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) and quercetin, in which both are present as nanoparticles. Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) is given at a dose of about 0.01 mg/day, mg/kg, or mg/m$^2$ to about 1000 mg/day, mg/kg, or mg/m$^2$. Quercetin is given at a dose of as disclosed herein. An assessment of the outcome of treatment is periodically made.

After a minimum period of treatment (e.g., one day) at a minimum dose required to prevent and/or treat the neoplasm, the patient shows improvement. Assessments of the cancer in terms of parameters such as its progression, growth and/or size, indicates that the cancer has not progressed, slowed in growth, stopped growing/progressing, remained the same or reduced in size, and/or been eliminated. Additional assessment shows that after therapy, patients have improved in one or more measures selected from the group of: Natural Killer cell activity, increased WBC count, decreased LDH activity, decreased tumor markers, shrinkage of tumor in radiographic studies, decrease in CRP (correlation with improved survival), improved IgF-1. In some cases, the patients do not show a decline in response to the combination of Rituximab (Rituxan), Ibrutinib (Imbruvica), Cetuximab (Erbitux), Crizotinib (Xalkori), Ceritinib (Zykadia), Trastuzumab (Herceptin), Everolimus (Afinitor), Afatinib (Gilotrif), Bevacizumab (Avastin) or Trametinib (Mekinist) plus quercetin during the course of the treatment, and the cancers are eventually eliminated without relapse.

Example 14—Case Study—Yvonne—Treatment of breast cancer with Quercetin PG+SPB, and Quercetin PG+SPB+Afatinib This is a case study of a 57 year old female patient with invasive ductal breast carcinoma. She was treated in Mexico and remained in remission for eight years, when she had a recurrence presenting with right breast pain. She went back to Mexico and had a right mastectomy. Her pathology showed ER/PR/HER2 triple positive with a Ki67 of 60%. She received Herceptin and hormonal blockade with arimidex treatments. Her PET scan done at that time confirmed metastatic disease with bone involvement. She then was treated with hormonal blockade, Herceptin, as well as Zometa.

She progressed despite such therapies received under the care of her oncologist. She also was unsuccessfully treated with chemotherapy, Xeloda. She also failed Tamoxifen and radiation.

Prior to obtaining treatment at the clinic of Dr. Nezami with the methods and compositions disclosed herein, she had been treated with Femara, but her most recent PET scan about 16.5 years after her initial diagnosis again showed progression of disease with complete destruction of the sternum. There were multiple lung metastases as well as extensive disease in the peritoneum. At this time, she arrived at the clinic of Dr. Nezami seeking epigenetic treatments sought treatment using the disclosed methods and compositions. By this time she had already failed Her2 blockers and all conventional therapies.

Upon her arrival to Dr. Nezami's clinic, she was evaluated and laboratory tests were performed. At the start of her treatment, molecular detection of circulating tumor cells was performed as follows. In order to obtain circulating tumor cells from the patient's peripheral blood, large cells and cell-clusters as well as epithelial cells were isolated. A preparation of mononuclear cells (MNC) served as a control cell fraction. mRNA was isolated from all fractions. Thereafter, the expression of tumor relevant genes was measured by quantitative real-time RT-PCR. A preparation of mononuclear cells (MNC) served as a control cell fraction.

The expression of the telomerase gene can be increased in most tumor types but not in normal tissue. An increased expression of telomerase gene may be indicative of the presence of tumor cells in the circulation. Expression of telomerase was not detected in the isolated cells. Overexpression of C-MYC indicates an increased proliferation of the isolated cells. An increased proliferation rate is a typical feature of tumor cells. The expression level of C-MYC was elevated. Overexpression of ERBB2 (HER2/NEU) is a trait of different types of cancer and may also be observed in breast cancer. Thus, the detection of ERBB2 overexpression may be indicative of the presence of circulating tumor cells. The expression of ERBB2 was elevated. The detection of expression of cytokeratin (CK) 19 indicates the presence of epithelial cells and may thus be indicative for circulating tumor cells. There was no expression of CK19 detected. Thus, in the isolated tumor cell fraction, expression of ERBB2 and C-MYC was above threshold (>2.0). This finding was indicated of the likely presence of circulating tumor cells in the analyzed blood sample. Thus, her laboratory results showed presence of circulating tumor cells (CTC) in the blood along with expression of ERBB2 and C-MYC. These CTC were ER negative.

Figure 19:
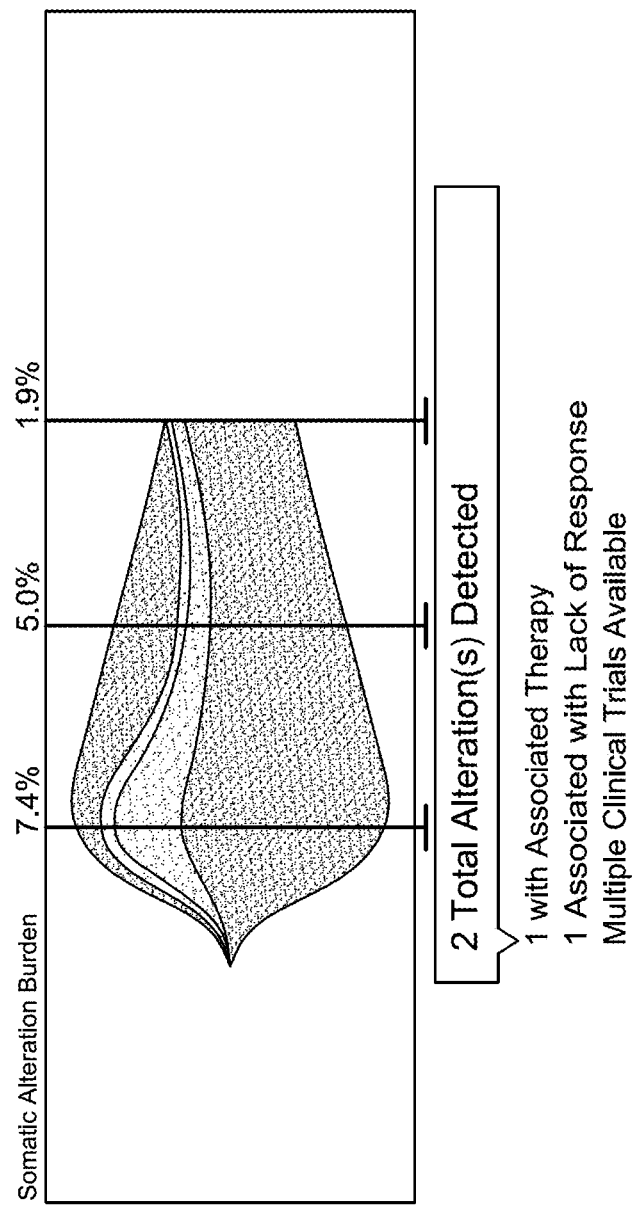
FIG. 19 shows an embodiment of a Guardant360 Tumor Response Map (See, Example 14).

A Guardant360 Tumor Response Map (e.g., FIG. 19) illustrates the relative changes observed in cell-free DNA (cfDNA) at different sample submission time points. The genes covered by the Guardant360 Tumor Response Map are listed in TABLE 7.

TABLE 7

Genes detected by Guardant360 Tumor Response Map
Complete Sequencing of Covered Exons*

| Point Mutations (SNVs) (73 Genes) | | | | | | | Indels (23 Genes) | | Amplifications (CNVs) (18 Genes) | | Fusions (6 Genes) |
|---|---|---|---|---|---|---|---|---|---|---|---|
| AKT1 | ALK | APC | AR | ARAF | ARID1A | ATM | ATM | APC | AR | BRAF | ALK |
| BRAF | BRCA1 | BRCA2 | COND1 | COND2 | CCNE1 | CDH1 | ARID1A | BRCA1 | COND1 | COND2 | FGFR2 |
| CDK4 | CDK6 | CDKN2A | CTNNB1 | DDR2 | EGFR | ERBB2 | BRCA2 | CDH1 | CCNE1 | CDK4 | FGFR3 |
| ESR1 | EZH2 | FBXW7 | FGFR1 | FGFR2 | FGFR3 | GATA3 | CDKN2A | EGFR | CDK6 | EGFR | NTRK1 |
| GNA11 | GNAQ | GNAS | HNF1A | HRAS | IDH1 | IDH2 | ERBB2 | GATA3 | ERSBB2 | FGFR1 | RET |
| JAK2 | JAK3 | KIT | KRAS | MAP2K1 | MAP2K2 | MAPK1 | KIT | MET | FGFR2 | KIT | ROS1 |
| MAPK3 | MET | MLH1 | MPL | MTOR | MYC | NF1 | MLH1 | MTOR | KRAS | MET | |
| NFE2L2 | NOTCH1 | NPM1 | NRAS | NTRK1 | NTRK3 | PDGFRA | NF1 | PDGFRA | MYC | PDGFRA | |
| PIK3CA | PTEN | PTPNI1 | RAF1 | RB1 | RET | RHEB | PTEN | RB1 | PIK3CA | RAF1 | |
| RHOA | RIT1 | ROS1 | SMAD4 | SMO | STK11 | TERT** | SMAD4 | STK11 | | | |

TABLE 7-continued

Genes detected by Guardant360 Tumor Response Map
Complete Sequencing of Covered Exons*

| Point Mutations (SNVs) (73 Genes) | | | Indels (23 Genes) | Amplifications (CNVs) (18 Genes) | Fusions (6 Genes) |
|---|---|---|---|---|---|
| TP53 | TSC1 | VHL | TP53 VHL | TSC1 | |

*Exons selected to maximize detection of known somatic mutations. List available upon request
**includes TERT promoter region The "Somatic Alteration Burden" value (e.g., in FIG. 20) refers to the maximum % cfDNA detected at each time point. Amplifications are not plotted, and only the first and last four test dates are plotted. The percentage, or allele frequency, of altered % cfDNA circulating in blood is related to the unique tumor biology of each patient. Factors that may affect the % cfDNA of detected somatic alterations include tumor growth, turn-over, size, heterogeneity, vascularization, disease progression, and treatment.

Figure 20:
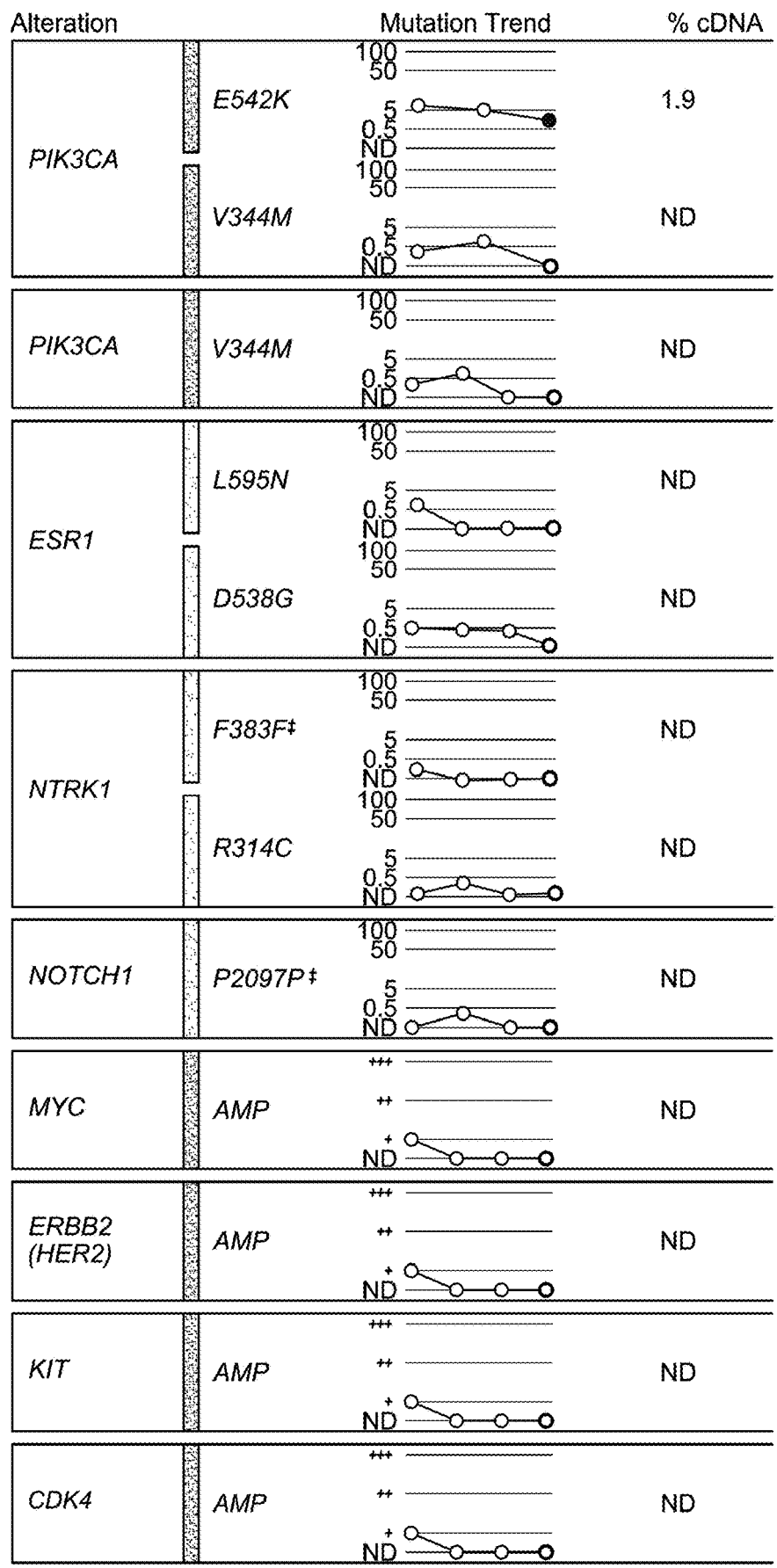
FIG. 20 shows an embodiment of a summary of somatic alterations and associated treatment options (See, Example 14).

Results of % cfDNA detected are categorized as follows: ND represents genomic alterations not detected. Genomic alterations may be present that are below the limit of detection of this test. Certain sample or variant characteristics may result in reduced analytic sensitivity, such as poor sample quality or improper collection. Genomic alterations in a tumor may be present but are not detected in circulating cell-free DNA from this blood specimen with this test. Similar to other alterations in circulating cfDNA, the amount (% cfDNA) of this variant may reflect disease progression or response to treatment. Therefore, clinical correlation is advised. As the absolute number of copies in circulation is dependent on both tumor fraction and the magnitude of the tumor amplification, amplifications are reported on a semi-quantitative scale. Positive (+) refers to amplification magnitude is in the lower $50^{th}$ percentile of samples with amplifications; Strongly Positive (++) refers to amplification magnitude is in the $50^{th}$ to $90^{th}$ percentile; Very Strongly Positive (+++) refers to amplification magnitude is in the top $10^{th}$ percentile. Positive (+) refers to amplification magnitude is in the lower $50^{th}$ percentile of samples with amplifications; Strongly Positive (++) refers to amplification magnitude is in the $50^{th}$ to $90^{th}$ percentile; Very Strongly Positive (+++) refers to amplification magnitude is in the top $10^{th}$ percentile. ND in FIG. 20 represents genomic alterations not detected.

Her tumor was sent for genomic studies. Molecular profiling was performed which showed presence of several mutations in her tissue biopsied from her humerus. While the tumor was negative for Her2, the tumor was ER positive and MSH-6 positive.

Figure 21:
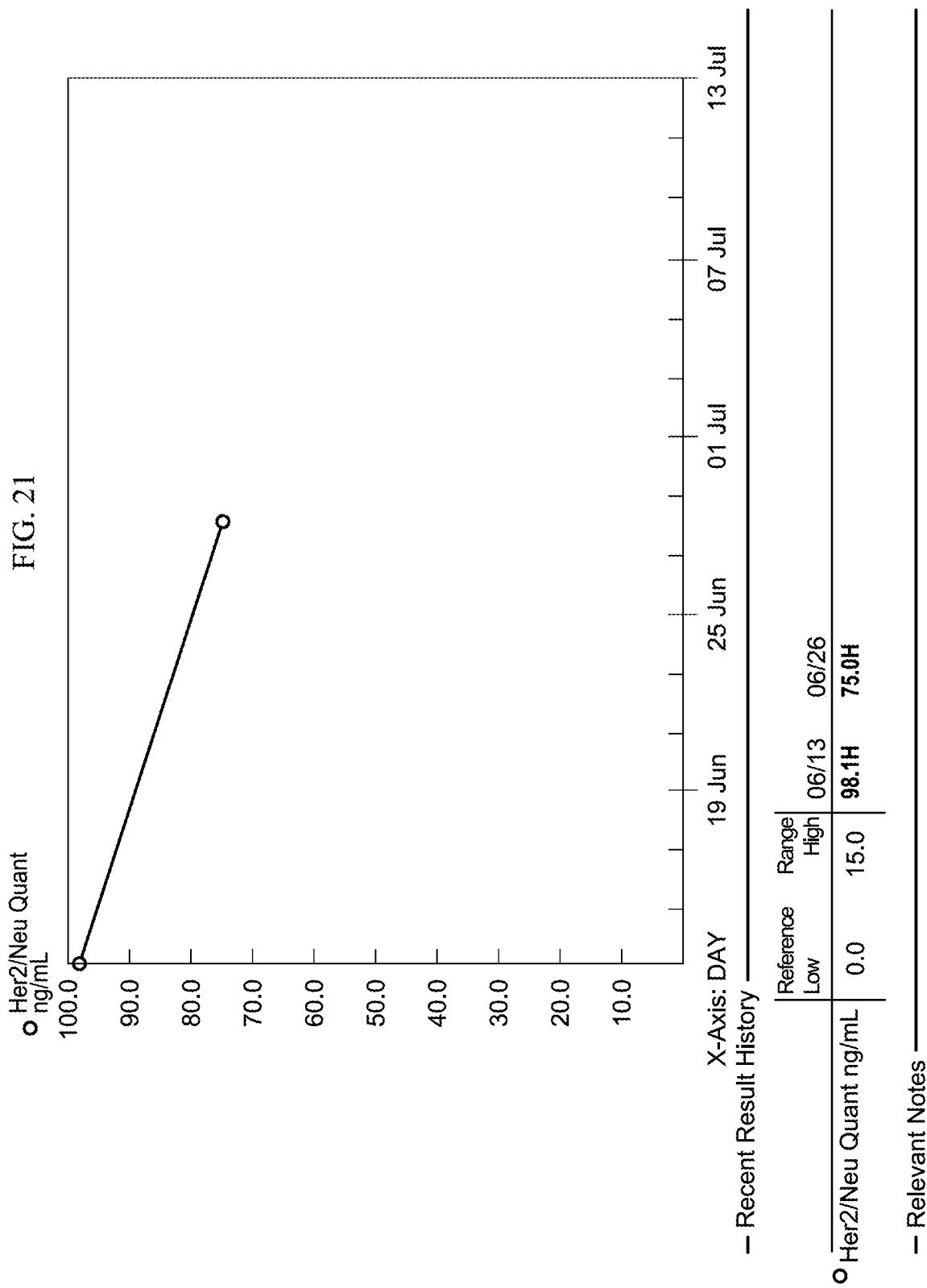
FIG. 21 shows an embodiment of a graph of serum Her2 levels before and after treatment (See, Example 14).

IV epigenetic therapies consisting of Quercetin PG and sodium phenyl butyrate (at doses of 0.5 grams and 5 grams, respectively) and were started immediately and continued on daily basis. After two weeks of therapy, laboratory tests confirmed response to the treatments. Her laboratory reports showed decreased tumor markers—CA 27.29 had decreased from 765 to 685, CA 15-3 had decreased from 574 to 533, and Her2 had decreased from 98 to 75 (FIG. 21), as measured after two weeks of therapy. Her % cfDNA showed a marked reduction from 7.4 to 5.0 at the level of PI3k. A repeat assay repeated about 5 weeks later showed further reduction from 5.0 to 1.9.

She was further treated with combination of epigenetic therapies with afatinib, administered orally at 40 mg per day. Her % cfDNA showed disappearance of PI3k, ESR1, NTRK1, NOTCH1, MYC, ERBB2, KIT, CDK4 (FIG. 20). As she continued her treatments at the clinic of Dr. Nezami, her markers continued to decrease. Additionally, she gained weight and energy, and her appetite improved. Her Her2 levels continued to decrease.

In summary, the unexpected clinical outcome in response to the disclosed epigenetic therapy, alone and in combination with Afatinib, observed in a patient with refractory stage IV cancer is superior to all currently available care and, to our knowledge, has never been previously reported in the literature.

In conclusion, patient's initial response to the epigenetic therapy alone was unexpected and further addition of anti-cancer agent showed additional improvement that was unexpected because the patient was unresponsive to this category of anti-cancer agent alone. The patient had failed anti Her 2 therapy prior to the administration of epigenetic therapies. Also during the course of treatment, the application of anti Her2 therapy (Afatinib) alone was not effective. Based on current literature there is no expected clinical benefit from this particular drug in this type of cancer.

Example 15—Case Study—Anthony—Treatment of Squamous Cell Carcinoma with Quercetin PG+SPB, and Quercetin PG+SPB+Afatinib This case study is of a 43 years old male with history of stage four nasopharyngeal squamous cell carcinoma, diagnosed status post carboplatinum and taxol administration, and further switched to Gemzar, which he received for 9 rounds without response.

His PET scan prior to arriving at the clinic of Dr. Nezami showed significant progression of disease as documented by new lesions in liver and extensive bone metastases. Further, he was started on Keytruda 3 weeks prior to arriving at the clinic of Dr. Nezami. Due to significant toxicity, he could not tolerate further therapies with Keytruda. Additionally, he experienced significant abdominal pain and night sweats for which he was taking narcotics.

Upon his arrival at the clinic of Dr. Nezami he was immediately evaluated and his laboratory tests showed significantly high CTC with C-KIT and EGFR positive alterations, as well as high LDH and anemia with hemoglobin of 8.6.

He was started on IV epigenetic therapies consisting of intravenous Quercetin PG and sodium phenyl butyrate (at doses of 0.5 grams and 5 grams, respectively) which he received on daily basis for two weeks. His laboratory tests were then repeated, which showed reduction of FGF-2 from 37 to 2.5. His hemoglobin level increased to 10, and his pain had completely resolved.

His restaging PET scan about 12 months after his initial diagnosis showed a positive metabolic response with resolution of all metastatic lesions in his skeletal bones—L2 lesion SUV activity decreased from 8.5 to 1.7, sternum lesion activity decreased from 7.2 to background, left humerus activity decreased from 8.7 to 1.9, and T7 activity from 5.5 to 2.5.

As he continued to receive treatment at the clinic of Dr. Nezami, has was additionally administered Afatinib at 40 mg per day, in combination with the epigenetic therapies. This was based on his positive EGFR CTC.

His restaging scan performed about 2 months later showed decreased metabolic activity in all his neck lymph nodes as well as his liver lesions. His liver lesions SUV activity decreased from 12.6 to 8.2. His right supraclavicular lesion showed decreased metabolic activity from 12.1 to 8.9 and left supraclavicular lesion showed decreased metabolic activity from 9.4 to 5.4. His several sclerotic osseous lesions in thoracic and lumbar spine as well as sternum showed no FDG activity.

In summary, the observed response to the disclosed epigenetic therapies, alone and in combination with Afatinib, is highly impressive in a patient with widespread head and neck cancer who had failed cytotoxic therapies and immune therapy. In conclusion, patient's initial response to the epigenetic therapy alone was unexpected and further addition of anti-cancer agent showed additional improvement that was unexpected based on current literature there is no expected clinical benefit from this particular drug in this type of cancer.

Example 16—Case Study—Rebecca—Treatment of breast cancer with Quercetin PG+SPB, and Quercetin PG+Afatinib This is a case study of a 41 year old woman who presented at the clinic of Dr. Nezami with metastatic and advanced ER-/PR-/Her2 positive left breast ductal adenocarcinoma. She was also found to have germline BRCA mutation. She was at first diagnosed in Nigeria. At that time she underwent standard neoadjuvant chemotherapy (ACT regimen). Further she moved to India about a year prior to her arrival at the clinic of Dr. Nezami and had mastectomy and radiation to the left breast and chest wall along with 17 cycles of herceptin.

She and her husband then moved to the United States, where she was periodically monitored by her oncologist. About 4 years after her initial diagnosis, PET scan revealed recurrence of her disease, with ER-/PR-/Her2 positive disease per pathology report from lung mass, at which time point in time she went to Mexico for treatment. Since about 5 months thereafter she has also been under the care of her oncologist in California.

Her most recent CT scan prior to arriving at the clinic of Dr. Nezami showed progression of disease with worsening metastasis in the bones (T7, T8, lumbar, and sacral areas), multiple pulmonary nodules, and lymphadenopathy in the chest, bilateral pleural effusions, hepatomegaly and liver metastasis. CT scan of her brain was negative for metastases. She had been refusing further therapies as she qualified for hospice. Her records from her oncologist in Bakersfield showed declining function, (ECOG of 1-2) and worsening laboratory test results (LDH >1000, elevated LFTs, elevated tumor markers). Her oncologist had suggested hospice, which she had refused.

Upon her arrival at the clinic of Dr. Nezami, she was evaluated both through liquid biopsy and tissue biopsy molecular profiling. Overexpression of telomerase was detected in the isolated cells, the expression level of C-MYC was not elevated, the expression of ERBB2 was elevated, and there was expression of CK19 detected. Thus, in the isolated tumor cell fraction, expression of ERBB2 and telomerase was above threshold (>2.0) and the expression of CK19 was above threshold (≥1) in the higher range (>1000). This finding was indicated of the likely presence of circulating tumor cells in the analyzed blood sample. Her % cfDNA was positive for ERBB2, c MYC and TP53. However, her CTC was positive for ERBB2 and CK19.

Figure 22:
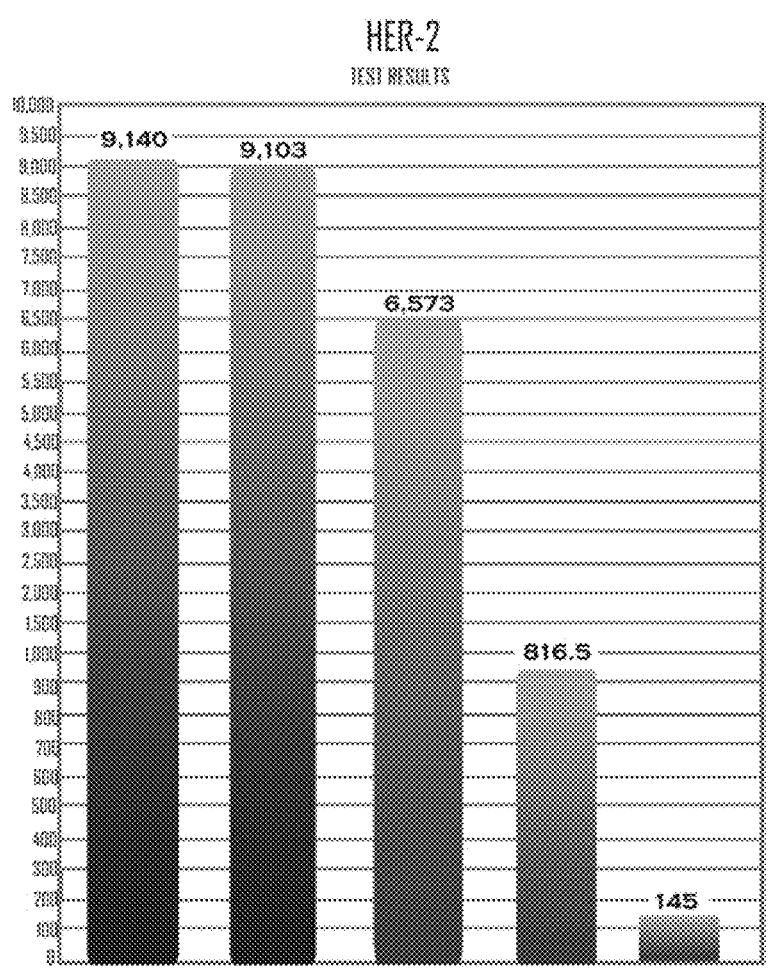
FIG. 22 shows an embodiment of a graph of serum Her2 levels before and after treatment (See, Example 16).
Figure 23:
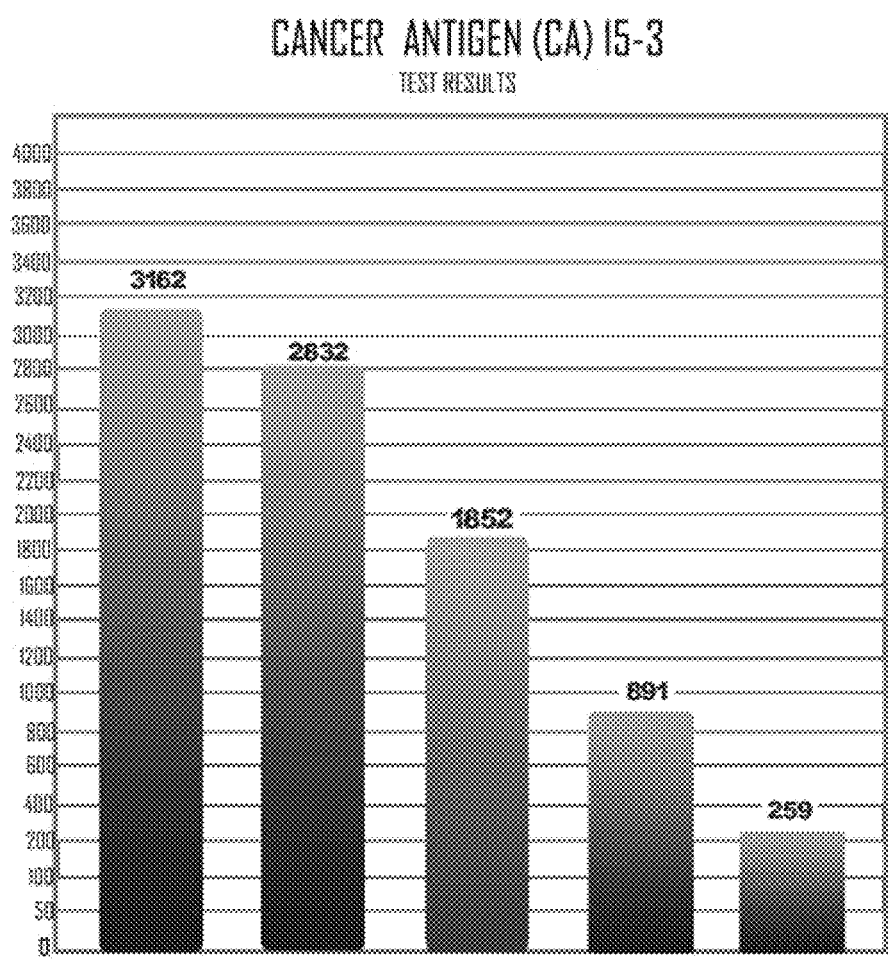
FIG. 23 shows an embodiment of a graph of CA 15-3 antigen levels before and after treatment (See, Example 16).
Figure 24:
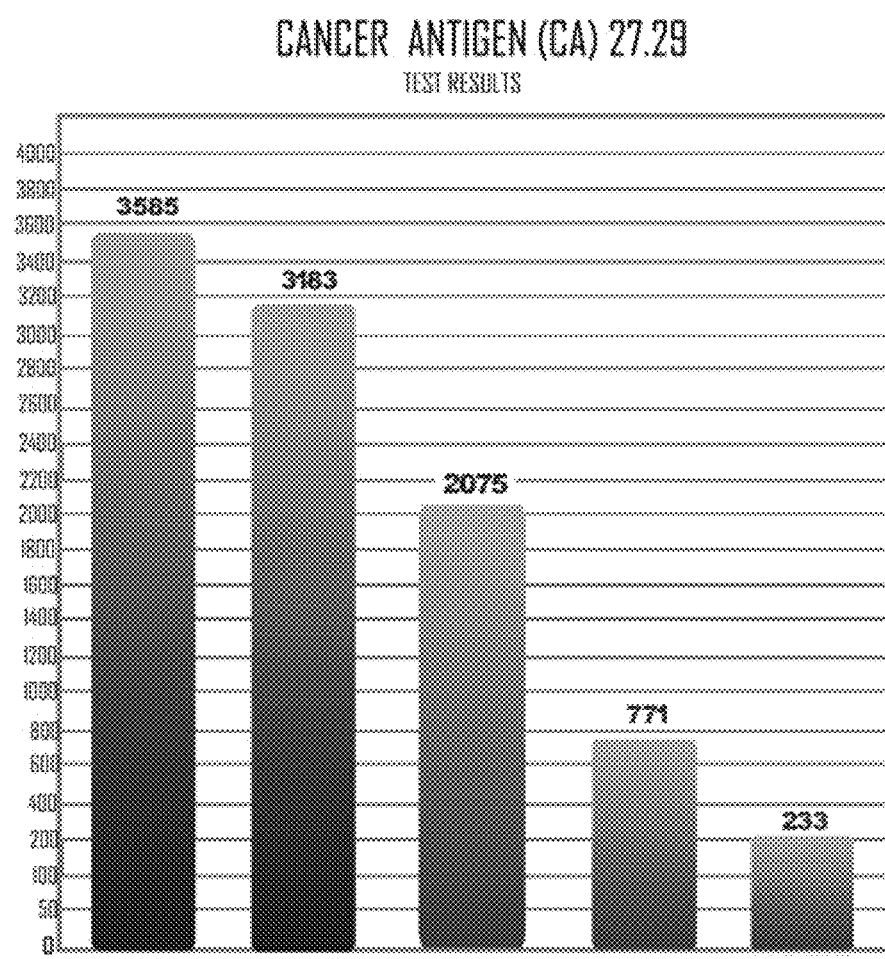
FIG. 24 shows an embodiment of a graph of CA 27.29 antigen levels before and after treatment (See, Example 16).

Additionally, she highly elevated serum Her 2 level at 9140 (FIG. 22), and she also had very high tumor markers—CA 15-3 at 3162 (FIG. 23), and CA 27.29 at 3585 (FIG. 24).

She was immediately started on IV epigenetic therapies, consisting of intravenous Quercetin PG and sodium phenyl butyrate (at doses of 0.5 grams and 5 grams, respectively), on daily basis 5 times a week. Her quality of life quickly improved since starting the treatments. Her ECOG improved substantially with improved breathing and reduced pain level. She was able to walk independently, and her jaundice resolved.

Figure 25:
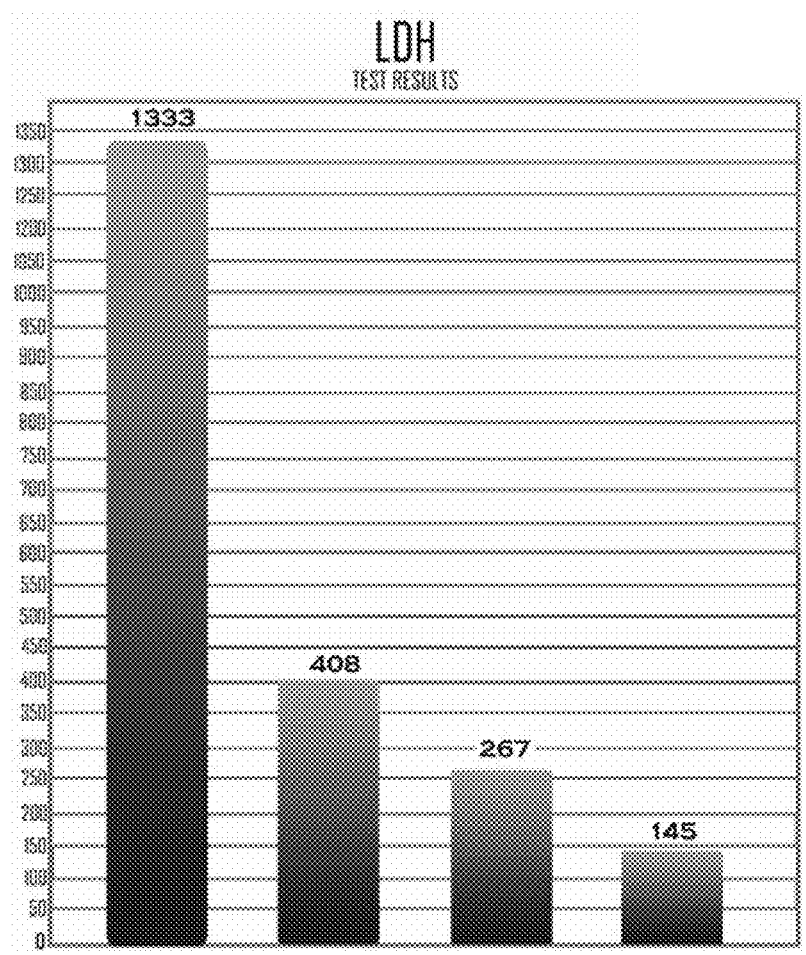
FIG. 25 shows an embodiment of a graph of LDH levels before and after treatment (See, Example 16).

Her laboratory tests were repeated after therapy for two weeks, which showed improved tumor markers and serum markers—serum Her2 decreased from 9140 to 6573 (FIG. 22), CA 15-3 decreased from 3162 to 2832 (FIG. 23), CA 27.29 decreased from 3585 to 3183 (FIG. 24), and LDH decreased to 408 from 1333 (FIG. 25). Her CTC showed a marked reduction. These results were obtained after 13 treatments.

Thereafter, her treatment frequency was decreased to twice a week, and she started Afatinib in combination with epigenetic therapies consisting of IV Quercetin PG as mainstay of therapy (at a dose of 0.5 grams). Her laboratory tests were repeated about 2 weeks after initiation of treatment which showed another marked reduction in all her markers—CA 15-3 decreased from 2832 2 weeks earlier to 1852 (FIG. 23), and CA 27.29 decreased from 3183 to 2075 (FIG. 24). This was after two weeks and only four treatments.

Her restaging CT scan of chest was performed about 6 weeks after initiation of treatment and showed partial response to interim therapy consisting of improvement in all pulmonary nodules as well as chest lymph nodes. There was substantial reduction in all lesions size noted. The density in the posterior right upper lobe of lung decreased in size from 41×16 mm to 27×8 mm, the density in the posterior left upper lobe, decreased in size from 18×10 mm to 10×4 mm, the nodule in left, medial upper lobe decreased from 12×6 mm to 7×4 mm, the nodule in the left perihilar lesion decreased from 19×14 mm to 11×10 mm, the lesion in posterior right lower lobe decreased from 20×17 mm to 15×12 mm, the left upper paratracheal node decreased from 7 mm to 3 mm, the left perivascular node decreased from 14×9 mm to poorly defined, and a peritracheal node decreased from 13×10 mm to 10×8 mm.

Her tumor markers further decreased as measured again about 6 weeks after initiation of treatment—Her2 decreased to 816.5 (FIG. 22), CA 15-3 decreased to 891 (FIG. 23), CA 27.29 decreased to 771 (FIG. 24), and LDH decreased to 267 (FIG. 25).

Her restaging PET scan about 7 weeks later showed that all her pulmonary lesions, liver lesions, and skeletal lesions had responded to therapy with decreased sizes and metabolic activity of background level. For example, two right hepatic lobe lesions had decreased from 58×43 mm to 42×33 mm and 24×19 mm to 18×16 mm, and nodular density in left upper lobe had decreased from 10×4 mm to 8×5 mm. Her left pleural effusion was decreased in size. There was a necrotic mass in the right breast and positive response to therapy with increasing sclerosis in all skeletal bony metastases.

Her tumor markers continued to decrease as measured around the time of her restaging PET scan—Her2 decreased to 145 from 816 (FIG. 22), CA 15-3 decreased to 259 from 891 (FIG. 23), CA 27.29 decreased to 233 from 771 (FIG. 24), and LDH decreased to 159 from 267 (FIG. 25).

In summary, such drastic response to the disclosed epigenetic therapy, alone and in combination with afatinib, in a patient with advanced and recurrent breast cancer was unexpected. In conclusion, patient's initial response to the epigenetic therapy alone was unexpected and further addition of anti-cancer agent showed additional improvement that was unexpected because the patient was unresponsive to this class of anti-cancer agents alone and based on current literature there is no expected clinical benefit from this particular drug in this type of cancer.

Example 17—Case Study—Julie—Treatment of Breast Cancer with Quercetin PG+SPB+Afatinib This is a case study of 47 year old female with history of left triple positive breast cancer status post insulin potentiation therapy in Phoenix at Uromed, with reportedly good response. However, as she continued her alternative approach by self-administration of supplements and IV Vit C and Ozone at alternative centers in Arizona, and further Hoxy treatment at a Biomedical Center in Mexico, her disease progressed rapidly, initially developing pulmonary metastases and pleural effusions, which required chest tube placements and finally pleurodesis at Ridgecrest Hospital. She further developed hepatic metastases about 5 years after her initial diagnosis as well as diffuse metasatatic disease evident in her recent bone scan. She had tried tamoxifen for 10 months starting 8 months earlier until switching to anastrazole about 10 months later.

She had exhausted all non-toxic therapeutic options. Upon her arrival at the clinic of Dr. Nezami, she had back pain, was unable to walk, and was on a wheelchair.

An MRI of the spine and brain was performed, which showed widespread metastatic disease in brain (largest lesion 2 cm) as well as pelvis with pathological fractures mainly in right pelvis requiring a right hip replacement, which was performed about 5 months after her arrival at the clinic of Dr. Nezami.

She reported reduced pain after the very first treatment. After two weeks of leave due to the surgery, she was started on combination therapy of daily IV epigenetic therapies along with targeted therapies in this situation with -Afatinib. She did not receive any hormonal blockade. She received 12 IV therapies in total after which her laboratory tests were repeated.

Figure 26:
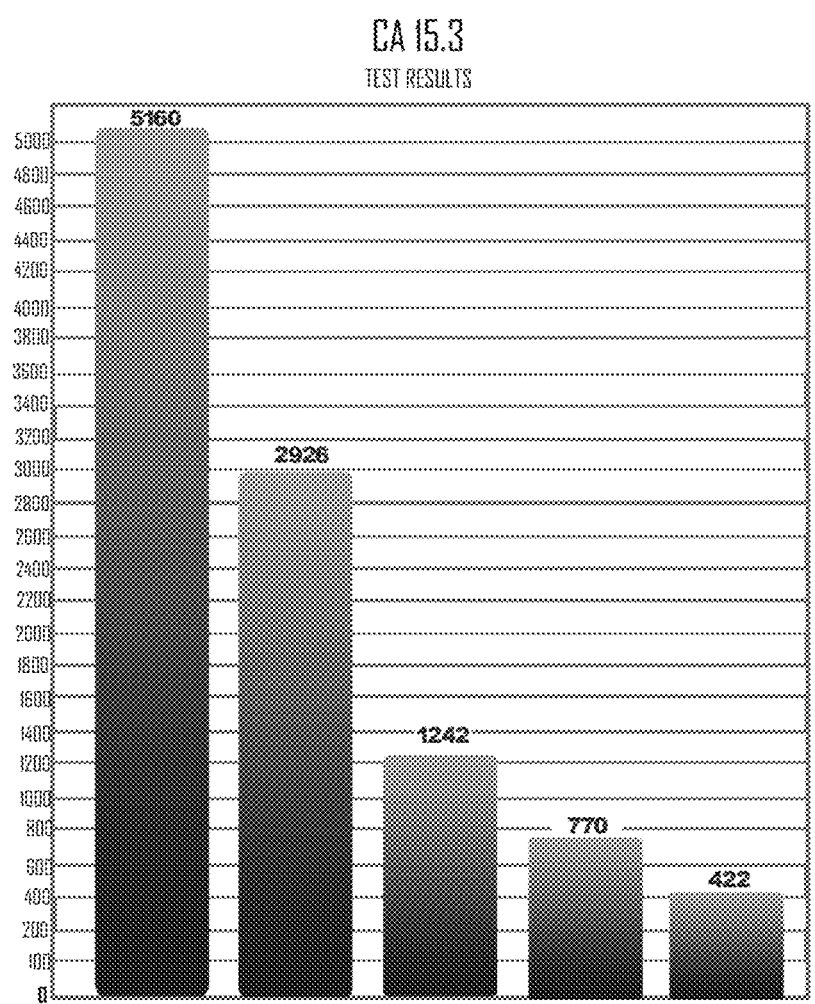
FIG. 26 shows an embodiment of a graph of CA 15-3 antigen levels before and after treatment (See, Example 17).
Figure 27:
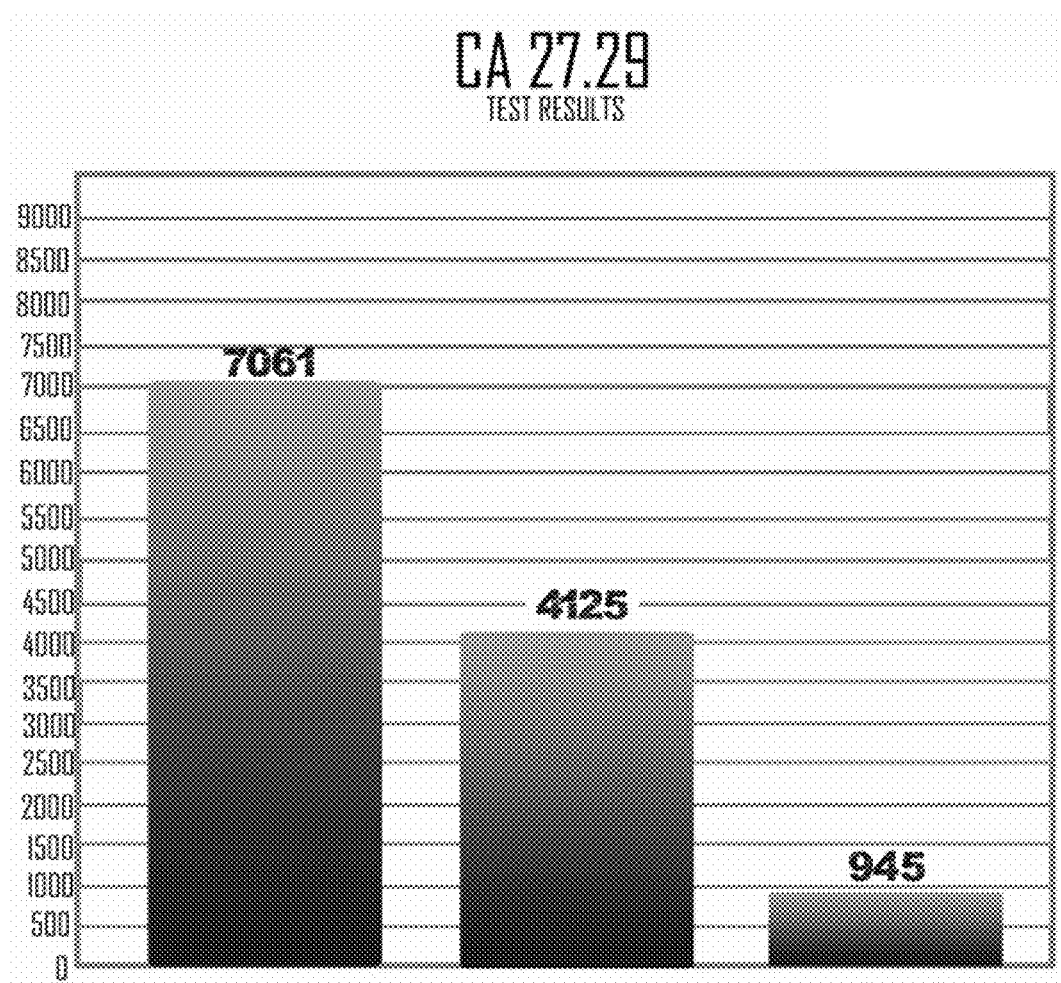
FIG. 27 shows an embodiment of a graph of CA 27.29 antigen levels before and after treatment (See, Example 17).
Figure 28:
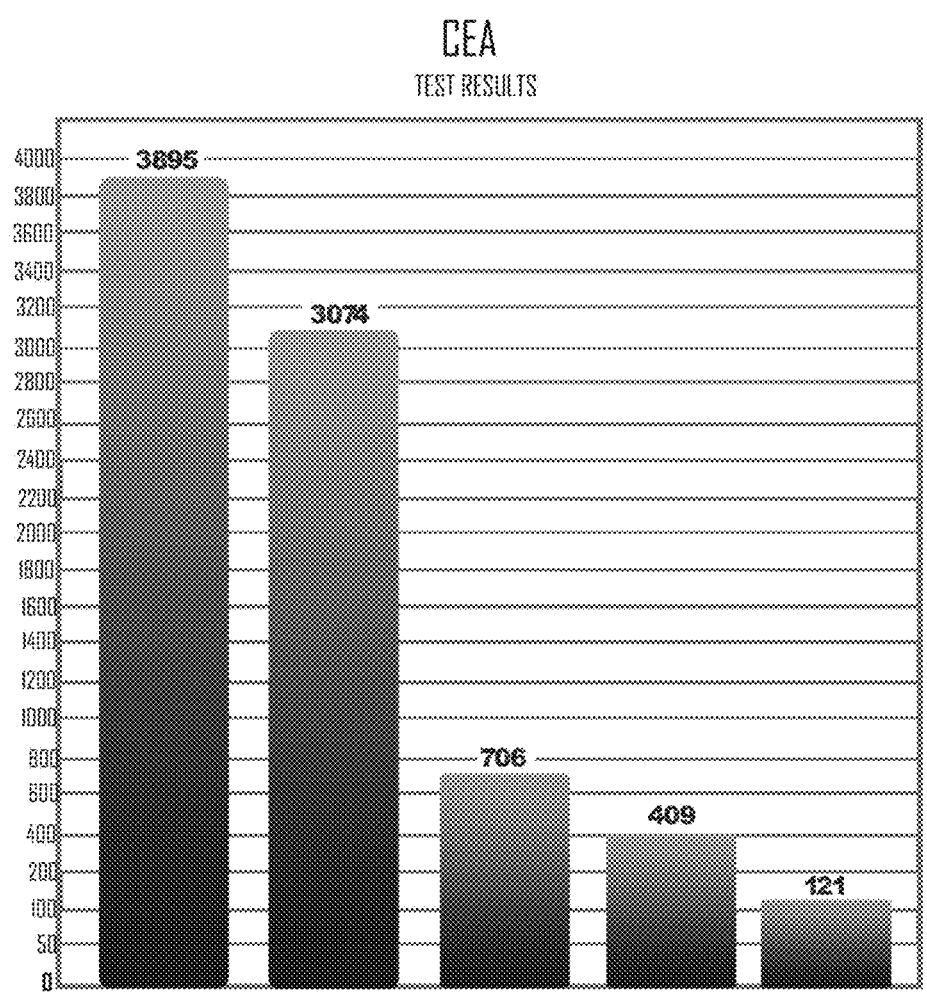
FIG. 28 shows an embodiment of a graph of CEA antigen levels before and after treatment (See, Example 17).

At this time, the patient reported feeling much better. Her ECOG had improved and her tumor markers had decreased. Her CA 15-3 had decreased from 5160 to 2926 (FIG. 26), CA 27.29 has decreased from 7061 to 4125 (FIG. 27), and CEA had decreased from 3895 to 3074 (FIG. 28), and serum Her2 had decreased from 1608 to 835 (FIG. 49). Her laboratory tests were repeated about 2 weeks later and showed further significant reduction in all tumor markers in just two weeks. Her CA 15-3 decreased to 1242 from 2926 (FIG. 26), CEA decreased from 3074 to 706 (FIG. 28), LDH normalized at 210, ALK-P decreased to 364 from 414, platelets decreased from 586 down to 467 (reduced angiogenesis), and anemia recovered with hemoglobin of 10.8 from 9.4. Her laboratory tests were repeated again about 10 days later and showed marked reduction of all markers—serum Her2 was at 144 (FIG. 49), CA 15-3 was at 770 (FIG. 26), CA 27.29 was at 945 (FIG. 27), and CEA was at 409 (FIG. 28).

Her markers continued to decrease further. Her CA 27.29 decreased to 453. Her CA 15.3 decreased to 422 (FIG. 26), and her CEA decreased to 121.7 (FIG. 28), and Her2 was at 77.4 (FIG. 49). She was restaged with a whole body PET scan and the following results were obtained.

Extensive disease burden was described in prior CT. However, current exam showed reduced sizes and minimum metabolic activity in following areas—breast mass, decreased in size, all mediastinal, hilar lymphadenopathies resolved, right lower lobe pulmonary lesion decreased in size from 2.0 cm to 1.2×0.9 cm, with SUV activity of 1.1. All pulmonary lesions were reported with minimum FDG uptake. Large pleural based mass was reported necrotic, with peripheral activity of only 2.4. The liver lesions decreased in size, the largest 7.4 cm from 7.8 cm. The large sternum bony lesion disappeared, the malignant spinal soft tissue and spinal cord narrowing reported on prior exam at levels of T4 and T10 had completely disappeared.

In summary, the dramatic response observed in this patient has to our knowledge not previously been reported in the literature. In conclusion, patient's initial response to the epigenetic therapy alone was unexpected and further addition of anti-cancer agent showed additional improvement that was unexpected because based on current literature there is no expected clinical benefit from this particular drug in this type of cancer.

Example 18—Case Study—Joe—Treatment of Melanoma with Quercetin PG+SPB, Quercetin PG+Temodar, and Quercetin PG+Temodar+Trametinib This case study is of a 51 years old male patient with a history of stage II melanoma diagnosed after a biopsy of his right thumb. The patient received no treatments. His cancer recurred 11 years later in his right axilla. One month later 28 lymph nodes were removed from his right axilla 14 of which were positive for melanoma. The patient received immune therapy in the Bahamas. However, his cancer progressed as evident in his scan about 4 months later showing extensive involvement of his right axillary and subpectoral lymph nodes with SUV activity of 7.7, subcutaneous nodules, and right upper back, right supraclavicular fossa with SUV activity of 6.3, right upper lobe of the lung with SUV activity of 5.5, and lymph nodes in the heart septum.

The patient was asymptomatic. However, the patient emphasized that there were new lesions and nodules that he felt all over his body including his right thigh and left neck. On examination, he had palpable new lesions in his occiput, neck and right axillary lymph nodes.

At the start of his treatment, molecular detection of circulating tumor cells (CTCs) was performed as follows. In order to obtain circulating tumor cells from the patient's peripheral blood, large cells and cell-clusters as well as epithelial cells were isolated. A preparation of mononuclear cells (MNC) served as a control cell fraction. mRNA was isolated from all fractions. Thereafter, the expression of tumor relevant genes was measured by quantitative real-time RT-PCR. A preparation of mononuclear cells (MNC) served as a control cell fraction. C-KIT is a growth factor receptor which may be overexpressed in different kinds of tumors. N more than 50% of early stage melanomas, expression of C-KIT has been described.

His laboratory tests showed a positive circulatory DNA (i.e., cell-free DNA (cfDNA)) positive for NF-1 prior to therapy. His CTC also turned out to be positive for C-KIT prior to the treatments. His S100B was elevated at 120 (normal less than 96), prior to the treatments about 2 weeks after his scan and further increased to 430. His molecular profiling of his tumor showed positive NF-1 mutation as well as positive MGMT. His PDL-1 was negative.

He was immediately started on IV epigenetic therapies consisting of intravenous Quercetin PG as mainstay of therapy in conjunction with sodium phenyl butyrate (SPB) on daily basis, which he received for two weeks.

His IGF-1 decreased from 232 to 216 about 1 month later. His S100B initially went up to 180 and 430 and then decreased to 270. His CTC showed resolution of C-KIT positive CTC, but were positive for telomerase. He was then started on IV epigenetic therapies consisting of intravenous Quercetin PG as mainstay of therapy in conjunction with Temodar (on 1-5 day schedule/28), which he received for two cycles. Thereafter, his laboratory tests were repeated post therapy and following results were obtained.

Figure 29:
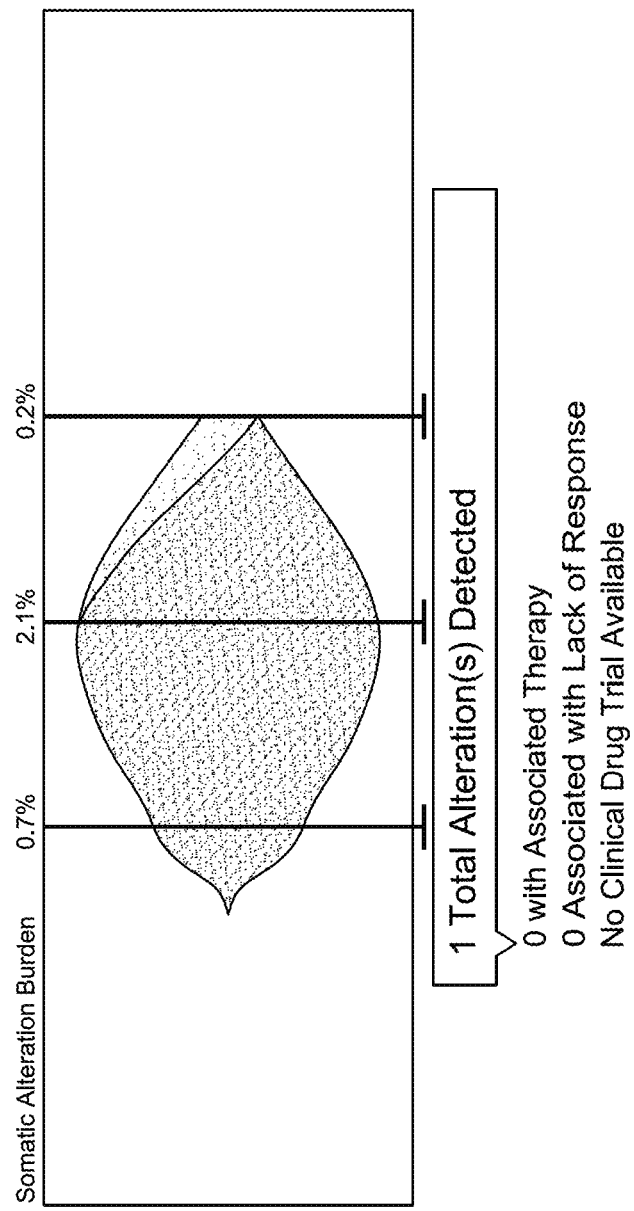
FIG. 29 shows an embodiment of a Guardant360 Tumor Response Map (See, Example 18).

His IGF-1 further decreased to 161 about 1 month alter. These results were obtained without any chemo or targeted therapies. As described above, the Guardant360 Tumor Response Map (FIG. 29) illustrates the mutant allele percentage (% cell-free DNA (cfDNA)) of observed somatic variants at each sample submission time point. His cfDNA showed a high MAF of 0.7 and 2.1 percent before therapy, decreased to 0.2 about 1 month post therapy (FIG. 29).

After 3 months of therapy, targeted therapies (Trametinib) were combined to his regimen (i.e., Quercetin PG+Temodar+Trametinib), which he received for two cycles (i.e., for two months). His scan was repeated post therapy and following results were obtained.

His PET scan about 2 weeks later showed that he achieved a complete remission with resolution of all his original and metastatic lesions (including axillary, subpectoral, supraclavicular, upper back and left abdominal wall, left lower extremities, intrapartum septum in the heart, cervical, pulmonary, right upper lobe, and groin) compared to his scan 5 months ago. His S100B had decreased from 432 to 70 measured about 18 weeks after initiation of treatment, which further decreased to 53 about 2 months later.

His PET scan was repeated 2 days later and showed complete resolution of subcentimeter nodule in his leg, with near complete resolution of all metastatic disease. As this patient did not have a mutated BRAF gene, the response to the combination of Trametinib and epigenetic protocol was unexpected. It is noticeable that his maximum response was achieved with the combination of such therapies.

Figure 30:
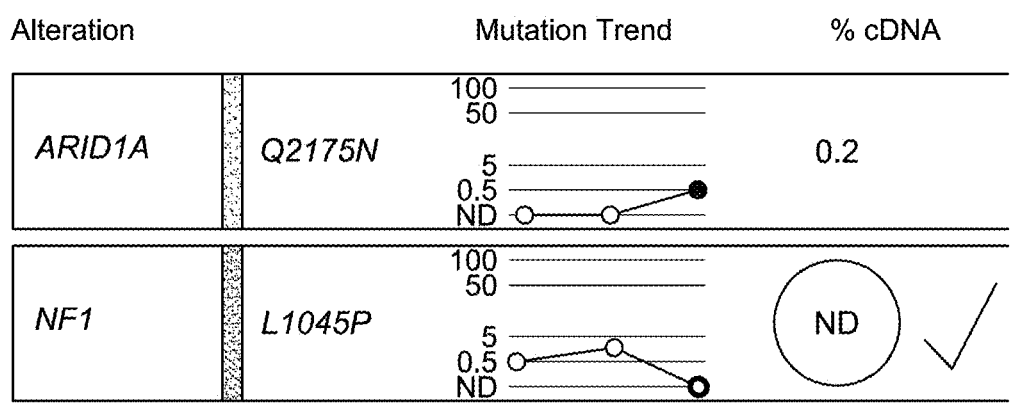
FIG. 30 shows an embodiment of a summary of somatic alterations (See, Example 18).

The expression of the telomerase gene can be increased in most tumor types but not in normal tissue. An increased expression of telomerase gene may be indicative of the presence of tumor cells in the circulation. Post therapy, his NF-1 was undetectable (FIG. 30).

In summary, the unexpectedly positive results with this patient were achieved after about 5 months of IV epigenetic therapies. This case of advanced stage four metastatic melanoma and its response to therapy according to the present disclosure is exciting and further emphasizes the importance of the combinatorial therapeutic approach described in this application. To the Applicant's knowledge, such results have not been previously reported in the literature.

Example 19—Case Study—Arlene—Treatment of Non-Hodgkin's Lymphoma with Quercetin PG+SPB and Quercetin PG+Rituximab This is a case study of a 61 year old female with a history of stage IV Non-Hodgkin's Lymphoma diagnosed and confirmed by pathology with Ki 67 of 80 percent (indicative of high risk). The patient status post chemotherapy 7 months later (R-CHOP (R CHOP=Rituximab, Cyclophosphamide, Vincristine, Adriamycin, Prednisone) every three weeks for 8 rounds, was that the patient had extensive retroperitoneal mass, pleural effusion and mediastinal mass, with residual disease in her retroperitoneum with SUV activity of 2.

The patient was referred to the clinic of Dr. Nezami for evaluation. Her initial complaint was back and flank pain. Patient's initial laboratory results about 1 month after completion of prior chemotherapy confirmed presence of thrombocytosis (marked elevation in platelets, 445) suggestive of tumor angiogenesis as well as slight anemia, low creatinine (muscle mass) and lymphopenia which was confirmed to be along low natural killer cell activity.

Genetic profiling of the patient was performed on the original biopsy, which was positive for TET2, Rb1 and ARID1A genetic polymorphism and mutation, and which categorized her at highest risk of recurrence and progression of disease with no available conventional therapy at this time.

After initial laboratory tests, the patient was started on daily IV epigenetic therapies consisting of IV Quercetin PG and sodium phenyl butyrate for two weeks. She then received targeted epigenetic IV therapies on three times a week basis, for 2 weeks and then on weekly basis. Her pain was immediately alleviated after two weeks. Her laboratory tests were repeated after about 4 weeks which confirmed normalized platelets (from 483 to 394), creatinine, CBC (hemoglobin from 11 to 12). Her lymphopenia disappeared (ALC increased from 400 to 700) and her CRP also decreased from 7 to 3. Her natural killer cell activity (correlated with overall survival by studies in lymphoma patients) was also increased as well (from 20 to 30).

Her PET scan about 3 months later confirmed resolution of the retroperitoneal mass/activity. While there was one lymph node in thyroid, which was confirmed by biopsy as stage one lymphoma; otherwise her scan was normal.

The patient was then treated with bendamustine and rituximab per protocol which was combined with our treatment pre and post therapy.

Her CA 125 immediately decreased from 62 to 42, measured about 3 months and 5 months after initiation of treatment, and further decreased to 26.7 (normal) about 6 months after initiation of treatment.

Her restaging PET scan was performed about 5 months after initiation of treatment which confirmed complete response with no evidence of residual malignancy. She continued the epigenetic therapies and despite her double hit pathology and significant risk of recurrence, refused additional chemotherapies as well as radiation as standard of care. She continued her twice a month therapy at the clinic of Dr. Nezami and her restaging PET scan about 8 months after the previous PET scan showed normal scan with no sign of recurrence.

Her VEGF increased to 150 as measured another 5 months alter and was repeated after 7 IV therapies and it decreased down to 48 about another 2 weeks later. Her PET scan was also repeated about 4 months after the last PET scan and it showed no evidence of disease.

In summary, this case study represents successful treatment of a patient using epigenetic therapies independently as well as synergistically with Rituximab without side effects. This patient did not receive the standard dosage or regimen of Rituximab, and was able to accomplish complete remission with only two cycles in combination with epigenetic therapy (IV Quercetin PG).

It is noted that based on clinical definition and evaluation (with Double hit refractory Lymphoma), the patient was not expected to accomplish remission at all, despite all available modalities of care. However, complete remission was achieved with the treatment regimen described herein. In conclusion, patient's initial response to the epigenetic therapy alone was unexpected and further addition of anti-cancer agent showed additional improvement that was unexpected because the patient was unresponsive to the anti-cancer agent alone. The patient had failed Rituximab (R-CHOP regimen) prior to administration of the combination.

Example 20—Case Study—Barbara—Treatment of B Cell Lymphoma with Quercetin PG and Quercetin PG+R CHOP (Rituximab+CHOP)

This case study is of a 75 year old female with history of hemolytic anemia and a negative bone marrow biopsy. The patient was diagnosed with large B cell lymphoma status after an iliac muscle mass biopsy, with a PET scan revealing extensive disease with involvement of parasarcral area, diffuse metastatic lesions in skeletal bone, as well as left adrenal gland. The patient refused chemotherapy initially. Her laboratory tests indicated significantly high LDH (343) as well as anemia (Hgb of 8) about one year later. Her main complaints were paralyzed right leg and significant edema in left lower extremities. She also had a mass in her skull sized 5 cm round and hard in left parietal bone, which was positive in her PET scan.

Against her wish, she received one round of R CHOP with significant bone marrow suppression resulting in urosepsis and refractory thrombocytopenia.

She then arrived at the clinic of Dr. Nezami. At initial evaluation, she was in pain. After initial evaluation, she was started on epigenetic therapies IV which she received three times a week. Her symptoms improved significantly after just a week of treatment. Her CRP decreased and her LDH decreased to 232 (normal range) after about 2 months, and examination revealed that the mass in her skull had completely resolved.

She further decided to receive epigenetic therapies in combination with Rituximab for two rounds. She received in total 17 treatments for about 3 months around this time. Her restaging PET scan was after 3 months of therapy showed complete resolution of all prior identified lesions in her abdominal nodes, pelvis (sacrum, pubic symphysis, acetabulum), presacral region, and adrenal glands. Her prior identified left humoral head lesion showed marked improvement with decreased metabolic activity from 14.8 to 4.7.

In summary, such a dramatic and unexpected response in a patient who had failed standard treatments and had experienced significant toxicity thereof presents a novel treatment approach of such a group of refractory patients. In conclusion, patient's initial response to the epigenetic therapy alone was unexpected and further addition of anti-cancer agent showed additional improvement that was unexpected because the patient was unresponsive to the anti-cancer agent alone.

Example 21—Case Study—Jennifer—Treatment of B Cell Lymphoma with Quercetin PG+SPB+Rituximab and Quercetin PG+SPB This case study is of a 46 year old female patient with a history of enlarged self-explored left supraclavicular LN and confirmed by biopsy one month later (status post biopsy in May). She arrived at the clinic of Dr. Nezami for evaluation and treatment. A staging PET was performed. Clinically she was stable but suffered from some constitutional symptoms, such as night sweats (Staging III B).

She underwent a staging PET scan subsequent to a core and excisional biopsy, which confirmed the diagnosis of diffuse large B cell lymphoma. BCL-2 and 6 were assessed and were positive. C-MYC was reported negative. Her molecular profiling showed positive response to anthracyclines. Her initial PET scan showed 3.5 cm mass in supraclavicular region along with thyroid lesion with metabolic activity of 11.4 and inguinal lymph nodes (LNs). The patient also underwent an MRI which showed several LNs in the neck along with the supraclavicular node, which was around 3.2 cm in size and was biopsied.

Based on ASCO 2015 recommendations, she needed a bone marrow biopsy. It was decided that a bone marrow biopsy would be performed if her scan was positive post therapy. Results also showed positive involvement of right iliac node as well as thyroid with very high SUV activity of 18 and 11, respectively, pre-therapy.

The prognosis and the data in regards to R CHOP versus B+R were explored, based on the multi-center phase III trial presented at ASCO 2012.

She was then started on combination of IV epigenetic therapies, consisting of Quercetin PG and sodium phenyl butyrate in combination with Rituximab, which she received for 10 days prior and during the Rituximab injections.

She received two cycles of Rituximab plus epigenetic therapies. It was decided that the standard treatment with Rituximab was not required further. She reported resolution of her neck and inguinal mass post therapy. Her laboratory tests confirmed normal beta 2 microglobulin, LDH, and IL-2 receptor levels. Her restaging PET scan confirmed complete resolution of her thyroid, inguinal, and pelvic LNs as well as the supraclavicular node.

The patient continues to receive maintenance IV epigenetic therapy on bimonthly basis. The patient has not received any targeted therapies or chemotherapies since. She has been in complete remission for over 18 months.

In summary, the drastic and impressive response observed with the combination of rituximab and Quercetin PG+SPB can be translated into a novel therapeutic option and a replacement for currently used standard treatment in hematological cancer. In conclusion, patient's initial response to the epigenetic therapy alone was unexpected and further addition of anti-cancer agent showed additional improvement that was unexpected because the patient accomplished remission prior to completion of her chemotherapy regimen. The standard treatment for her type of cancer is R CHOP, which she did not receive. While Rituximab is given for 6 cycles, the patient did not have to receive 6 cycles because after only 2 cycles she was cancer free.

Example 22—Case Study—Sarah—Treatment of Hodgkin's Lymphoma with Quercetin PG+SPB+Rituximab This is a case study of a 22 year old female patient with history of Hodgkin's lymphoma diagnosed after one year of presence of a neck mass. The patient was treated with antibiotics after a left neck mass excisional biopsy—her fine needle biopsy was negative. She sought second opinions about her care, was asymptomatic except the palpable mass that was close to her throat.

Initial laboratory results suggested increased angiogenesis, based on her increased platelets at 469. Her pathology also shows infiltration of T Cells, and based on the literature, placed her in the gray zone for nodular type of lymphoma.

Several level 4, left neck LNs were seen in the PET/CT with high SUV activities of 9, and involvement of portocaval node with SUV activity of 6.3 below the diaphragm. The patient was staged at IIIA. Molecular profiling showed that she had negative PDL-1. She had high CRP at 113 and increased platelets at 397.

She was started on combination of IV epigenetic therapies, consisting of Quercetin PG and sodium phenyl butyrate which she received on daily basis with Rituximab, for two cycles. She did not receive any other chemotherapy.

Post therapy, laboratory tests indicated that her platelets had decreased to normal range, her hemoglobin had improved to normal range (increased from 8 to 12), as well as her LDH had decreased to 157 from 250.

She regained her function and energy.

The re-staging PET showed near resolution of several LNs as well as significant reduced metabolic activity and size in others. For example, her portocaval and many thoracic LNs disappeared, and her left neck LNs SUV activity decreased from 9 to 4.

In summary, the observed response with only targeted and epigenetic therapies, with no use of cytotoxic therapies in a case of Hodgkin's lymphoma is highly impressive. In conclusion, patient's initial response to the epigenetic therapy alone was unexpected and further addition of anti-cancer agent showed additional improvement that was unexpected because it was not expected that Rituximab alone would have any objective measures of response and it was unexpected to see such an outcome.

Example 23—Case Study—Manny—Treatment of Mantle Cell Lymphoma with Quercetin PG+SPB and Quercetin PG+SPB+Ibrutinib This is a case study of a 69 year old male diagnosed with mantle cell lymphoma on an orbital mass, which was confirmed by pathology by "maxichop" protocol. The patient referred to the clinic of Dr. Nezami for epigenetic evaluation and treatments. His chief complaints were fatigue and depression. He originally was treated with four cycles of Maxi-CHOP about one month after initial diagnosis, although Vincristine was excluded from his protocol due to severe neuropathy in his hands. He refused further chemotherapy secondary to severe side effects. Laboratory tests were performed about 2 months later, which revealed increased LDH that is encountered as the tumor marker for his type of cancer, as well as increased ferritin that can correlate with prognosis as acute phase reactant (correlation seen with prognosis in leukemias and lymphomas). His pathology originally was positive for both BCL and Ki 67 and his macroglobulin was elevated, all suggestive of poor prognosis and aggressiveness of his cancer.

His initial laboratory test results showed LDH of 252, and ferritin of 850 and presence of metamyelocytes and myelocytes.

He was immediately started on the epigenetic IV protocol consisting of IV Quercetin PG and sodium phenyl butyrate. After three sessions his fatigue level decreased and his function increased. After 5 treatments, his laboratory tests were repeated. His LDH (tumor marker) had decreased to 231, his ferritin to 509 and his beta 2 microglobulin showed normal results—increased levels were seen in his electrophoresis before starting the treatments.

His metamyelocytes and myelocytes had both disappeared in his laboratory tests after the 5 sessions of therapy. His LDH normalized at 132 about 1.5 months after initiation of treatment. His CRP decreased from 56 to 0.5 over the course of about 2 months of treatment. His natural killer cell activity increased from 14 to 19 between over the course of about 3 months of treatment and to 51.1 about 7.5 months after initiation of treatment. His IGF-1 decreased from 218 about 2.5 months after initiation of treatment to 133 about 3.5 months after initiation of treatment.

His bone marrow biopsy was negative for malignancy about 7 weeks after initiation of treatment, and his PET scan was negative reported about 3 months after initiation of treatment, giving him diagnosis of complete clinical remission.

Further he stopped all treatments (both conventional therapies and therapies administered at the clinic of Dr. Nezami) about 9 months after initiation of treatment (in two months) despite being advised otherwise, and his LDH went up to 404 measured about 2.5 months later. He was again immediately started on the epigenetic therapies. His LDH levels decreased in about a week to 308 and further decreased to 265 in two weeks and decreased to normal at 206 in three weeks. His beta 2 microglobulin also decreased from 1.7 to 1.2 and his WBC improved from 3.3 to 4.6 after 6 treatments.

His PET scan about 2 months later confirmed the response to therapy, no active FDG avid recurrent or metastatic lymphoma was identified.

He had a local recurrence on his left orbit about 8 months later, which was reported with a focal FDG avid lesion in PET scan. He was immediately started on the IV epigenetic therapy on a twice weekly program in combination with Impruvica (Ibrutinib), and continued the program for 4 weeks, after which a restaging PET scan revealed complete resolution of the lesion with normal activity.

The patient is currently on maintenance IV epigenetic therapies on once weekly basis in combination with Ibrutinib (Impruvica) at 25 percent dosage, and has no evidence of recurrence, evident in his images performed every three months.

Such a dramatic response in a short period of time in a patient with a rare but very aggressive type of lymphoma with significant genetic markers for aggressiveness has not been previously reported. In conclusion, patient's initial response to the epigenetic therapy alone was unexpected and further addition of anti-cancer agent showed additional improvement that was unexpected because the patient was unresponsive to several categories of the anti-cancer agent alone. It was also unexpected to see durable response in such advanced case of lymphoma without using chemotherapy. Additionally, the combination of epigenetic therapies had reduced the requirement of targeted drug (Ibrutinib) to 25 percent of recommended dose.

Example 24—Case Study—Thomas—Treatment of CLL with Quercetin PG+SPB and Quercetin PG+SPB+Ibrutinib This a case study of a 64 year old male patient with history of CLL with extreme fatigue and constitutional symptoms after several alternative therapies, including Vit C, ozone, supplements, who was in consultation with at least two oncologists, and yet had not received a biopsy or PET scan.

He presented with a very bulky mass in his left axilla, as well as many other LNs (extensive lymphadenopathies in chest, abdomen, pelvis, inguinal nodes) presenting in his last CT about 8 months after his diagnosis. He was evaluated initially at the clinic of Dr. Nezami about 2 years after his initial diagnosis and his laboratory test results showed increased WBC at 30,000. His soluble IL-2 receptor was at 3589. His beta 2 microglobulin was at 2.9, and his LDH was elevated at 281.

A whole body PET scan was performed which showed extensive lymphadenopathy in neck, thorax, inguinal, abdomen and pelvis, which had increased when compared to his previous PET scan about 8 months ago. Bone marrow biopsy also performed which showed 80 percent lymphocyte infiltration with ATM deletion and ch13 del. ATM gene alteration is a frequent event in pathogenesis of chronic lymphocytic leukemia (CLL) and occurs as monoallelic loss in the form of 11q23 deletion. ATM is a principal DNA damage response gene. His blood flowcytometry also showed a CD38 of 50 percent (more than 30 is correlated with poor prognosis).

Molecular profiling of his bone marrow biopsy showed positive pathogenic and activating mutation at NOTCH1. As a result, he was started on IV epigenetic therapies which inhibit HDAC, consisting of IV Quercetin PG and sodium phenyl butyrate.

The patient received 10 treatments in total in two weeks. Laboratory tests post treatments showed improved WBC (decreased to 26,000) and lymphocytes (decreased to 12.6 from 14.8). His LDH decreased to normal at 220 from 281. Beta2 microglobulin decreased to 2.5 from 2.9. His IL-2 receptor was 3582. His LASA also decreased from 28 to 26. His IL-2 receptor also decreased from 3589 to 1684 after 22 rounds treatments.

His QOL improved and his counts confirmed response to the two week of treatments.

After continuing the IV epigenetic therapies for another two weeks, therapies were combined with Ibrutinib which he received at 75 percent dosage. His laboratory tests were then repeated which showed significant reduction of his other markers as well. His LDH stayed at normal level down to 216, CRP was at 10, Beta 2 microglobulin had decreased to 1.7 from 2.5.

In summary, such a significant clinical outcome obtained without the use of chemotherapies provides evidence of using combinational epigenetic and targeted therapies in refractory and advanced lymphomas. In conclusion, patient's initial response to the epigenetic therapy alone was unexpected and further addition of anti-cancer agent showed additional improvement that was unexpected. It was unexpected to observe any response in such advanced case of lymphoma without using chemotherapy. Additionally, the combination of epigenetic therapies had reduced the requirement of targeted drug (Ibrutinib) to 75 percent of recommended dose.

Example 25—Case Study—Dara—Treatment of NSCLC with Quercetin PG+SPB+Crizotinib

This is a case study of a 47 year old female patient with history of non small cell lung cancer (T1a, N2, M0) diagnosed after many alternative therapies which included IV vitamin C and naltrexone. She initially had a right lower lobe mass and underwent lobectomy and 4 cycles of chemotherapies consisting of Carboplatinum. There was a recurrence of the tumor about 3 years later presenting by cough. A further biopsy was done about 3 months alter. She received chemotherapies consisting of Taxol starting about one month later for about 2 months and radiation therapy for about 3 months.

Unfortunately, her tumor had progressed in her last PET performed about 7 months later showing multiple lesions left lower lobe and hilar LNs bilaterally. She had consulted two different oncologists and the oncologists prescribed Crizotonib (Xalkori) due to mutated ALK. She had started taking Crizotonib just a few days prior to arriving at the clinic of Dr. Nezami.

She was also experiencing some pain due to her sciatica problem. She was immediately evaluated and her laboratory tests showed her Interleukin 8 serum to be elevated. She was started on treatments comprising Quercetin PG+SPB+Crizotinib on a daily basis for 10 days. Laboratory tests were repeated and IL-8 decreased from 66 to 8.5 in about 10 days. She did not change her diet or received any other therapies.

About one month later, her PET scan was repeated which showed stable disease in CT, and a mix pattern of response. For example, PET scan revealed that the activity in her cervical LNs had decreased from 8.2 to 2.5 and her pulmonary node increased from 5.4 to 8.2.

In summary, such a response in a stage four lung cancer (tumor stabilization in CT and a mixed pattern in PET) was unexpected, especially considering the fact that she had already failed prior radiation and chemotherapies and had progressed significantly prior to the treatment. In conclusion, the patient's response to combinational therapy was unexpected as the magnitude of response was unexpectedly quick. In her case, the antineoplastic response was documented only after 4 weeks of combinational therapy, which is not seen in application of targeted drug alone.

Example 26—Case Study—Jack—Treatment of Prostate Cancer with Quercetin PG+Crizotonib This is a case study of a 70 year old male patient with history of metastatic prostate cancer diagnosed as a localized disease with Gleason score of 8 and PSA of 3.1!

He underwent prostatectomy and hormonal blockade with Casodex and Lupron which failed due to bone metastases in lumbar spine about 8 years later. His PSA was reported at 44. He started clinical trial with Enzalutamide and Abriterone at UCSF, which was ultimately stopped after about three months due to severe hyponatremia. During this time his PSA was reported undetectable. He presented to the clinic of Dr. Nezami for a second opinion and evaluation. He had a recent MRI which showed extensive lumbar spine involvement both lytic and sclerotic some of which were irradiated.

At the start of his treatment, molecular detection of circulating tumor cells was performed as follows. In order to obtain circulating tumor cells from the patient's peripheral blood, large cells and cell-clusters as well as epithelial cells were isolated. A preparation of mononuclear cells (MNC) served as a control cell fraction. mRNA was isolated from all fractions. Thereafter, the expression of tumor relevant genes was measured by quantitative real-time RT-PCR. A preparation of mononuclear cells (MNC) served as a control cell fraction.

The expression of the telomerase gene can be increased in most tumor types but not in normal tissue. An increased expression of telomerase gene may be indicative of the presence of tumor cells in the circulation. Expression of telomerase was not detected in the isolated cells. Overexpression of C-MYC indicates an increased proliferation of the isolated cells. An increased proliferation rate is a typical feature of tumor cells. The expression level of C-MYC was elevated. Overexpression of ERBB2 (HER2/NEU) is a trait of different types of cancer and may also be observed in breast cancer. Thus, the detection of ERBB2 overexpression may be indicative of the presence of circulating tumor cells. The expression of ERBB2 was elevated. Prostate Surface Antigen (PSA) is a gene specifically expressed in prostate tissue. Thus, the detection of an expression of the PSA-mRNA indicates the presence of circulating prostate-cancer cells. No expression of the PSA-gene was detected. Thus, in the isolated tumor cell fraction, expression of ERBB2 and C-MYC was above threshold (>2.0). This finding was indicated of the likely presence of circulating tumor cells in the analyzed blood sample.

On evaluation at the clinic of Dr. Nezami, he underwent a whole body PET scan, which confirmed the presence of extensive bony metastases with maximum SUV activity at L5 (at 13.9), increased CEA at 13.2 (as a poor prognostic factor). His CTC was positive for C-MYC and ERBB2, his cDNA showed amplification of 8 genes, including: CDK4, CCND2, CDK6, Met, Myc, Pi3k, KRAS, and FGFR2 (FIG. 31).

Initial laboratory tests confirmed the increased TGF at 8640 about 11 years after his initial diagnosis. Immediately he was started on daily IV epigenetic therapies consisting of IV Quercetin PG and targeted therapies (Crizotonib). Follow up laboratory tests after about two weeks of daily IV epigenetic therapies showed a marked reduction of TGF down to 4560.

Figure 32:
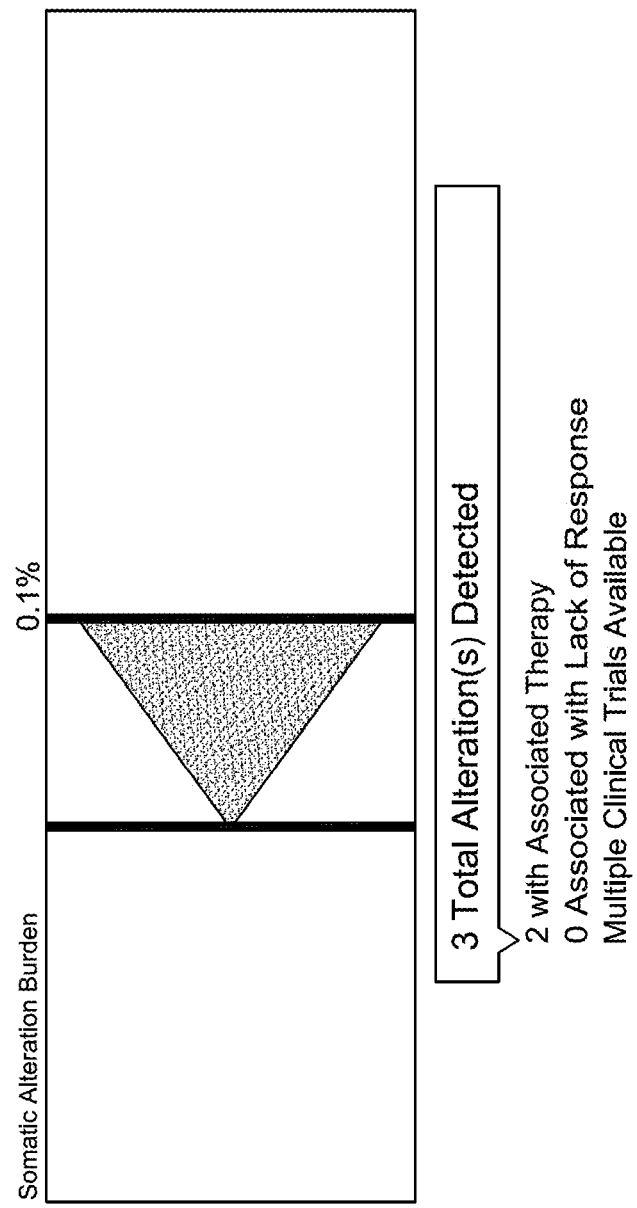
FIG. 32 shows an embodiment of a Guardant360 Tumor Response Map (See, Example 26).

The Guardant360 Tumor Response Map (FIG. 32) illustrates the mutant allele percentage (% cell-free DNA (cfDNA)) of observed somatic variants at each sample submission time point. After about 3 weeks of treatment, his % cfDNA showed disappearance of ERBB2 (as at 0.1% after about 3 weeks of treatment) (FIG. 32).

Figure 33:
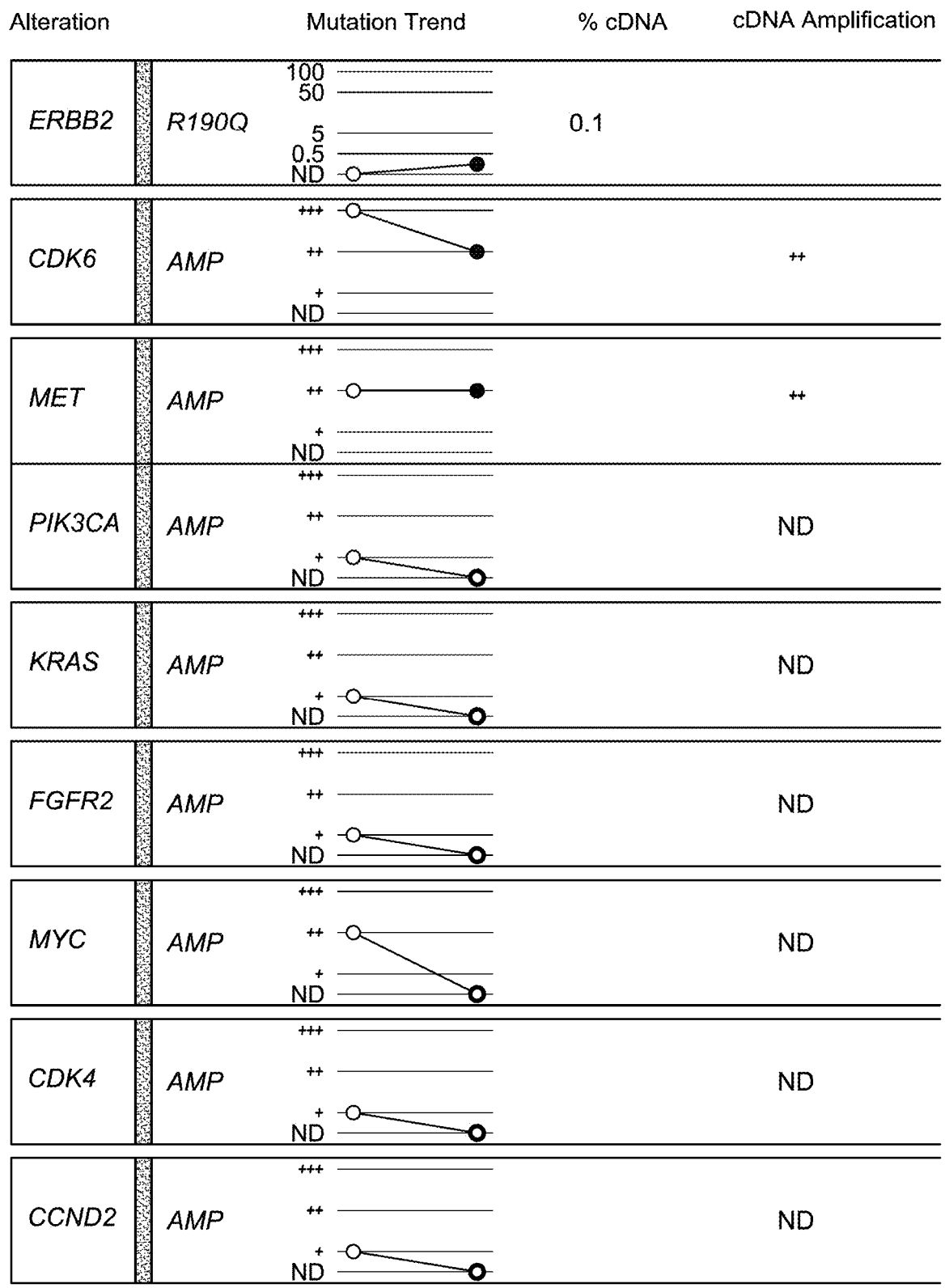
FIG. 33 shows an embodiment of a summary of somatic alterations (See, Example 26).

His TGF decreased to 4000 post two weeks of treatment. His cDNA was repeated and it showed complete resolution of PI3k, KRAS, FGFR2, Myc, CDK4, and CCND2 (FIG. 33). His CDK6 decreased from 3 plus to 2 plus. After about 3 weeks of treatment, expression of telomerase was not detected in the isolated cells, the expression level of C-MYC was not elevated, expression of ERBB2 was not elevated, and no expression of the PSA-gene was detected. Thus, in the fraction of isolated tumor cells, abnormal expression of all measured tumor-associated marker-genes was not observed. Therefore, according to the panel of molecular tumor markers used for this analysis, there were no indications for presence of cancerous cells in the analyzed blood specimen.

In conclusion, patient's initial response to the epigenetic therapy alone was unexpected and further addition of anti-cancer agent showed additional improvement that was unexpected because Crizotonib alone is not approved or suggested as an effective therapy for prostate cancer.

Example 27—Case Study—Mahe—Treatment of NSCLC with Quercetin PG+SPB+Crizotinib

This is a case study of a 57 year old female patient with history of left lung non small cell adenocarcinoma, positive AML4/ALK mutation, who had undergone lobectomy and several rounds of chemotherapies starting with Critozinib and further Carboplatium and Taxol, with initial good response. However, there was recurrence about 6 months later as documented by PET scan showing a left inferior posterior lobe lesion with associated left pleural effusion requiring drainage of 2.0 liters of malignant effusion (confirmed with positive cytology as Stage IV) every two weeks. She referred to the clinic of Dr. Nezami about two months later for evaluation and treatments. Her initial symptoms were severe fatigue and shortness of breath.

Initial laboratory tests confirmed increased CEA (as a prognostic tumor marker for NSCLC) as well as increased LDH, and serum Her2 level at 15.8. She also had lymphopenia (Lymph 5 percent) and chronic kidney failure (Cr=1.36).

She was immediately started on daily IV epigenetic therapies consisting of IV Quercetin PG as main stay of therapy, with SPB, which she received in total for 8 treatments in two weeks. Her symptoms resolved very quickly in one week. Her ECOG score improved over time from 3 down to zero (fully active) post therapy.

Figure 34:
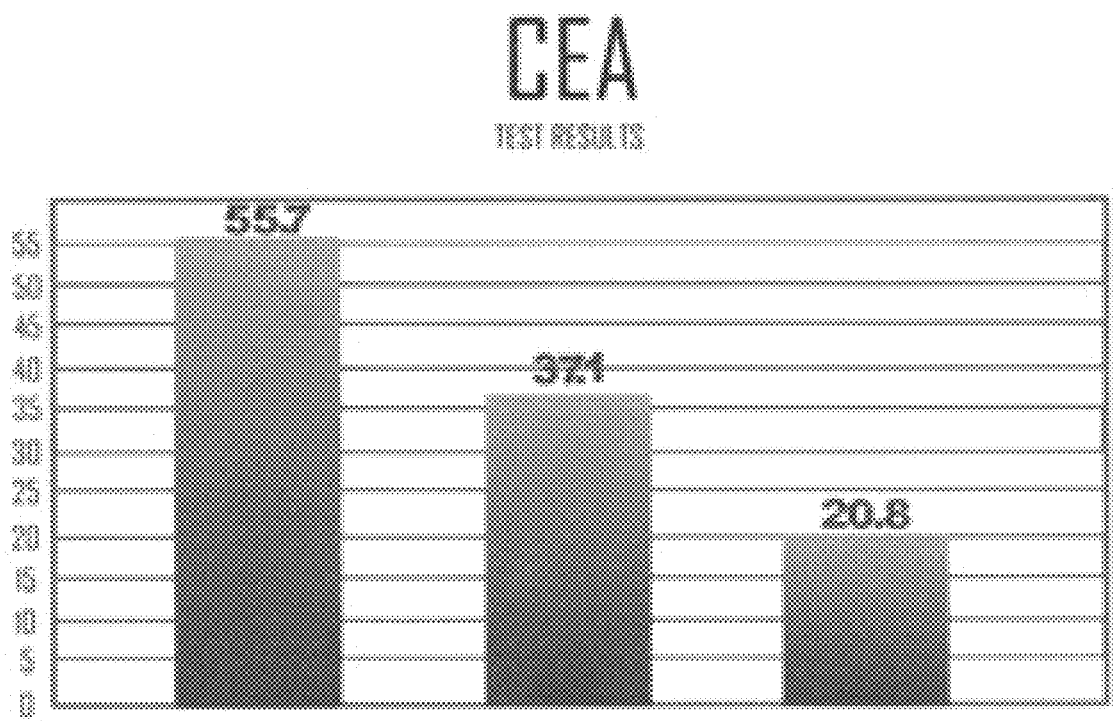
FIG. 34 shows an embodiment of a graph of CEA antigen levels before and after treatment (See, Example 26).
Figure 35:
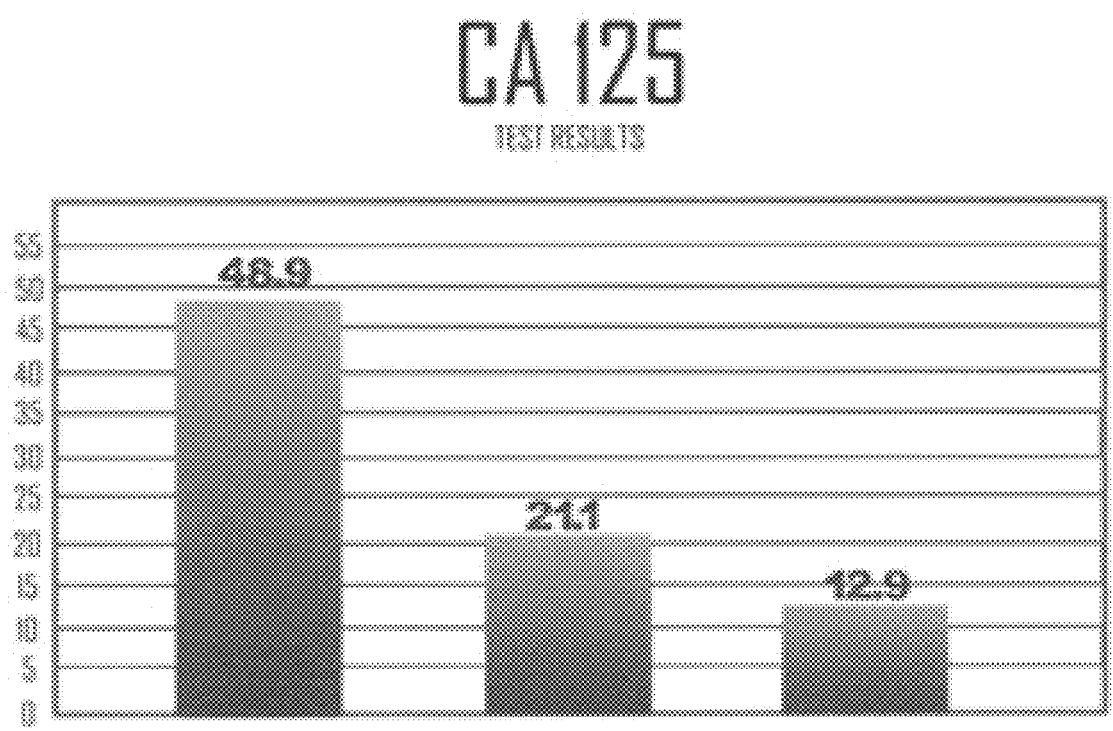
FIG. 35 shows an embodiment of a graph of CA 125 antigen levels before and after treatment (See, Example 26).
Figure 36:
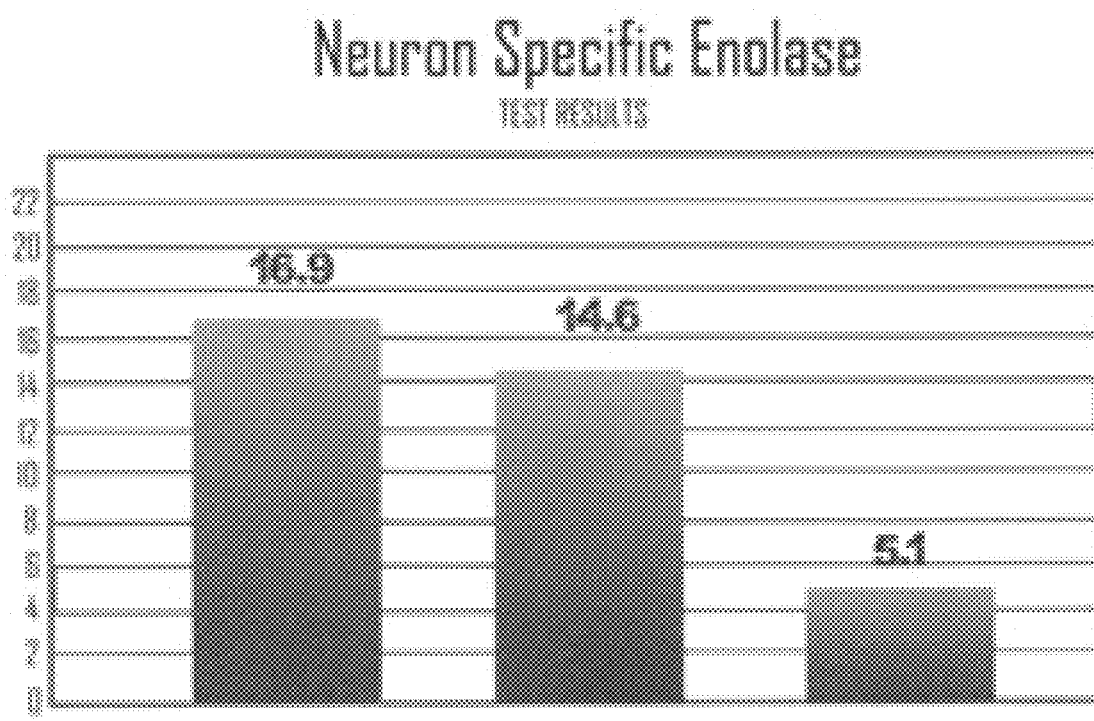
FIG. 36 shows an embodiment of a graph of Neuron specific enolase levels before and after treatment (See, Example 26)
Figure 37:
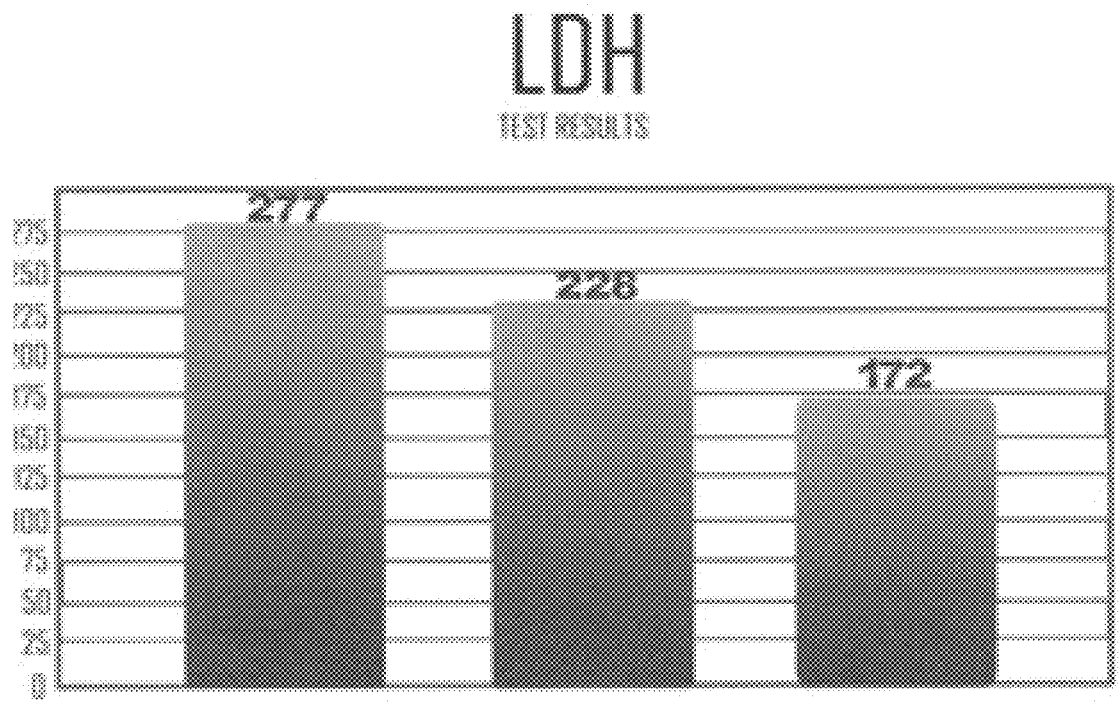
FIG. 37 shows an embodiment of a graph of LDH levels before and after treatment (See, Example 2).

Her laboratory tests were repeated and her Lymphocytes normalized from 5 to 33, her creatinine improved from 1.36 to 1.14, her alk-p decreased from 127 to 118. Her CEA decreased from 55.7 to 37.1 about one week after starting treatment (FIG. 34), and further decreased to 20.8 about another one month later (FIG. 34). Her CA 125 decreased from 48.9 to 21.1 (FIG. 35), further down to 12.9 (normalized) (FIG. 35), her Neuron specific enolase also decreased from 16.9 to 14.6 and further to 5.1 (FIG. 36), her serum Her 2 level decreased from 15.8 to 15.5. Her LDH decreased from 277 to 228, further decreased to 172 (FIG. 37).

Her thoracenthesis scheduled one month earlier, was cancelled due to lack of any pleural effusion documented in her ultrasound.

Her restaging PET scan about 2 weeks after starting treatment showed complete remission, with no evidence of residual tumor and no evidence of distant or local metastatic disease. This represents a tremendous improvement from prior study. On her prior PET scan about 2 months prior to initiating treatment, there was a large pleural effusion in left side with associated posterior intense avid and large FDG (SUV of 9.3) identified in left pleural space.

In summary, this complete response to a resistant and recurrent case of stage four NSCLC, in a matter of less than 8 weeks, is very unusual and surprising. In conclusion, patient's initial response to the epigenetic therapy alone was unexpected and further addition of anti-cancer agent showed additional improvement that was unexpected because the tumor had recurred despite several standard treatments. The magnitude of response was unexpected for a resistant type of lung cancer, in matter of only two weeks.

Example 28—Case Study—Tamara—Treatment of Ovarian Cancer with Quercetin PG and Quercetin PG+Crizotinib This is a case study of a 72 year old female patient with history of stage IV ovarian cancer with several rounds of Carboplatinum and taxol both systemic as well as intraperitoneal with significant residual disease. She was referred to the clinic of Dr. Nezami for evaluation and treatments about 5 months after her diagnosis. She had developed stage IV renal failure due to Carboplatinum toxicity, with creatinine of 1.9 and 1.69 upon her arrival. She was staged with a PET scan that confirmed the presence of subcapsular liver lesions with metabolic activity. She was complaining of pain and nausea, and fatigue. Her laboratory tests confirmed the neutropenia and anemia, as well as increased HE 4 and TGF-beta 1, which were at 284 and 5020, respectively.

She was immediately started on IV epigenetic therapies consisting of IV Quercetin PG, which she received on daily basis, and after 7 treatments the laboratory tests were repeated, which showed marked improvement in her creatinine from 1.69 to 1.48, her anemia and leukopenia. Her WBC recovered to normal from 2.4 to 3.4. Her neutropenia resolved. Her symptoms all recovered and her quality of life (QOL) improved.

Her tumor tissue molecular profiling by NGS showed a positive target for C-MET, Rb1, and P53, and her circulating DNA (% cfDNA) was positive for APC and ALK. Therefore, Crizotonib was added to IV Quercetin PG. Her molecular profiling was positive for ER and TS. Her tumor molecular profiling also showed C-MET overexpression, justifying the combination of Crizotonib with epigenetic therapies. Her circulating tumor cells (CTC) was negative.

Figure 38:
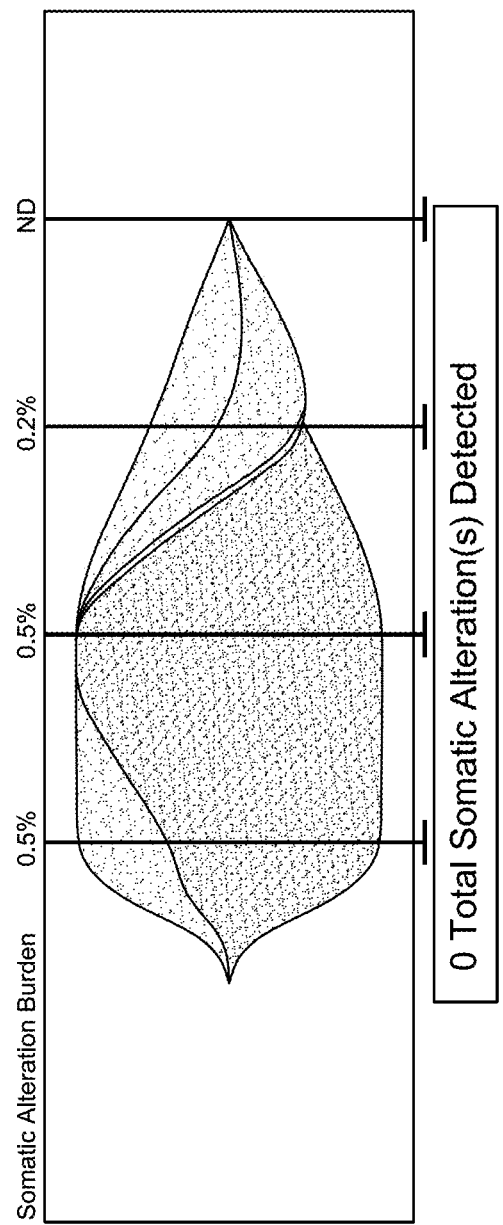
FIG. 38 shows an embodiment of a Guardant360 Tumor Response Map (See, Example 28).
Figure 39:
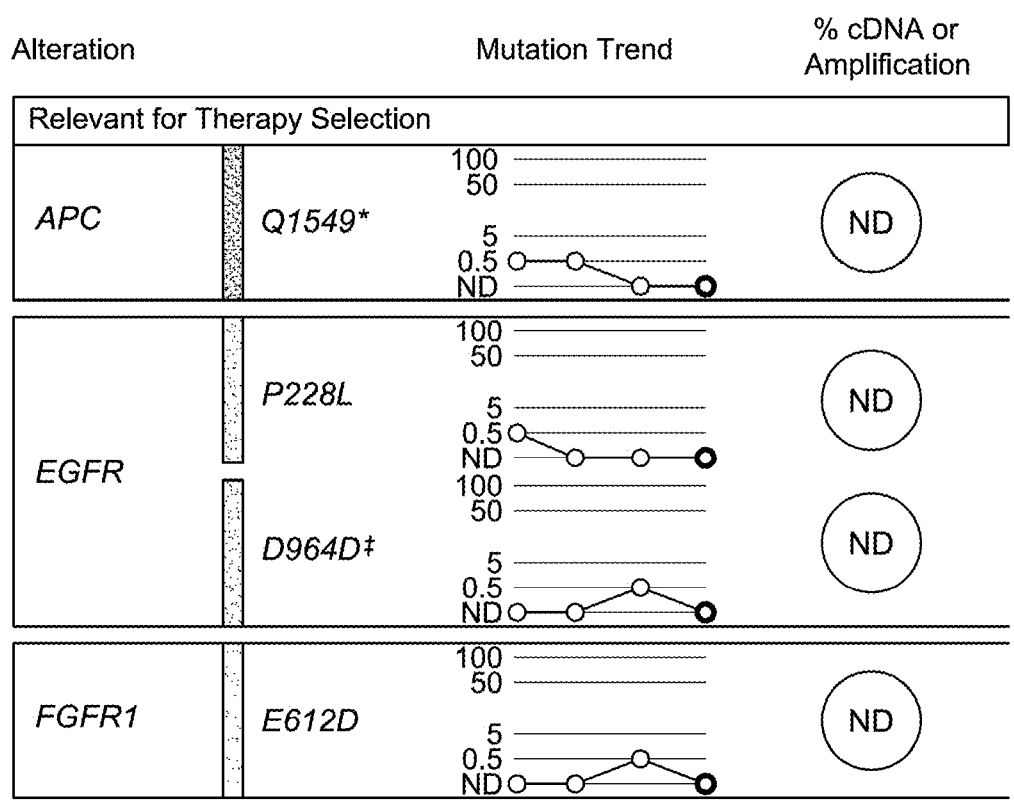
FIG. 39 shows an embodiment of a summary of somatic alterations (See, Example 28).

She was restaged by whole body PET scan about 4 months after initiation of treatment which showed a good partial response with resolution of hypodensity along the superior posterior surface of the liver post therapy, compared to the CT prior to therapy. Decreased activity and resolution of mesenteric lymph nodes was observed. Resolution of subtle foci of FDG avid uptake along with surface of the liver was also observed. The only residual disease was identified at anterior surface of the liver below the diaphragm with stable activity. Her % cfDNA was repeated after an additional 4 months of therapy and compared to 8 months ago before therapy. All alterations had resolved post therapy as shown in her Guardant360 Tumor Response Map (FIG. 38) and summary of somatic alterations (FIG. 39).

In summary, the magnitude of observed with this combinational therapy is superior to conventional standard of treatment for her case (carboplatinum and Taxol) and proved to be safe and effective and requires further investigation. In conclusion, patient's initial response to the epigenetic therapy alone was unexpected and further addition of anticancer agent showed additional improvement that was unexpected because Crizotonib is not suggested to be effective alone, or approved for such indication.

Example 29—Case Study—Shukee—Treatment of Adenocarcinoma of Lung with Quercetin PG and Quercetin PG+Ceritinib This is a case study of a 69 year old male patient with history of stage 3B adenocarcinoma of the lung diagnosed after three months of undiagnosed cough, treated for TB/and cryptococcal infection which were found in his bronchoscopy. Malignancy was then identified after a CT guided biopsy of his lung mass, which revealed KRAs/ALK/EGFR negative tumor with contra lateral supraclavicular LN. After a month he underwent a brain MRI which revealed a brain mass 4 mm in size in the parietal lobe, with associated edema.

He was fatigued and complained of cough and was taking TB medications for a latent TB. He also had history of COPD/HTN/CAD/DM/and lipidosis.

At the clinic of Dr. Nezami, IV epigenetic therapies were started consisting of daily IV Quercetin PG as mainstay of treatment, and sodium phenyl butyrate as optional, immediately following the initial laboratory tests that confirmed the increased neuron specific enolase and CEA. He received 5 treatments and his laboratory tests were repeated which showed improved CEA (decreased from 68.6 to 55.9) and LDH (decreased from 323 to 306). He did not change his diet nor received any other therapies. His quality of life improved. His laboratory tests were repeated after 18 sessions of treatment and it showed substantial reduction in neuron specific enolase from 13.8 and 16.4 a week later to 9.4 measured about one month after treatment. His LDH stabilized at 304 and his ESR decreased from the 90s to 58. His VEGF was reported at 176 after one week of treatment and when repeated after one month of therapy had decreased to 60. About 10 days later, his brain MRI was repeated with fusion stereotactic resolution (MR spectrogram) and showed no change in the size of the tumor (stable). His FGF-2 was repeated after 18 treatments, and it decreased from 47 to 20. These results were achieved without any chemotherapy.

This is the first case report of a malignant adenocarcinoma metastasized to the brain successfully treated with epigenetic therapy.

His whole body PET CT performed about 2 months later showed that his left hilar mass decreased in size from 10.4 cm down to 9.1 cm. There were stable thoracic LNs in mediastinum. There were stable adrenal and pancreatic nodes. Pleural effusion was still present. There were no new lesions in the bones or liver.

Further, he continued with IV Quercetin PG in combination with Ceritinib about 4 months later, restarting again after a gap of two months. Upon his withholding of therapy his markers VEGF went up again to 197 measured after 2 weeks. After restarting the treatments, his CEA decreased from 48.7 measured at the time of restarting to 32.7 measured about 2 months later. During this time, his VEGF has decreased from 197 to 34.

He continued to improve clinically. His CXR showed the collapsed lung had opened again due to complete tumor necrosis. His restaging PET scan about 2 months earlier confirmed partial response to therapy by reduced size and activity of his lung mass and all extensive thoracic, mediastinal, supraclavicular and subcranial LNs. The left lung mass reduced from 6.7×10.4×9.3 cm to 5.8×7.7×7.5 cm, and the previous large right pleural effusion was completely resolved. Partial collapse of left lower lung was also resolved.

His CYFRA 21.1 also decreased significantly after the restarting the treatments, from 4.8 to 2.5.

In summary, this magnitude of response in an advanced case of lung cancer to the combinational therapies consisting of Ceritinib and Quercetin PG is very impressive and requires further investigations. In conclusion, patient's initial response to the epigenetic therapy alone was unexpected and further addition of anti-cancer agent showed additional improvement that was unexpected-because the targeted drug (Ceritinib) is not approved or suggested to be effective when administered alone, for such indication.

Example 30—Case Study—Caroline—Treatment of Breast Cancer with Quercetin PG+SPB and Quercetin PG+SPB+Herceptin This is a case study of a 44 year old female patient with history of right breast cancer with biopsy showing poorly differentiated infiltrating ductal carcinoma, Nottingham grade 3, with angio lymphatic invasion, with strong ER, PR and Her2/neu positivity on pathology; sized 2.8×2.1×1.2 cm; stage IIA with possible clavicular metastasis. Her MRI at the time of diagnosis reported "very large known aggressive cancer with two large feeding vessels plus two asymmetrical lymph nodes in the axilla."

She was referred to the clinic of Dr. Nezami after one round of chemotherapy (Carbiplatinum and taxotere) with severe side effects. She arrived for evaluation and treatment through targeted epigenetic therapy consisting of Quercetin PG as main stay of therapy, with butyrate. Her treatment was started about one month after her arrival. She had a prior diagnosis of MS and was on no specific treatment for that.

Her main complaint on arrival was fatigue and severe side effects from chemotherapy including developing parasites and severe immune suppression/leukopenia. Her initial laboratory test results on arrival indicated leukopenia with WBC of 1.500 mm$^3$, hemoglobin of 11 g/dl, and very low natural killer cell activity of 14.9 (viability 100 percent).

After three treatments, her CBC was repeated and showed improved WBC from 1.5 to 2.8 (Neutrophils increased from 15 to 35 percent), her natural killer cell activity was measured at 14.9 at the start of her treatment and improved to 29 about 3 weeks later, and to 45 another about 7 weeks later after the IV treatments.

Her tumor shrunk in size after uncompleted (three) rounds of neo adjuvant chemotherapy, along with Herceptin, although still palpable. The tumor was still present, with the size of the tumor reported to be 10×8 mm after completing three rounds of neo adjuvant chemotherapy, confirmed by ultrasound. The three rounds of chemotherapies consisted of Carboplatinum, docetaxel and Herceptin. However, the patient did not complete the recommended 12 cycles of Herceptin.

While on no conventional chemotherapy this time, she continued the epigenetic IV therapies along with Herceptin. Her tumor disappeared after two months of therapy at the clinic of Dr. Nezami. During this time she did not receive any chemotherapy. Her CT/PET scan was repeated, which showed no signs of activity or recurrent disease. She subsequently underwent a lumpectomy, after 40 IV sessions in 16 weeks, in average 2.5 sessions per week, which confirmed complete pathological response (no evidence of malignancy).

Meantime, her symptoms of MS including fatigue improved clinically and her functional capacity increased. While her prior brain MRI showed typical lesions, after five months of treatments her brain MRI was repeated, which showed decreased attenuation and size of white matter lesions, compared to MRI prior to the treatments. Meanwhile receiving IV therapies, she did not receive any conventional standard treatments for MS (such as interferon or steroids). She continued her treatment program at the clinic of Dr. Nezami on a bimonthly schedule for maintenance, for a year. At that time, she was in complete remission.

In summary, such response in a case of very aggressive breast cancer in which the patient was unable to tolerate chemotherapy showed that combining these modalities can increase the tolerability of treatments.

Of note, the tumor (which was palpable after application of Herceptin and neo adjuvant therapy) disappeared, confirmed by pathology after the addition of IV targeted epigenetic therapies to Herceptin, and complete remission achieved. At this stage, the patient did not (refused to) complete the neo adjuvant chemotherapy. However, finally her MS improved clinically and the MRI showed positive response obtained by the combination of Herceptin and epigenetic therapies.

In conclusion, patient's initial response to the epigenetic therapy alone was unexpected and further addition of anti-cancer agent showed additional improvement that was unexpected because the patient achieved complete pathological response prior to completing her course of standard therapy.

Example 31—Case Study—Edith—Treatment of Breast Cancer with Quercetin PG+Herceptin This is a case study of a patient with Metastatic Breast Cancer Stage four. The patient was an 83 year old woman with history of Left Breast cancer who had undergone lumpectomy, pathology confirming invasive ductal carcinoma, with score 9/9 grading and ER and Her2/Neu positive, with multiple recurrences, first one about 3 years later, with repeat lumpectomy followed by radiation therapy along with Herceptin and Femara, and a third recurrence about 7 years later and treated with Xeloda for few months and mastectomy about 2 years later. Her most recent imaging report prior to arriving at the clinic of Dr. Nezami was a PET scan about 1 year after the mastectomy indicating a positive patchy/multifocal FDG positivity in the left breast.

She had received numerous courses of different chemotherapies with minimal or no response before deciding to seek treatment at the clinic of Dr. Nezami. These included liposomal doxorubicin (Doxil), Gemzar (Gemcitabine), Herceptin (Trastuzumab), Taxol (Paclitaxel), Navelbine (Vinorelbine). Her last chemotherapy received was around the time of her mastectomy.

About 1 year after her mastectomy, she started treatment at the clinic of Dr. Nezami with epigenetic therapies involving intravenous Quercetin PG. She continued to stay on Herceptin received on every three week schedule. Treatment consisted of daily IV therapies. No chemotherapy was initiated during this time. No major lifestyle changes were undertaken. Her most recent laboratory tests before treatment at the clinic of Dr. Nezami indicated CEA of 8.1 and CA 27.29 of 21.8 and NK activity of 52.5. Circulating tumor cells (CTC) were checked by Cellsearch (Quest/Veridex Laboratories) before initiating therapy and reported as 24 CTC in 7.5 ml of blood, which correlates prognostically with an overall survival of less than 4.1 months.

Thereafter, patient was started on the treatment. She received daily IV treatments each lasting one and half hours. After 7 days, her laboratory tests were repeated. Her tumor markers CEA and CA 27.29 both decreased. CEA decreased from 8.1 to 7.5 and CA 27.29 from 21.9 to 19.5. Her CTC was also repeated after 3 weeks of this therapy and it was reported as zero. The tumor markers were again repeated after 25 more days of therapy and they still continued to decrease. CEA decreased to 6.5 and CA 27.29 decreased to 15.8.

The patient continued her treatments as ongoing monthly therapy with good clinical response, improved survival, and quality of life which included decreased pain, lower level of anxiety, better sleep, general coping and sense of wellbeing.

In summary, this case shows a synergistic clinical response in an otherwise refractory and advanced case of breast cancer, to combination of Quercetin PG and Xgeva, with safe and tolerable schedule. In conclusion, patient's initial response to the epigenetic therapy alone was unexpected and further addition of anti-cancer agent showed additional improvement that was unexpected because the patient was unresponsive to this anti-cancer agent alone.

Example 32—Case Study—Grace—Treatment of Breast Cancer with Quercetin PG and Quercetin PG+Herceptin This is a case study of a 62 year old female patient with history of right infiltrating ductal carcinoma of breast diagnosed in Asia. She was ER+, and PR, HER2/Neu negative based on her initial diagnosis. She further decided to opt in for only alternative therapies, which she received in Asia and the United States. She further had tumor progression with increased tumor size and decided to refer to the clinic of Dr. Nezami for therapies. Initially she underwent a staging PET scan which showed a right breast lesion but no further activity elsewhere. However, her laboratory tests showed positive CTC with positive ERBB2 and C-Myc.

At the start of his treatment, molecular detection of circulating tumor cells was performed as follows. In order to obtain circulating tumor cells from the patient's peripheral blood, large cells and cell-clusters as well as epithelial cells were isolated. A preparation of mononuclear cells (MNC)

served as a control cell fraction. mRNA was isolated from all fractions. Thereafter, the expression of tumor relevant genes was measured by quantitative real-time RT-PCR. A preparation of mononuclear cells (MNC) served as a control cell fraction.

The expression of the telomerase gene can be increased in most tumor types but not in normal tissue. An increased expression of telomerase gene may be indicative of the presence of tumor cells in the circulation. Expression of telomerase was not detected in the isolated cells. Overexpression of C-MYC indicates an increased proliferation of the isolated cells. An increased proliferation rate is a typical feature of tumor cells. The expression level of C-MYC was elevated. Overexpression of ERBB2 (HER2/NEU) is a trait of different types of cancer and may also be observed in breast cancer. Thus, the detection of ERBB2 overexpression may be indicative of the presence of circulating tumor cells. The expression of ERBB2 was elevated. The expression of ERBB2 was elevated. The detection of expression of cytokeratin (CK) 19 indicates the presence of epithelial cells and may thus be indicative for circulating tumor cells. There was no expression of CK19 detected. Thus, in the isolated tumor cell fraction, expression of ERBB2 and C-MYC was above threshold (>2.0). This finding was indicated of the likely presence of circulating tumor cells in the analyzed blood sample.

She was immediately started on IV epigenetic therapies which she received on daily basis for two weeks, consisting of Quercetin PG as mainstay of therapy CTC assay showed disappearance of telomerase, after two weeks of therapies on daily basis with IV epigenetic treatments.

Further she was referred for second biopsy of the satellite lesion on her right breast which became Er/PR and Her2 positive. She proceeded with mastectomy which showed 1.7 cm mass and positive sentinel LN plus DCIS, She agreed to receive Herceptin on every three week schedule, for 6 cycles.

She declined conventional chemotherapy and merely received epigenetic therapies with Quercetin PG, with positive results to this point, no sign of further recurrence or progressive disease and stays in complete remission. A reevaluation based on molecular detection of circulating tumor cell markers after about 2 months of treatment suggested that her tumor cell burden had decreased compared to earlier analyses.

The presence of circulatory tumor cells in her case, categorized her with stage four micrometastatic disease. To the Applicant's knowledge, there is no report of combinational therapy with an epigenetic modifier in conjunction with Herceptin and positive "destaging." To summarize this case, the application of epigenetic therapy was able to destage the patient into local disease which had responded to the combination of Herceptin and an epigenetic modifier.

In conclusion, patient's initial response to the epigenetic therapy alone was unexpected and further addition of anti-cancer agent showed additional improvement that was unexpected because the patient was able to accomplish remission prior to completion of her course of standard therapy.

Example 33—Case Study—Susan—Treatment of Breast Cancer with Quercetin PG+SPB; Quercetin PG+SPB+Herceptin This is a case study of a 54 year old post-menopausal female patient with history of invasive lobular carcinoma of the right breast, ER and PR positive, Her2 negative, diagnosed at stage four with liver and bone metastases, and treated with Femara and zometa, had partial mastectomy about 1 year later and a resection of a left renal clear cell adenocarcinoma (4.4 cm in size). She also had recurrence of metastatic breast cancer with metastasis in the liver. She also has had her appendix removed which showed mucinous adenocarcinoma.

About 3.5 years after her mastectomy, there was an increase in the size of her lymph nodes in the thorax from 2-3 mm to 8 mm in size.

She was referred by her physician in Pennsylvania to the clinic of Dr. Nezami. Upon her arrival, she was on hormonal blockade and refused chemotherapy. She underwent a whole body PET scan and initial laboratory evaluation which confirmed presence of metastatic lesions in all levels in thorax, axillary and cervical chains as well as thyroid with very high SUV activities of 20 and more. Her initial laboratory tests about 1 month later revealed increased CA 15.3 and CA 27.29 and CEA, as well as increased circulatory tumor cells (CTC) at 14.

She was immediately started on IV epigenetic therapies, consisting of Quercetin PG as mainstay of therapy, and sodium phenyl butyrate. She was re-evaluated after receiving daily IV therapies for two weeks. Her tumor markers all showed decreased values. Her CA 15.3 decreased from 34 to 28 (normal 25), her CEA decreased from 12.5 to 9.6 and then to 8.5 (normal 4.7), her LDH increased as a sign of tumor necrosis (257 from 170). Her CA 27.29 decreased from 43.6 to 34.7 (normalized). Her circulatory tumor cells decreased from 14 to 1 (one) after six treatments.

Figure 40:
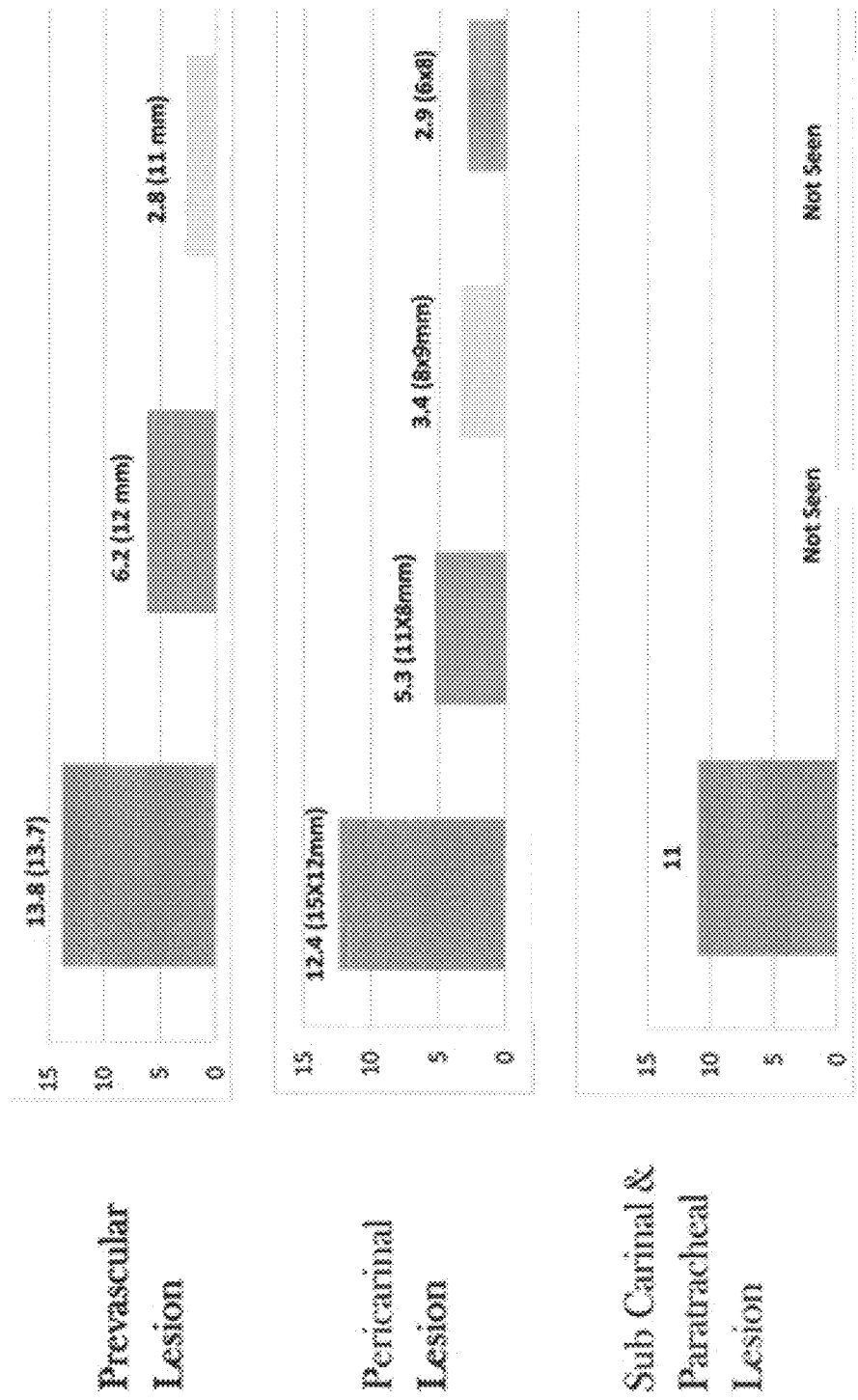
FIG. 40 shows an embodiment of a graph of tumor metabolic activity on PetScan (SUV) in a patient with stage IV breast cancer over an average treatment time of about 85 days (See, Example 33).

Her PET scan about 3 months later confirmed positive response to interval therapy with both decreased size and activity in all thoracic lesions. No new lesion was identified. Abnormal hypermetabolism seen in her prior scan about 4 months ago in multiple thoracic lymph nodes (perivascular, mediastinal, paratracheal, precarinal, hilar) had improved and the nodes appeared smaller (11×8 from 15×12). The SUV activities decreased from 13.8 to 6.2 (FIG. 40) and from 12.4 to 5.3 (FIG. 40).

She continued the maintenance therapies, consisting of Herceptin received every three weeks, as well as epigenetic therapies. Her laboratory test results indicated that her CTC remained at 1 measured around the time of her PET scan. Her CA 15-3 and 27.29 remained at normal level (30 and 38). Her FGF-2 decreased from 10.5 about 1 month later to 7.3 about 2 months later and further decreased to 4.8 (normal range) about 3 months later. This is a marker related to cancer stem cell activity and EMT transition.

Her re staging PET scan confirmed significant positive response to the interval therapy suggested by reduction in size and activity of all neck, thoracic and abdominal lesions. All her tumor activities decreased 70-80 percent and 90 percent to normal physiologic activity.

Figure 41:
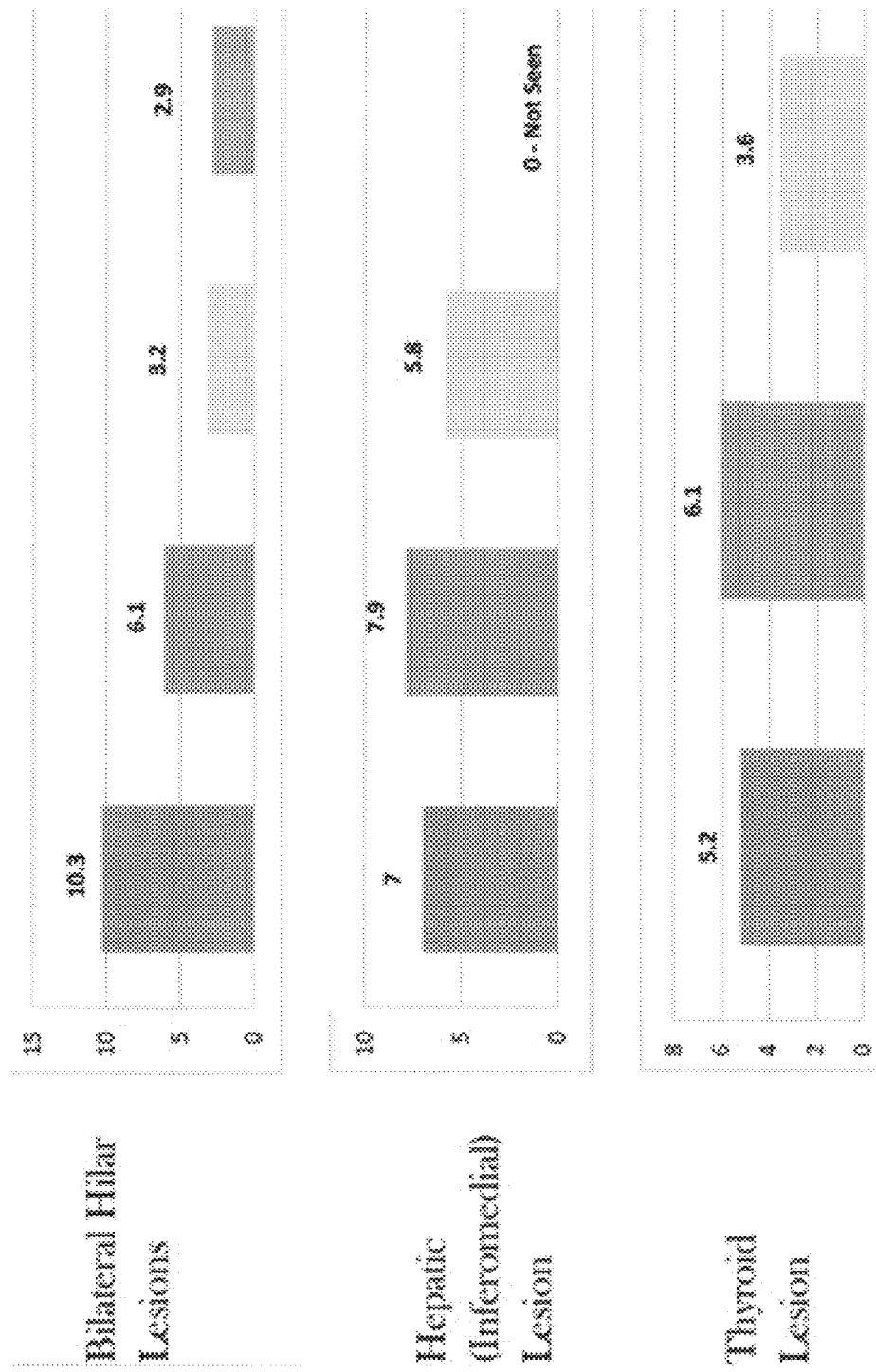
FIG. 41 shows an embodiment of a graph of tumor metabolic activity on PetScan (SUV) in a patient with stage four IV breast cancer over an average treatment time of about 85 days (See, Example 33).

Metabolic activity of such lesions at the thoracic (Hilar, pericardial and perivascular) lymph nodes decreased from 13.8 to 6.2 to 2.8 (FIG. 40) and 12.4 to 5.3 to 3.4 (FIG. 40), and 10.3 to 6.1 to 3.2 (FIG. 41). The bony lesion at L4 demonstrated no increased activity/physiologic activity. This response was obtained without receiving any chemotherapy. The duration of therapy for her up to this point was about 85 days.

Further she was followed on maintenance therapies and her restaging scan was repeated about 3 months later with decreased activity and size in all lesions again. The Hepatic lesion, which on prior exam showed SUV activity of 5.8, was not seen (FIG. 41). The Pericarinal lesion and hilar lesions in the thorax also decreased in activity to 2.9 from 3.4 (FIG. 40) and 3.2 (FIG. 41), respectively. In summary, the above unexpected clinical response in such an advanced case of metastatic breast cancer suggests synergistic effects with applying the combinational therapies of epigenetic modifiers in combination with Herceptin.

In conclusion, patient's initial response to the epigenetic therapy alone was unexpected and further addition of anti-cancer agent showed additional improvement that was unexpected because such anticancer therapy was not approved or suggested to be effective for her type of cancer.

Example 34—Case Study—Traci—Treatment of Breast Cancer with Quercetin PG+SPB+Herceptin This is a case study of a 49 year old female patient with history of stage four ER positive/Her2/Neu positive, BRCA-1 negative poorly differentiated infiltrating left breast ductal carcinoma per pathology who underwent lumpectomy and axillary lymph node dissection with one positive lymph node, and received adjuvant chemotherapy the same year. She experienced tumor recurrence in liver about 4 years later which was treated unsuccessfully with multiple chemotherapy courses for about 4 years (15 chemotherapy agents used, consisting of Xeloda, carboplatinum, bevacizumab, avastin, doxorubicin, etoposide, faslodex, arimidex, gemzar, Herceptin, tamoxifen, taxotere, tykerb, Ixepmpera, and xoladex). Despite treatment, during the course of chemotherapy she experienced progression of the tumor in liver and abdominal cavity. Her chemotherapy treatment was claimed to be unsuccessful and therefore was eventually stopped.

She was referred by her physician after 4 years of treatment to the clinic of Dr. Nezami for Complementary and Integrative cancer treatments. Initially the patient presented with jaundice and extensive ascites (documented in her abdominal CT scan before treatment) in abdomen and pelvis, along with multiple (too numerous to count) metastatic lesions in the liver and abdominal lymph nodes. Her abdominal CT also revealed marked progression of disease and increasing size of subcarinal and left supraclavicular adenopathies documented in several CT scans. The physical exam confirmed presence of these findings including an extensive supraclavicular lymphadenopathy >10 cm in diameter.

The patient was started on intravenous targeted epigenetic therapy consisting of Quercetin PG and SPB almost immediately. Her Natural killer cell activity along with her tumor markers, LDH and liver enzymes were measured before and during the course of treatment. She had failed all hormonal therapy/targeted therapies/chemotherapy options available through her oncologist. She remained on Herceptin and Arimidex, which she had been on for many years, while beginning daily IV epigenetic therapy at the clinic of Dr. Nezami. She did not change her diet or other life style factors during her course of therapy.

Her abdominal CT scan was repeated about 3 months later which revealed marked reduction in abdominal and pelvic ascites, along with reduced size of the lymph nodes both in abdominal and supraclavicular regions. The liver metastatic lesions were reduced in size as well. On physical exam there was no mass palpable at previously measured area of lymphadenopathy (sized >10 cm) in the supraclavicular space.

Her CRP decreased from 20 to 14, her serum copper decreased from 221 to 211. As measured between 15 and 17 months after initiation of treatment, all liver enzyme decreased including Bilirubin (from 3.3 to 2.2), AST (decreased from 213 to 40), ALT (normalized to 42 from 296), LDH normalized, GGT decreased from 916 to 247 and Alkaline phosphatase decreased from 996 to 468. Her Natural killer cell activity increased 30 percent.

She continued her treatment program with Dr. Nezami for 12 months, with improved response and clinical condition, exceeded the life expectancy associated with her presentation to us with an extremely advanced stage of cancer. Her last treatment at the clinic of Dr. Nezami was about 11 months after initiation of treatment.

In summary, this case is indicative of superior clinical outcome based on combination of epigenetic therapies with Herceptin, compared to chemotherapy and Herceptin alone. The superior results are defined by improved survival, and tolerability of such regimen. In conclusion, patient's initial response to the epigenetic therapy alone was unexpected and further addition of anti-cancer agent showed additional improvement that was unexpected because the patient was unresponsive to the anti-cancer agent alone.

Example 35—Case Study—Vu—Treatment of Colorectal Cancer with Quercetin PG+SPB+Trametinib This is a case study of a 61 year old male patient with history of stage four colorectal cancer after several rounds of chemotherapy regimens, both cytotoxic and targeted therapies, including Folinic Acid, Fluorouracil and oxiplatinum (FOLFOX), Folinic Acid, Fluorouracil and Irinotecan (FOLFIRI) and bevacizumab (Avastin), Erbitux (Cetuximab), Stivarga (Ragorafenib), radioembolization (Yttrium 90) radiation to the liver, prior to arriving at the clinic of Dr. Nezami for evaluation and treatment.

He was referred to hospice by his oncologist, as well as an oncologist at the clinic of Dr. Nezami. Upon his arrival, he was jaundiced and was suffering from pain and malignant ascites.

Laboratory tests were performed which showed significant increased tumor markers and LDH. He was immediately started on IV epigenetic therapies consisting of intravenous Quercetin PG as the mainstay of therapy combined with sodium phenyl butyrate and targeted therapies, in his case, the choice of drug was Trametinib (Mekinist), which he received on daily basis. The rationale on choosing this drug was not based on prevalence of KRAS positive disease in colorectal cancer (his tumor was KRAS wild), rather it was based on clinical experience in combination of such therapies with extra-ordinary results, in similar patients, in the Applicant's practice.

He immediately felt better and his quality of life improved. His tumor markers repeated after 5 treatments (in 7 days), and it showed a marked reduction in his LDH from 416 to 327, and his CEA decreased from 384 down to 288.

He maintained therapies without experiencing any negative side effects. Further, to Applicant's knowledge he followed with the treatment at his home.

In summary, such dramatic results are not expected from trametinib by itself, and are indicative of the value of combination therapy in providing a safe and effective option for similar patients who have failed other potential therapies. In conclusion, patient's initial response to the epigenetic therapy alone was unexpected and further addition of anti-cancer agent showed additional improvement that was unexpected as this targeted drug (Trametinib) is not approved or suggested to have any clinical benefit when administered alone for this type of cancer.

Example 36—Case Study—Vicki—Treatment of Rectal Cancer with Quercetin PG+Trametinib This is a case study of a 64 year old female patient with history of rectal cancer diagnosed after about a year of rectal bleeding (which was un-noticed), until her colonoscopy revealed a tumor in her rectum was suspected to be T3, with no involvement of LNs. However, abdominal and pelvic CT scan confirmed the presence of multiple large liver lesions in both lobes as well as pulmonary nodules, making the patient stage four. Further, chemotherapy (FOLFOX regimen) was offered but patient refused.

She was referred to the clinic of Dr. Nezami clinic for evaluation and treatments about 1 month after her diagnosis. Upon her arrival she was having rectal bleeding and some fatigue but otherwise asymptomatic.

Upon her arrival she underwent a restaging PET scan which showed multiple masses (5-6 cm) with highest SUV activity of 9.1 in liver, large rectal mass (about 5 cm in size) with SUV activity of 19.8 in rectum and many other metastatic lesions in lungs.

She was referred for proton radiation therapy to the liver. Proton therapy was considered for the most enlarged masses in the liver, after systemic therapy, as she was referred to Scripps proton center in San Diego. However, it was concluded by radiation oncologist, that due to extensive metastatic disease in the liver she would not qualify for such therapy.

Prior to therapy at the clinic of Dr. Nezami, laboratory tests were performed. Her tumor markers were elevated, and circulatory tumor cells (CTC) showed positive EGFR at T790M, but no KRAS. CTC was positive for ERBB2 as well. Her CTC was positive for DNA methyl transferase and Histone deacetylase (DNMT and HDAC).

Patient was started on IV epigenetic therapies consisting of Quercetin PG, which she received on daily basis in combination with Mekinist at 1 mg per day.

As soon as the treatments started, patient started to feel better, her rectal bleeding stopped, and her tumor markers decreased. CA 19.9 decreased to 2069 from 2670 in a week. Her LDH has also decreased from 318 to 264 after about 3 weeks of treatment. Her CEA continued to decrease to 839 from 933. Her CA 19.9 as well continued to decrease to 2069 from 2880.

Her CTC was repeated after 4 weeks of daily IV epigenetic therapies. The CTC completely disappeared with therapies. Her laboratory test results continue to improve with CEA decreased to 583 and CA 19.9 decreased to 987, ALK-P decreased to 130. She was restaged with a whole body PET scan. This showed significant improvement in her all metastatic as well as original tumor. Her liver masses shrunk in size and metabolic activities. (SUV activity decreased from 9.1 to 5.9 in highest active lesion). The pulmonary lesions also decreased in size and activity (size from 1.5 cm to 1.0 cm) and SUV activity from 2.7 to 0.9. Her rectal mass decreased in metabolic activity from 19.8 down to 5.4 and size from 5 cm to 1 cm.

In conclusion, the current literature does not support any expected clinical response from Trametinib in colorectal cancer, regardless of mutational status, as a single agent. To the Applicant's knowledge this is the first response reported in an advanced setting in response to combination of epigenetic therapies with Trametinib.

The patient is continuing her treatments at the clinic of Dr. Nezami with very good clinical outcome. In conclusion, patient's initial response to the epigenetic therapy alone was unexpected and further addition of anti-cancer agent showed additional improvement that was unexpected because the targeted therapy she received was not approved or suggested to be effective if used alone, for this type of cancer.

Example 37—Case Study—Steven P—Treatment of Rectal Cancer with Quercetin PG+SPB+Trametinib This is a case study of a 49 year old male patient with history of advanced rectal cancer diagnosed at stage four after a long period of episodic rectal bleedings, which were ignored by him. His tumor was already metastasized based on his scans to his liver and lung, and for which he declined chemo and radiation and proceeded with variety of alternative therapies which he received in Germany, including vaccines, vitamin drips, hyperthermia, etc., but had progressed based on an additional scan performed about 3 months alter, with images showing numerous lesions in his liver which had increased in size, further he decided to accept standard treatments including radiation and chemotherapy with capecitabine (Xeloda) which he regretted further as it caused significant morbidity. Palliative chemo and radiation was provided about 1 month after the additional can consisting of Xeloda and local radiation to rectum. This was able to reduce the level of pain and improve his symptoms, but the tumor continued to grow and he continued to have increased metastasis to his lungs and growth in liver and rectum, causing bleeding and severe cough. As a result, he opted again for experimental therapies which he had received starting a month later in Hawaii, consisting of Poly MVA, GcMAF.

He admitted that his state of disease had been progressing as he could not talk without coughing and his level of energy had decreased.

About 6 months after starting experimental therapies, he arrived at the clinic of Dr. Nezami. Initial evaluation showed increased tumor markers, as well as positive liquid biopsy (% cfDNA) consisting of KRAS/BRAF and APC, with mutation allele fraction (markers) very elevated.

He was immediately started on IV epigenetic therapies consisting of Quercetin PG and sodium phenyl butyrate, which he received on daily basis for two weeks after which his laboratory tests were repeated. The laboratory tests indicated decreased LDH from 1218 to 659 measured about 2 weeks later, as well as liver enzymes, for example ALK-P decreased from 204 to 164. The patient was being administered a combination of Mekinist based on his % cfDNA with epigenetic therapy consisting of Quercetin PG intravenously for about a month at this point. His TGF decreased from 35954 prior to therapy to 23119 after 18 treatments and further to 20934 about 1 month later. His cough completely stopped after 4 weeks of therapy as well as his rectal bleeding around the same time. His LDH further decreased to 504 and his hemoglobin improved. He is continuing the treatments at the clinic of Dr. Nezami with no measurable toxicity. His plasma interleukin-8 as a marker for angiogenesis decreased as he continued the combinational therapies. IL-8 decreased from 278 pre-therapy to 106 after about 1 week of therapy and further decreased to 100, 86, and 74 (normal=<34) after an additional one, two and three weeks of therapy, respectively. His ALK decreased from 204 to 190 to 132. His AST decreased from 143 to 48. His ALT decreased from 73 to 19.

Figure 42:
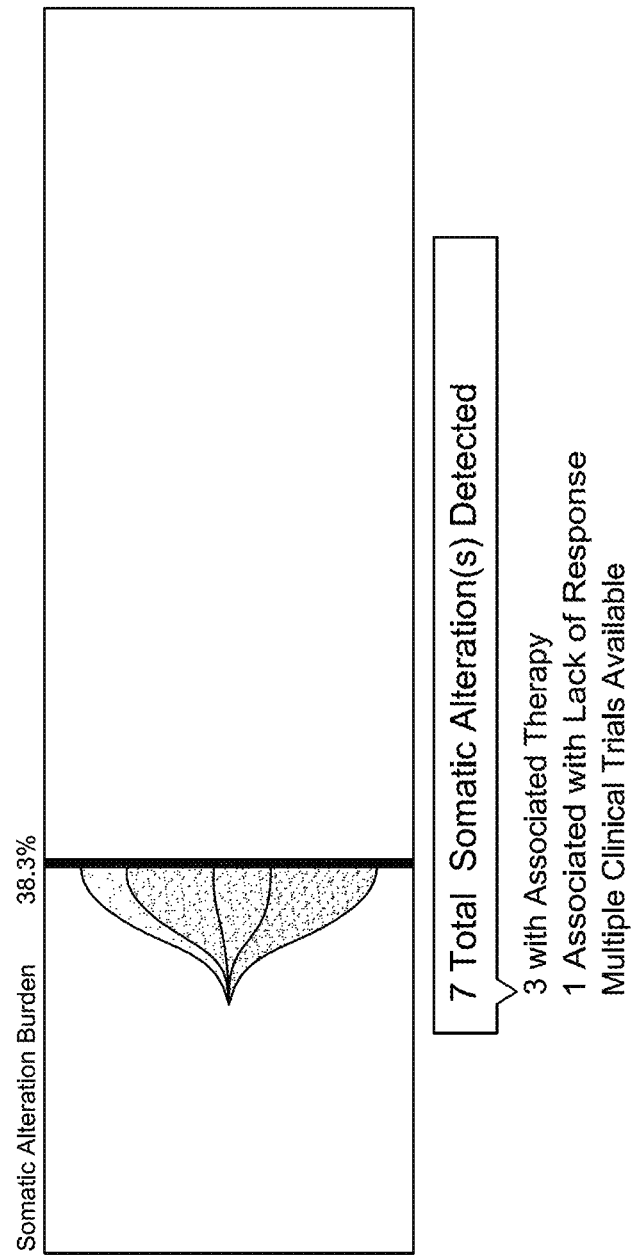
FIG. 42 shows an embodiment of a Guardant360 Tumor Response Map (See, Example 37).
Figure 44:
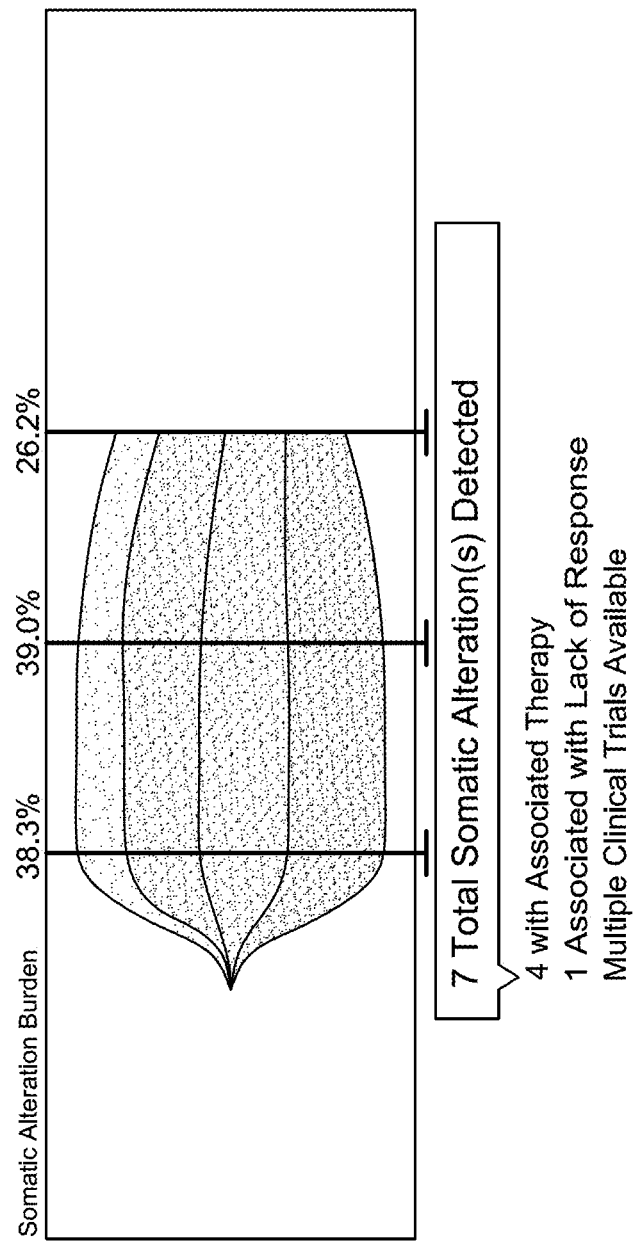
FIG. 44 shows an embodiment of a Guardant360 Tumor Response Map (See, Example 37).
Figure 45:
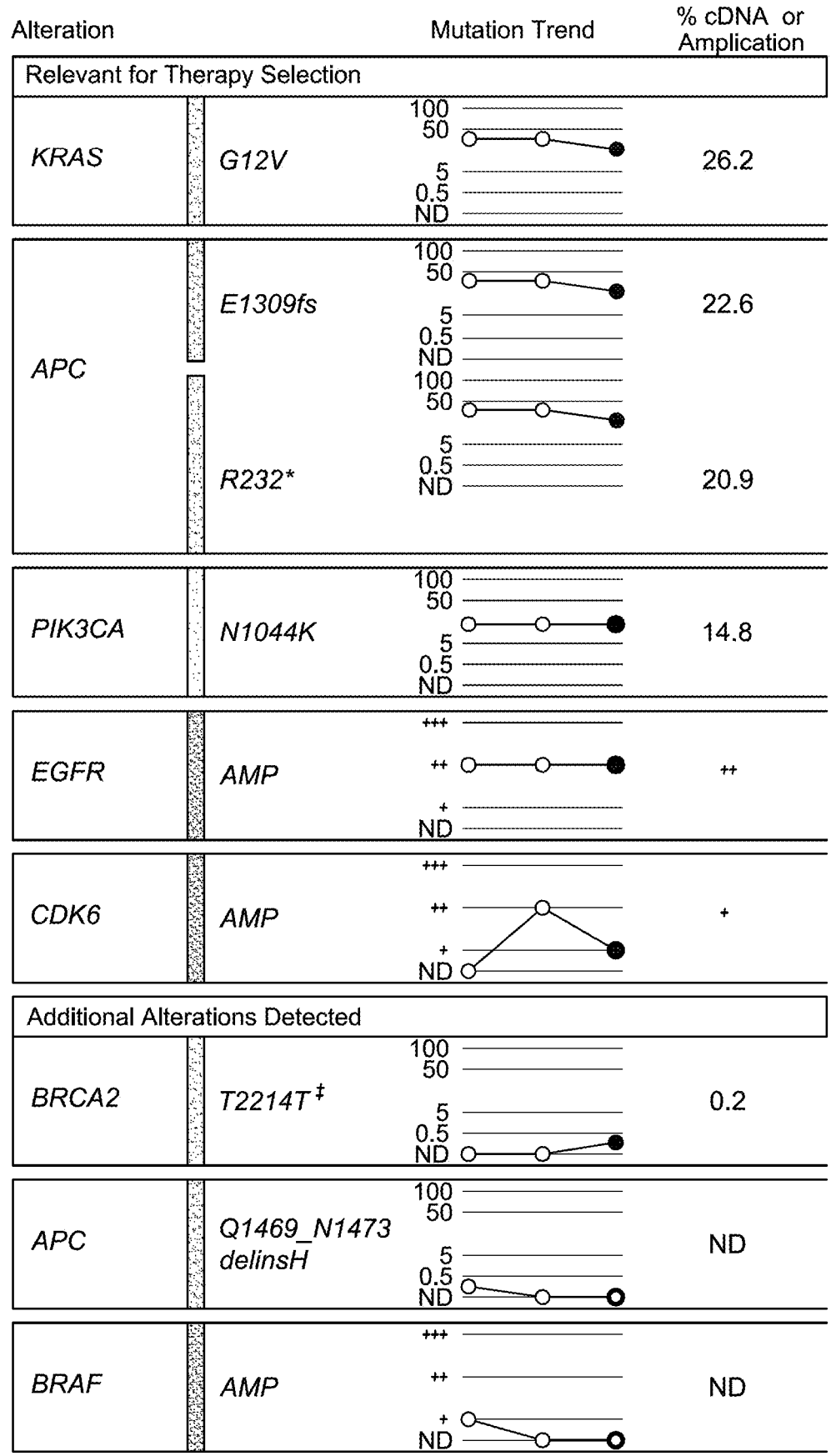
FIG. 45 shows an embodiment of a summary of somatic alterations (See, Example 37).

He was restaged about 6 weeks later with whole body PET scan which showed significant positive metabolic response, with reduction in all lesions metabolic activities, for example, rectal lesion reduced in activity from 21.6 to 11.0. His pulmonary lesions all had positive response to therapy with reduced SUV activity of 12.7 down to 3.8 in the largest lesion in right upper node. His liver lesions as well had reduced SUV activity from 17.5 top 10.8 in superior right hepatic lobe, largely had necrosis. FIG. 42 and FIG. 43 respectively show his Guardant360 Tumor Response Map and a summary of somatic alterations prior to therapy, and FIG. 44 and FIG. 45 respectively show his Guardant360 Tumor Response Map and a summary of somatic alterations after therapy.

Given his clinical state of health pre-treatment, his response to the combination therapy was marked and he was now able to talk without coughing and his rectal bleeding had stopped. His drastic response based on his laboratory tests was also noticeable. He is continuing his treatments at the clinic of Dr. Nezami. To the Applicant's knowledge this is the first case study reported on combinational therapy consisting of trametinib and an epigenetic modifier with proven clinical benefit. In conclusion, patient's initial response to the epigenetic therapy alone was unexpected and further addition of anti-cancer agent showed additional improvement that was unexpected because the targeted therapy he received was not approved or suggested to be effective for this type of cancer.

Example 38—Case Study—Bertha—Treatment of Pancreatic Cancer with Quercetin PG+SPB+Trametinib This is a case study of a 65 year old female patient with history of stage four pancreatic cancer with biopsy of a large 14 cm mass at the head of the pancreas, along with metastatic deposits in the liver extensive disease in pelvis as well as abdominal peritoneal carcinomatosis who presented to the clinic of Dr. Nezami for evaluation and treatment.

The patient was complaining of loss of appetite, diarrhea and weight loss. The initial evaluation showed negative circulatory tumor cells, but positive circulatory DNA for ERBB2. The tumor markers were elevated both CA 19.9 (1054) and CEA (11.9).

She was immediately stared on combination therapy consisting of intravenous Quercetin PG and sodium phenyl butyrate that she received on daily basis. Other treatments included oral targeted therapies including trametinib (Mekinist).

After five days, her symptoms relieved and she started to eat. ECOG score improved and she was able to gain weight and function normally. After two weeks, her laboratory tests were repeated and showed a reduction of 20 percent in her tumor marker. CA 19.9 decreased to 762.2 from 2000 and 1054 after 2 weeks of treatment. After about 2 months of treatment, her CA 19.9 had decreased to 348 from 1054 and CEA to 8.9 from 11.9. Her circulatory DNA was repeated and it showed complete resolution of the ERBB2 alteration, i.e., there was no detectable % cfDNA (FIG. 46).

In summary, this rapid response can be a preliminary finding that could potentially correlate with a better outcome. There was a clear correlation between her survival and with her lab result. In conclusion, patient's initial response to the epigenetic therapy alone was unexpected and further addition of anti-cancer agent showed additional improvement that was unexpected because the targeted therapy she received was not approved or suggested to be effective for her type of cancer.

Example 39—Case Study—Maria—Treatment of Rectal Cancer with Quercetin PG+Trametinib This is a case study of a 62 year old female patient with history of rectal cancer diagnosed after episodes of rectal bleeding. About 2 months later MRI suggested a large mass in the rectum along with extension to pelvis and some spots in the liver (Right hepatic lobe 3 cm and second one 2.4 cm confirmed by the CT), colonoscopy showed necrotic mass with more than 50 percent circumferential involvement (T4).

Unfortunately the pathology only showed the adenocarcinoma, initially and therefore she was started on FOLFIRI regimen, which she did not respond to at all, for 2 cycles, with significant side effects including severe vomiting, weight loss and lost her QOL.

Multiple lesions were subsequently identified as new lesions in liver. She further underwent a second biopsy from her liver lesions about 1 month later, which confirmed the mixture of neuroendocrine and adenocarcinoma with ratio of 70 to 30 percent. Therefore, the chemotherapy was not continued. She was seen at proton center and radiation oncologist recommended to start her on Y90 and proton therapy on her liver and rectal mass, respectively. She complied with such regimen which was completed 3 months later. Nevertheless, her scans confirmed the rapid progression of her disease. She was referred by the proton department to clinic of Dr. Nezami for evaluation and treatment. During this time, she had several episodes of hospitalizations due to obstructions (after chemotherapy), and ended up with a diverting colostomy about 2 months earlier. She has also seen her oncologist who offered hospice to her. She had refused such option.

She was very wasted, had significant weight loss, due to loss of appetite and was in severe pain, despite that she was receiving high dose morphine.

She was immediately started on IV epigenetic therapies in combination with Trametinib, after initial evaluation which revealed significantly elevated tumor markers, LDH, and CRP.

Prior to therapy, her tumor molecular profiling showed positive mutations in MLH1, MSH2, and MSH6 and PMS2. This is a very interesting finding as it correlates with the nature of epimutations involved with this type of tumor, and the correlation with her response to the epigenetic therapy.

After therapy for about 2 months, her laboratory tests showed a marked reduction of angiogenesis. Her platelets decreased to normal (429 to 309), her LDH decreased from 725 to 473, CRP decreased from 84 to 50. Her repeat laboratory tests about 1 week later showed reduction of LDH to 434, and her chromogranin A decreased from 76 to 67 and further to 56. This is an important marker as it correlates with response and improved survival. She was under care at the clinic of Dr. Nezami for about 5 weeks. Her % cfDNA stabilized after a month of therapy.

Unfortunately patient suffered from another episode of obstruction at the ostomy site and attempts to convince surgeons to perform a diversion was unsuccessful. Patient opted for palliative care after a month of care at the clinic of Dr. Nezami.

In conclusion, the initial response to therapy evident in patient's markers were unexpected, considering the advanced stage of her disease and lack of response to all other potential therapies. In conclusion, patient's initial response to the epigenetic therapy alone was unexpected and further addition of anti-cancer agent showed additional improvement that was unexpected because the targeted therapy she received was not approved or suggested to be effective for her type of cancer Example 40—Case Study—Patricia—Treatment of Cervical Carcinoma with Quercetin PG+SPB+Trametinib This is a case study of a 50 year old female patient with history of cervical squamous cell carcinoma diagnosed after many alternative therapies without success, had refused radiation and chemotherapy, was at hospice care/condition when she was referred to the clinic of Dr. Nezami for evaluation.

Prior to arriving at the clinic of Dr. Nezami, her last CT performed about 2 years after her initial diagnosis showed significant worsening of her disease compared to her prior scan about 3 months earlier with extension of her pelvic mass about 7 cm into her gluteal area, partial obstruction of her colon, bilateral hydronephrosis, and with extensive involvement of pelvic structures, including rectum and vagina, with rectovaginal fistula. She was suffering from fatigue, cramps, constipation, diarrhea, and weight loss.

She had an advanced disease with involvement of her ureters bilaterally and bladder fistula, she had stents that had been misplaced, malignant ascites, extensive retroperitoneal lymphadenopathies, and cachexia.

She was evaluated through tumor markers, circulating tumor cells (% cfDNA) and circulatory tumor cells (CTC).

At the start of her treatment, molecular detection of circulating tumor cells was performed as follows. In order to obtain circulating tumor cells from the patient's peripheral blood, large cells and cell-clusters as well as epithelial cells were isolated. A preparation of mononuclear cells (MNC) served as a control cell fraction. mRNA was isolated from all fractions. Thereafter, the expression of tumor relevant genes was measured by quantitative real-time RT-PCR. A preparation of mononuclear cells (MNC) served as a control cell fraction.

The expression of the telomerase gene can be increased in most tumor types but not in normal tissue. An increased expression of telomerase gene may be indicative of the presence of tumor cells in the circulation. The expression of telomerase was slightly elevated in the isolated cells. Overexpression of C-MYC indicates an increased proliferation of the isolated cells. An increased proliferation rate is a typical feature of tumor cells. The expression level of C-MYC was not elevated. Overexpression of ERBB2 (HER2/NEU) is a trait of different types of cancer and may also be observed in breast cancer. Thus, the detection of ERBB2 overexpression may be indicative of the presence of circulating tumor cells. The expression of ERBB2 was not elevated. The detection of expression of cytokeratin (CK) 19 indicates the presence of epithelial cells and may thus be indicative for circulating tumor cells. There was no expression of CK19 detected. Thus, in the isolated tumor cell fraction, expression of telomerase was slightly above threshold (>2.0). This finding was indicated of the likely presence of circulating tumor cells in the analyzed blood sample. Since telomerase was only slightly elevated and all other detection markers were negative, the tumor cell burden in the blood was likely low.

All her markers were elevated (CA 15.3, CA 125, CEA, HE4, and LDH at 34, 40, 6.9, 341, and 228, respectively). Her % cfDNA showed positive ERBB2 and APC alterations. Her CTC was positive for telomerase.

She was immediately started on IV epigenetic therapies consisting of intravenous Quercetin PG consisting as mainstay of treatments, combined with sodium phenyl butyrate. Further therapy was combined with targeted therapies, in this case, Trametinib (Mekinist).

Her laboratory tests were then repeated which showed positive response to therapy. She felt much better after first round of treatments in two weeks, the pain had resolved and she had a better QOL and stamina. Her LDH decreased from 508 to 255. Post therapy, her % cfDNA also showed response with decreased MAF of 0.2 from 0.4 percent (FIG. 47), and expression of telomerase, C-MYC, ERBB2 and CK19 were not detected after about 4 weeks of treatment.

She was restaged with a whole body PET/CT about 2.5 months after therapy, which showed complete resolution of retroperitoneal LNs, pelvic and abdominal ascites, pleural effusions, decreased inguinal LNs, as well as resolution of mesenteric edema and right hydronephrosis. Kidneys appeared normal this time, with resolution of perinephric inflammation and cortical atrophy.

In summary, such a response in an advanced case of cervical cancer is completely unexpected and is very impressive. She is continuing her care at the clinic of Dr. Nezami and so far has exceeded her life expectancy. In conclusion, patient's initial response to the epigenetic therapy alone was unexpected and further addition of anti-cancer agent showed additional improvement that was unexpected because the targeted therapy she received was not approved or suggested to be effective for her type of cancer alone.

Example 41—Case Study—Priscella—Treatment of Hepatic Cancer with Quercetin PG+SPB+Trametinib This is a case study of a 40 year old female patient was initially diagnosed while living in Mexico during routine physical exam, when a ultrasound showed a mass in her liver, identified as hepatic cancer. The patient had liver resection and tolerated the procedure well. Path report indicated tumor was negative ACE, negative CA125, negative CA19-9, negative CD45, positive CK7, negative CK20, negative HM1B-45, positive chromogranin, positive CD 56, negative Hepar, negative glypican, negative TTF-1, positive calcitonin, consistent with neuroendocrine malignant neoplasm (carcinoid tumor).

A year later her disease recurred with a mass in liver. The patient was experiencing abdominal distention and discomfort with lower extremity edema. A chemo embolization of the liver mass/lesion was performed. About 1 year later patient went on to receive Octreotide injections with no response. About 2 years later patient began to experience severe headaches and MRI of brain indicated two lesions, identified as metastatic disease, resected about 1 month later. Patient did not receive any radiation therapy. Patient further completed three cycles of Temodar and capecitabine (administered prior to administration of the epigenetic treatments disclosed herein). Results from CT scan about 5 months later performed after chemotherapy indicated progression of her disease. Therefore, all chemotherapies were stopped and patient was referred to palliative care/hospice.

Upon her arrival to the clinic of Dr. Nezami, she was in pain and did not have appetite. As she was evaluated, she had a poor function and ECOG score, her laboratory tests showed significantly elevated tumor markers—LDH was at 1603, and HE4, CA 125, TGF, chromogranin A were all elevated with signs of liver failure (increased INR and ALK-p of 294, increased liver enzymes). Her liquid biopsy showed positive circulating DNA (% cfDNA) altered for PI3k (at 16.4 percent), APC, ESR1, TP53, c-Kit, and her circulating tumor cells (CTC) was positive for PDGFR-beta. C-Kit and PDGFR-beta are growth factor receptor which may be overexpressed in different kinds of tumors, especially neuroendocrine tumors, and elevated expressions are likely to be indicative of the presence of circulating tumor cells. Her CTC chromogranin was negative.

Her CT scan prior to therapy showed:

1. Partial hepatectomy with marked enlargement of the residual liver which is replaced by several large masses. Largest liver mass measured 16.4×9.3 cm, with extensive tumor throughout remaining liver as well as pora hepatis region with moderate scattered abdominal ascites, and tumor thrombus partially occluding the portal vein. There was extensive confluent lymphadenopathy in the region of the pancreatic head, porta hepatis and celiac region of the upper abdomen.

2. Several pulmonary lesions consistent with metastatic disease. Largest nodes involved the lower lobes—5.4×4.8 cm on the left and 4.8×3.7 cm of the right. There was extensive mediastinal lymphadenopathy.

3. Prominent small bowel without definite obstruction, and moderate ascites.

She was started on IV epigenetic therapies consisting of intravenous Quercetin PG as mainstay of therapy in conjunction with sodium phenyl butyrate and targeted therapy, in this case Trametinib (Mekinist) in a sequential manner. After three weeks of targeted therapies by above combination, the patient was reassessed.

The restaging scan showed stable disease, compared that with her prior scan 1 month earlier. The tumor was stabilized in size, pulmonary metastatic disease had improved along with the porta hepatis disease. Tumor involving pancreas which was seen in prior scan was not visible post therapy and had resolved.

Figure 48:
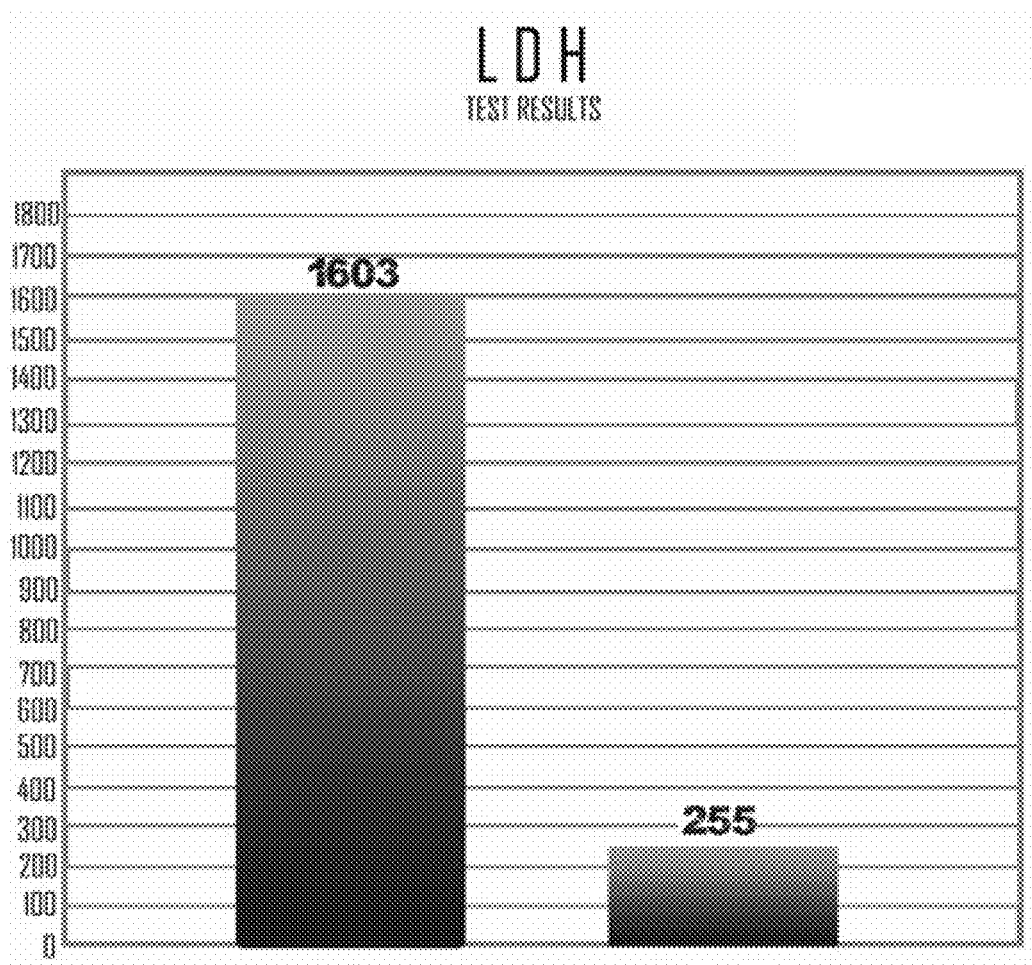
FIG. 48 shows an embodiment of a graph of LDH levels before and after treatment (See, Example 41).

Her tumor markers had improved post therapy: LDH (decreased to 255 from 1603 (FIG. 48)), IL-8 (50 from 98), and HE4 (163 from 198). Her amylase decreased to 800 from 2000. Her liver enzymes improved (AST/ALT normalized) and her INR of 1.6 decreased to 1.2 post therapy.

Her circulatory tumor cells showed positive response to therapy with complete disappearance and resolution of CTC. After therapy, her CTCs were no longer positive for PDGFR-beta.

In summary, the patient showed unexpected improved quality of life and passed her expected survival. To the Applicant's knowledge this result was unexpected and surprising as there is no published evidence on any therapeutic intervention to achieve such response with application of trametinib with epigenetic therapy. In conclusion, patient's initial response to the epigenetic therapy alone was unexpected and further addition of anti-cancer agent showed additional improvement that was unexpected because the-targeted therapy she received was not approved or suggested to be effective for her type of cancer.

Example 42—Cell Lines and Maintenance, Preparation of Modulators, MiCK® Assay and Data Analysis Non-limiting examples of cells include AU-565 (breast carcinoma), MCF-7 (breast adenocarcinoma); MDA-MB-468 (breast adenocarcinoma), NCI-H23 (lung adenocarcinoma), NCI-H460 (non-small cell lung carcinoma), NCI-H1299 (non-small cell lung carcinoma), BxPC-3 (pancreatic adenocarcinoma), MIA PaCa-2 (pancreatic adenocarcinoma), Malme-3M (malignant melanoma), A-172 (glioblastoma), MES-SA (uterine sarcoma). These cell lines are already resistant to one or more anti-cancer agents.

The cells lines are grown and maintained in their specific cell culture medium without phenol red, supplemented with 10% FBS, 100 U/mL penicillin and 100 µg/mL streptomycin in humidified air with 5% C02 at 37° C. Before use, exponentially growing cells are harvested, washed with pre-warmed medium and then re-suspended in complete medium.

A stock solution of quercetin is prepared in 20% DMSO at a concentration of 500 µM and then diluted to 100 µM in the culture medium. The final concentration of DMSO in the well is 1% or less. A slight yellow color is encountered but the color is not considered significant in the assay. Sodium phenyl butyrate is dissolved in RPMI at a concentration of 20 µM without an interfering color development. Epigallocatechin-3-gallate is dissolved in RPMI at a concentration of 10 µg/mL.

The MicroCulture® Kinetic (MiCK®) assay is used to detect and quantitate apoptotic cell death in a population of cells. The cells of interest are exposed to the drug(s) of interest in the wells of a 384 well spectrophotometric plate with RPMI or DMEM as a support medium. Changes in cell shape are detected by automated spectrophotometric readings automatically recorded every five minutes.

The optical density (OD) readings obtained in the MiCK® assay are plotted versus time to obtain a curve. The slope of the obtained curve is used in a proprietary equation to determine the amount of apoptosis induced. The unit of measure is the kinetic unit (KU). Although the disclosure refers to tests occurring in the wells of a 384 well spectrophotometric plate, one of skill in the art will recognize that numerous test sites are suitable for the test disclosed herein, and therefore, a 384 well spectrophotometric plate is a not limiting embodiment. For example, spectrophotometric plates of other sizes (6, 12, 24, 48, 96 well plates), cuvettes, test tubes, or any other suitable structure known in the art can be used.

The terminology used in the description presented herein is not intended to be interpreted in any limited or restrictive manner and unless otherwise indicated refers to the ordinary meaning as would be understood by one of ordinary skill in the art in view of the specification. Furthermore, embodiments may comprise, consist of, or consist essentially of, several novel features, no single one of which is solely responsible for its desirable attributes or is believed to be essential to practicing the embodiments herein described. As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

Although this disclosure is in the context of certain embodiments and examples, those of ordinary skill in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of ordinary skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

Abbreviations

NPs Nanoparticles
QC Quercetin
FITC Fluorescein isothiocyanate
PLGA poly (lactide-co-glycolide)
PEG Polyethylene Glycol
FA Folic acid
DSPE_PEG 1,2-Distearoyl-sn-Glycero-3-Phosphoethanolamine-Amino (Polyethylene Glycol)
DLS Dynamic Light Scattering
NHS N-Hydroxysuccinimide

What is claimed is:

1. A pharmaceutical composition, comprising:
   synergistic amounts of:
   Afatinib; and
   a first anti-cancer response modulator,
   wherein the first anti-cancer response modulator is quercetin, and
   wherein the synergistic amounts of Afatinib and quercetin are effective for treatment of a neoplasm.

2. The pharmaceutical composition of claim 1, wherein at least a portion of the pharmaceutical composition is formulated for IV administration or oral administration.

3. The pharmaceutical composition of claim 1, wherein the amount Afatinib ranges between about 0.01 mg/day, mg/kg, or mg/m$^2$ and about 1000 mg/day, mg/kg, or mg/m$^2$.

4. The pharmaceutical composition of claim 1, wherein the amount of quercetin is 0.1 g to 2.5 g.

5. The pharmaceutical composition of claim 1, wherein the quercetin is in solution at a concentration of 10 mg/ml to 500 mg/ml.

6. The pharmaceutical composition of claim 1, wherein Afatinib and at least one anti-cancer response modulator are in a single dosage form for co-administration.

7. The pharmaceutical composition of claim 6, wherein Afatinib and at least one anti-cancer response modulator are in a single dosage form suitable for IV administration.

8. The pharmaceutical composition of claim 6, wherein Afatinib and at least one anti-cancer response modulator are in a single dosage form suitable for oral administration.

9. The pharmaceutical composition of claim 1, wherein Afatinib and at least one anti-cancer response modulator are in a separate dosage forms.

10. The pharmaceutical composition of claim 9, wherein Afatinib and at least one anti-cancer response modulator are each in dosage forms suitable for IV administration.

11. The pharmaceutical composition of claim 9, wherein Afatinib and at least one anti-cancer response modulator are each in dosage forms suitable for oral administration.

12. The pharmaceutical composition of claim 9, wherein either Afatinib or the at least one anti-cancer response modulator is in a dosage form suitable for oral administration and the other is in a dosage form for IV administration.

13. The pharmaceutical composition of claim 1, wherein the neoplasm is one or more of breast adenocarcinoma, pancreatic adenocarcinoma, lung carcinoma, prostate cancer, hormone refractory prostate cancer, solid tumor malignancies, colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, bladder cancer, hematological malignancies, squamous cell carcinomas, breast cancer, astrocytomas, pilocytic astrocytoma, diffuse astrocytoma, anaplastic astrocytoma, and brain stem gliomas, glioblastomas, glioblastoma multiforme, meningioma, gliomas, ependymomas, oligodendrogliomas, and mixed gliomas, brain tumors, pituitary tumors, craniopharyngiomas, germ cell tumors, pineal region tumors, medulloblastomas, and primary CNS lymphomas.

14. The pharmaceutical composition of claim 1, wherein the composition is a nanoparticle formulation.

15. A kit for treatment of a neoplasm, wherein the kit comprises a pharmaceutical composition according to claim 1, wherein:
    the pharmaceutical composition is in a single container.

16. The kit according to claim 15, wherein each of Afatinib and the one or more modulators are contained in a single container in a single dosage form.

17. The kit according to claim 15, wherein each of Afatinib and the one or more modulators are contained in separate sub-containers.

18. A method of treatment of a neoplasm, the method comprising:
    administering in a pharmaceutical composition, to a patient in need thereof,
    synergistically effective amounts of:
    Afatinib; and
    a first anti-cancer response modulator, wherein the first anti-cancer response modulator is quercetin.

19. The method of claim 18, wherein the pharmaceutical composition is administered to the subject IV, orally or both.

20. The method of claim 18, wherein the effect on the neoplasm is an improved result as compared to an effect on the neoplasm of either Afatinib alone or the first anti-cancer response modulator alone.

21. The method of claim 18, wherein Afatinib is administered at a dose of about 0.01 mg/day, mg/kg, or mg/m$^2$ to about 1000 mg/day, mg/kg, or mg/m$^2$.

22. The method of claim 18, wherein the quercetin is administered at a dose of 0.1 g to 2.5 g.

23. The method of claim 18, wherein the pharmaceutical composition causes an induction of apoptosis in vitro in at least one cancer cell line.

24. The method of claim 23, wherein the induction of apoptosis by the composition is additive as compared to the induction of apoptosis of each of the anti-cancer agents and at least one modulators alone.

25. The method of claim 23, wherein the induction of apoptosis by the composition is synergistic as compared to the induction of apoptosis of each of the anti-cancer agents and at least one modulator alone.

26. The method of claim 18, wherein quercetin is in a nanoparticle formulation.

27. The method of claim 18, wherein anti-cancer agent is in a nanoparticle formulation.

28. The method of claim 18, wherein both quercetin and the anti-cancer agent are in a nanoparticle formulation.

29. The method of claim 18, wherein the pharmaceutical composition is a nanoparticle formulation, which comprises a first population of nanoparticles with a first modulator, wherein the first modulator is quercetin, and a second population of nanoparticles with an anti-cancer agent.

30. The method of claim 18, wherein the pharmaceutical composition is a nanoparticle formulation, and wherein a dimension of nanoparticles in the nanoparticle formulation ranges from about 100 nm to about 250 nm.

31. The method of claim 18, wherein the pharmaceutical composition is a nanoparticle formulation, and wherein nanoparticle s in the nanoparticle formulation are selected from the group consisting of PLGA-PEG-NPs, FA-PLGA-PEG-NPs, DSPE-PEG-NPs and FA-DSPE-PEG-NPs.

32. The pharmaceutical composition of claim 1, wherein the pharmaceutical composition causes an induction of apoptosis in vitro in at least one cancer cell line.

33. The pharmaceutical composition of claim 32, wherein the induction of apoptosis by the composition is additive as compared to the induction of apoptosis of each of the anti-cancer agents and at least one modulators alone.

34. The pharmaceutical composition of claim 32, wherein the induction of apoptosis by the composition is synergistic as compared to the induction of apoptosis of each of the anti-cancer agents and at least one modulator alone.

35. The pharmaceutical composition of claim 1, wherein quercetin is in a nanoparticle formulation.

36. The pharmaceutical composition of claim 1, wherein anti-cancer agent is in a nanoparticle formulation.

37. The pharmaceutical composition of claim 1, wherein both quercetin and the anti-cancer agent are in a nanoparticle formulation.

38. The pharmaceutical composition of claim 1, wherein the pharmaceutical composition is a nanoparticle formulation, which comprises a first population of nanoparticles with a first modulator, wherein the first modulator is quercetin, and a second population of nanoparticles with an anti-cancer agent.

39. The pharmaceutical composition of claim 1, wherein the pharmaceutical composition is a nanoparticle formulation, and wherein a dimension of nanoparticles in the nanoparticle formulation ranges from about 100 nm to about 250 nm.

40. The pharmaceutical composition of claim 1, wherein the pharmaceutical composition is a nanoparticle formulation, and wherein nanoparticles in the nanoparticle formulation are selected from the group consisting of PLGA-PEG-NPs, FA-PLGA-PEG-NPs, DSPE-PEG-NPs and FA-DSPE-PEG-NPs.

41. The pharmaceutical composition of claim 1, wherein the pharmaceutical composition does not contain any active pharmaceutical ingredients other than the Afatinib and the quercetin.

42. The method of claim 18, wherein the pharmaceutical composition does not contain any active pharmaceutical ingredients other than the Afatinib and the quercetin.

* * * * *